United States Patent
Kloiber-Maitz et al.

(10) Patent No.: US 11,661,607 B2
(45) Date of Patent: May 30, 2023

(54) HAPLOIDIZATION IN SORGHUM

(71) Applicant: KWS SAAT SE & Co. KGaA, Einbeck (DE)

(72) Inventors: Monika Kloiber-Maitz, Einbeck (DE); Silke Wieckhorst, Einbeck (DE); Christof Bolduan, Einbeck (DE); Milena Ouzunova, Göttingen (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 327 days.

(21) Appl. No.: 16/489,201

(22) PCT Filed: Feb. 28, 2018

(86) PCT No.: PCT/EP2018/054901
§ 371 (c)(1),
(2) Date: Aug. 27, 2019

(87) PCT Pub. No.: WO2018/158301
PCT Pub. Date: Sep. 7, 2018

(65) Prior Publication Data
US 2019/0390213 A1    Dec. 26, 2019

(30) Foreign Application Priority Data
Feb. 28, 2017  (EP) .................................. 17158439

(51) Int. Cl.
*C12N 15/82* (2006.01)
*C12N 9/16* (2006.01)

(52) U.S. Cl.
CPC ............... *C12N 15/8231* (2013.01); *C12Y 301/04004* (2013.01); *C12N 9/16* (2013.01); *C12N 15/8287* (2013.01)

(58) Field of Classification Search
None
See application file for complete search history.

(56) References Cited

U.S. PATENT DOCUMENTS

2017/0327832 A1    11/2017    Bolduan et al.

FOREIGN PATENT DOCUMENTS

| EP | 2 989 889 A1 | 3/2016 |
| EP | 3 037 540 A1 | 6/2016 |
| WO | 2010/079430 A1 | 7/2010 |
| WO | 2011/072246 | 6/2011 |
| WO | 2016/075255 A1 | 5/2016 |
| WO | WO 2016/075255 A1 * | 5/2016 |
| WO | 2016/138021 A1 | 9/2016 |
| WO | 2016/177887 A1 | 11/2016 |
| WO | WO 2016/177887 * | 11/2016 |
| WO | WO 2018/035070 A3 * | 2/2018 |

OTHER PUBLICATIONS

Patatin-like hypothetical protein SORBIDRAFT_01g033380 [Sorghum bicolor], NCBI/GenBank accession No. XP_002467750, published Jul. 13, 2009.*
Kelliher et al., 2017, Matrilineal, a sperm-specific phospholipase, triggers maize haploid induction; Nature 542: 105-109.*
International Search Report dated Apr. 23, 2018 for corresponding PCT Application No. PCT/EP2018/054901.
Gilles et al., "Loss of pollen-specific phospholipase Not Like Dad triggers gynogenesis in maize", The EMBO Journal, vol. 36, No. 6, 2017, pp. 707-717.
Kelliher et al., "Matrilineal, a sperm-specific phospholipase, triggers maize haploid induction", Nature, vol. 542, No. 7639, 2017, pp. 105-109.
Liu et al., "A 4-bp Insertion at ZmPLA1 Encoding a Putative Phospholipase A Generates Haploid Induction in Maize", Molecular Plant, vol. 10, No. 3, 2017, pp. 520-522.
Li et al., "Map-based cloning and expression analysis of BMR-6 in sorghum", Journal of Genetics, 2015, vol. 94, No. 3, pp. 445-452.
Fire et al., "Potent and specific genetic interference by double-stranded RNA in Caenorhabditis elegans", Nature, 1998, vol. 391, pp. 806-811.
Till et al., "Discovery of induced point mutations in maize genes by Tilling", BMC Plant Biology, 2004, vol. 4, No. 12, 8 pages.
Silva et al., "Meganucleases and Other Tools for Targeted Genome Engineering: Perspectives and Challenges for Gene Therapy", Current Gene Therapy, 2011, vol. 11, pp. 11-27.
Chevalier et al., "Design, Activity, and Structure of a Highly Specific Artificial Endonuclease", Molecular Cell, 2002, vol. 10, pp. 895-905.
Lloyd et al., "Targeted mutagenesis using zinc-finger nucleases in *Arabidopsis*", PNAS, 2005, vol. 102, No. 6, pp. 2232-2237.
Gaj et al., "ZFN, TALEN and CRISPR/Cas-based methods for genome engineering", Trends in Biotechnology, 2013, vol. 31, No. 7, pp. 397-405.
Ravi et al., "Haploid plants produced by centromere-mediated genome elimination", Nature, 2010, vol. 464, pp. 615-618.
Segui-Simarro et al., "Pathways to doubled hapioidy: chromosome doubling during androgenesis", Cytogenetic and Genome Research, 2008, vol. 120, pp. 358-369.
Dwivedi et al., "Haploids: Constraints and opportunities in plant breeding", Biotechnology Advances, 2015, vol. 33, pp. 812-829.

* cited by examiner

Primary Examiner — Charles Logsdon
Assistant Examiner — Wayne Zhong
(74) Attorney, Agent, or Firm — Troutman Pepper Hamilton Sanders LLP

(57)    ABSTRACT

Sorghum plants are provided which are capable of inducing haploidy by modifications in the genome related to a pollen-specific expressed patatin phospholipid producing haploid offspring and can be produced for hybrid breeding in short time by chromosome doubling inbred lines, that is, homozygous father and mother lines. In addition, methods are provided for producing transgenic and non-transgenic plant haploid inducers and improving the induction performance of plants.

13 Claims, 2 Drawing Sheets
Specification includes a Sequence Listing.

```
Sorghum_PPL_AA        MATYYSSRRPCNACSTKAMAGSVVGEPVVLGQRVTVLTVDGGGIRGLIPGTILAFLEARL
Sorghum_PPL_R59Q      MATYYSSRRPCNACSTKAMAGSVVGEPVVLGQRVTVLTVDGGGIRGLIPGTILAFLEAQL
Sorghum_PPL_V162I     MATYYSSRRPCNACSTKAMAGSVVGEPVVLGQRVTVLTVDGGGIRGLIPGTILAFLEARL
Sorghum_PPL_S291L     MATYYSSRRPCNACSTKAMAGSVVGEPVVLGQRVTVLTVDGGGIRGLIPGTILAFLEARL
Sorghum_PPL_Q372stop  MATYYSSRRPCNACSTKAMAGSVVGEPVVLGQRVTVLTVDGGGIRGLIPGTILAFLEARL
                      *********************************************************:*

Sorghum_PPL_AA        QELDGPEVRLADYFDYIAGTSTGGLITAMLTAPGKDRRPLYAAKDINQFYMENCPRIFPQ
Sorghum_PPL_R59Q      QELDGPEVRLADYFDYIAGTSTGGLITAMLTAPGKDRRPLYAAKDINQFYMENCPRIFPQ
Sorghum_PPL_V162I     QELDGPEVRLADYFDYIAGTSTGGLITAMLTAPGKDRRPLYAAKDINQFYMENCPRIFPQ
Sorghum_PPL_S291L     QELDGPEVRLADYFDYIAGTSTGGLITAMLTAPGKDRRPLYAAKDINQFYMENCPRIFPQ
Sorghum_PPL_Q372stop  QELDGPEVRLADYFDYIAGTSTGGLITAMLTAPGKDRRPLYAAKDINQFYMENCPRIFPQ
                      ************************************************************

Sorghum_PPL_AA        KSSRLAAAMSALRKPRYNGKCLRNLIMSMLGETRVSDTLTNVIIPTFDVRLLQPIIFSTY
Sorghum_PPL_R59Q      KSSRLAAAMSALRKPRYNGKCLRNLIMSMLGETRVSDTLTNVIIPTFDVRLLQPIIFSTY
Sorghum_PPL_V162I     KSSRLAAAMSALRKPRYNGKCLRNLIMSMLGETRVSDTLTNIIIPTFDVRLLQPIIFSTY
Sorghum_PPL_S291L     KSSRLAAAMSALRKPRYNGKCLRNLIMSMLGETRVSDTLTNVIIPTFDVRLLQPIIFSTY
Sorghum_PPL_Q372stop  KSSRLAAAMSALRKPRYNGKCLRNLIMSMLGETRVSDTLTNVIIPTFDVRLLQPIIFSTY
                      *****************************************:******************

Sorghum_PPL_AA        DAKSMPLKNALLSDVCIGTSAAPTYLPAHYFQTKDAGSGKEREYNLIDGGVAANNPTMVA
Sorghum_PPL_R59Q      DAKSMPLKNALLSDVCIGTSAAPTYLPAHYFQTKDAGSGKEREYNLIDGGVAANNPTMVA
Sorghum_PPL_V162I     DAKSMPLKNALLSDVCIGTSAAPTYLPAHYFQTKDAGSGKEREYNLIDGGVAANNPTMVA
Sorghum_PPL_S291L     DAKSMPLKNALLSDVCIGTSAAPTYLPAHYFQTKDAGSGKEREYNLIDGGVAANNPTMVA
Sorghum_PPL_Q372stop  DAKSMPLKNALLSDVCIGTSAAPTYLPAHYFQTKDAGSGKEREYNLIDGGVAANNPTMVA
                      ************************************************************

Sorghum_PPL_AA        MTQITKKMLASKEKAEELYPVKPWNCRKFLVLSIGTGSTSEQGLYTARQCSRWGICRWIR
Sorghum_PPL_R59Q      MTQITKKMLASKEKAEELYPVKPWNCRKFLVLSIGTGSTSEQGLYTARQCSRWGICRWIR
Sorghum_PPL_V162I     MTQITKKMLASKEKAEELYPVKPWNCRKFLVLSIGTGSTSEQGLYTARQCSRWGICRWIR
Sorghum_PPL_S291L     MTQITKKMLASKEKAEELYPVKPWNCRKFLVLSIGTGSTSEQGLYTARQCLRWGICRWIR
Sorghum_PPL_Q372stop  MTQITKKMLASKEKAEELYPVKPWNCRKFLVLSIGTGSTSEQGLYTARQCSRWGICRWIR
                      ************************************************** *********

Sorghum_PPL_AA        NNGMAPIIDIFMAASSDLVDIHVAAMFQSLHSDGDYLRIQDNSLHGAAATVDAATPENMR
Sorghum_PPL_R59Q      NNGMAPIIDIFMAASSDLVDIHVAAMFQSLHSDGDYLRIQDNSLHGAAATVDAATPENMR
Sorghum_PPL_V162I     NNGMAPIIDIFMAASSDLVDIHVAAMFQSLHSDGDYLRIQDNSLHGAAATVDAATPENMR
Sorghum_PPL_S291L     NNGMAPIIDIFMAASSDLVDIHVAAMFQSLHSDGDYLRIQDNSLHGAAATVDAATPENMR
Sorghum_PPL_Q372stop  NNGMAPIIDIFMAASSDLVDIHVAAMFQSLHSDGDYLRIQDNSLHGAAATVDAATPENMR
                      ************************************************************

Sorghum_PPL_AA        TLVGIGERMLAQRVSRVNVETGRYEPVPGEGSNADALAGIARQLSEERRTRLARRTSAIV
Sorghum_PPL_R59Q      TLVGIGERMLAQRVSRVNVETGRYEPVPGEGSNADALAGIARQLSEERRTRLARRTSAIV
Sorghum_PPL_V162I     TLVGIGERMLAQRVSRVNVETGRYEPVPGEGSNADALAGIARQLSEERRTRLARRTSAIV
Sorghum_PPL_S291L     TLVGIGERMLAQRVSRVNVETGRYEPVPGEGSNADALAGIARQLSEERRTRLARRTSAIV
Sorghum_PPL_Q372stop  TLVGIGERMLA-------------------------------------------------
                      ***********

Sorghum_PPL_AA        SSGGASRRTCASKVSNV
Sorghum_PPL_R59Q      SSGGASRRTCASKVSNV
Sorghum_PPL_V162I     SSGGASRRTCASKVSNV
Sorghum_PPL_S291L     SSGGASRRTCASKVSNV
Sorghum_PPL_Q372stop  -----------------
                      *****************
```

FIG 1

```
Sorghum bicolor_PPL_AA      MATYYSSRRPCNACSTKAM------------AGSVVGEPVVLGQRVTVLTVDGGGIRGLI
Hordeum vulgare_PPL_AA      -MASYWCRRPCESCSTRAM------------AGSVVGQPVAPGQRVTVLTIDGGGIRGLI
Helianthus annuus_PPL_AA    ------------MNNINLVIVSLVIAIVAIQPLAQEQTDVGEANFVTVLSIDGGGVRGIV
Beta vulgaris_PPL1_AA       ------------MENSRSL------------GNPVSPRPPNHGNLITILSIDGGGIRGII
Beta vulgaris_PPL2_AA       ------------MTN--LQ------------SSPPSFNYYNRKKLVTILSIDGGGIRGII
                                        .                       : :*:*::****:**::

Sorghum bicolor_PPL_AA      PGTILAFLEARLQELDGPEVRLADYFDYIAGTSTGGLITAMLTAPGKDRRPLYAAKDINQ
Hordeum vulgare_PPL_AA      PGTILAFLEARLQELDGPDARLADYFDCIAGTSTGGLITAMLTAPGQDGRPLFAAKDVNR
Helianthus annuus_PPL_AA    PATLLAFLESKIQEIDGPDARIADYFDVIAGTSTGGLMTTMLAAPNEKNRPMFAAKDITN
Beta vulgaris_PPL1_AA       PAVMLEFLESQLQKLDGEEARLADYFDVIAGTSTGGLITAMLTAPNDKTRPLYAAKEITP
Beta vulgaris_PPL2_AA       PAVILAFLERLLQELDGEEVRLADYFDVIAGTSTGGLITAMLTAPDDYNRPLYAAKDITT
                            *..:* ***   :*::** :.*:***** *********:*:**:**.. **::***::.

Sorghum bicolor_PPL_AA      FYMENCPRIFPQKSSRL---------------------AA---AMSALRKPRYNGKCLRN
Hordeum vulgare_PPL_AA      FYLDNGPYIFPQRRCAL---------------------AA---VTASLRRPRYSGKYLHG
Helianthus annuus_PPL_AA    FYFQHSPRIFPKIGHTFDEAQPYPSQNEACEMGRTKFMNSVVTVLGEATGPKYDGKYLRA
Beta vulgaris_PPL1_AA       FYLEHCPKIFRQPSGIF---------------------GSIGTLMKLLSGPKYDGKYLHN
Beta vulgaris_PPL2_AA       FYLKHGPQIFPQERGPL---------------------AQLISFIKAMTGPKYDGKYLRH
                            **:.: * **   :                                 *:*.** ::

Sorghum bicolor_PPL_AA      LIMSMLGETRVSDTLTNVIIPTFDVRLLQPIIFSTYDAKSMPLKNALLSDVCIGTSAAPT
Hordeum vulgare_PPL_AA      KIRSMLGETRLCDALTDVVIPTFDVKLLQPIIFSTYDARNMPLKNARLADICIGTSAAPT
Helianthus annuus_PPL_AA    MAKMMLKNLTIKDTLTNIVIPAFDIRRLQPVIFSSAQGKEVAWKNALLADVCISTAAAPT
Beta vulgaris_PPL1_AA       LVKELLGQRRLHQALTNVVIPTFDIKNLQPVLFSTYMVPIAKELDVLLSDICIGTSAAPT
Beta vulgaris_PPL2_AA       ILREKLKETRLHHTLTNVVIPTFDIKTFQPVIFSSYKILSYPDLDAKLSDICIGTSAAPT
                                  *  :            :.  *:*:**.*:****

Sorghum bicolor_PPL_AA      YLPAHYFQTKDAGSGKEREYNLIDGGVAANNPTMVAMTQITKKMLASKEKAEELYPVKPW
Hordeum vulgare_PPL_AA      YLPAHHFHTQDD-NGKEREYNLIDGGVAANNPTMVTMTQITKKMMVK--DREELYPVKPS
Helianthus annuus_PPL_AA    FFPPYYFETRDV-DGTKHTFDLIDGGVAANNPTHLAITHITKEAVMG---KYRFSGPEVF
Beta vulgaris_PPL1_AA       FLPAHHFENKDD-QGNVKEFNLIDGGIAANNPSLVAISEVTKQIVKS---NPNFFPIKAT
Beta vulgaris_PPL2_AA       ILPSFYFQNAFE-NEKTREFNLIDGGIVSTNPTYLAINEVTKQMMKE---NPDYGTI---
                             :*  ..:*..   .  . : ::*****:.:.**: :::...:**:  :

Sorghum bicolor_PPL_AA      NCRKFLVLSIGTGSTSEQGLYTARQCSRWGICRWIRNNGMAPIIDIFMAASSDLVDIHVA
Hordeum vulgare_PPL_AA      DCGKFLVLSIGTGSTSDQGLYTAKQCSQWGIIRWLRNKGMAPIIDIFMAASSDLVDIHAA
Helianthus annuus_PPL_AA    DGRRMLVLSLGTGTQTYNDLYTAQKAAKWGLLSWIFTNGTAPILRIFGDAMSDMVDIHVS
Beta vulgaris_PPL1_AA       DRERLLVISLGTGSDKVEQLYNAKSAAKWGIISWLFDNGNTPLLDAFNQSKADMVDFHNS
Beta vulgaris_PPL2_AA       -HNKLLVLSIGTGSSGKIEQKYNAKTAGKWGLVSWLFQNGSSPIISAFYEAGADLVDYQNN
                              : :**:*:****:  . :   *.*:  ..:**:  *:   :* :*::  *   : :*:**  :

Sorghum bicolor_PPL_AA      AMFQSLHSDGDYLRIQDNSLHGAAATVDAATPENMRTLVGIGERMLAQRVSRVNVETGRY
Hordeum vulgare_PPL_AA      VLFQSLHSDGNYLRIQDNSLHGPAATVDAATPENMAELLRIGERMLAQRVSRVNVETGRY
Helianthus annuus_PPL_AA    TIFQSLQVEKNYLRIQEDNLKGEATAMDISSPENMRALEDIGKKLLKKPLSRLDVETGKL
Beta vulgaris_PPL1_AA       VAFQAYGSLDNYLRIQDDTLKGVSASVDVATTENLANLVTIGKALLKKPVSRINFDTGRY
Beta vulgaris_PPL2_AA       ILFQSFRSEDKYLRVQDDSLTGTTASTDVATEKNLENLVKIGQELLNKPASRVDPETGHL
                              **:         .:***:::..*  *   *  :::  *   *  **:  :*  :   **::   :**:

Sorghum bicolor_PPL_AA      EPVPGEGSNADALAGIARQLSEERRTRLARRTSAIVSSGGASRRTCASKVSNV
Hordeum vulgare_PPL_AA      EEIRGAGSNADALAGFAKQLSDERRTRLGRRRVGAGRLKSRR----------
Helianthus annuus_PPL_AA    EPVKGEGTNADALARFATLLCAERKRRNP-----------------------
Beta vulgaris_PPL1_AA       QPIPNGGTNEEALIRFAKLLTEEKSRREQYRTNRSD----------------
Beta vulgaris_PPL2_AA       KAIPHLGTNADALRRFAKQLSDERKYRRGKDSNQMQEYS-------------
                            : :    *:* :**  :*    *   *:                  *
```

FIG 2

```
                          SEQUENCE LISTING

<160> NUMBER OF SEQ ID NOS: 45

<210> SEQ ID NO 1
<211> LENGTH: 2031
<212> TYPE: DNA
<213> ORGANISM: Sorghum bicolor

<400> SEQUENCE: 1
acgcagtgcc tatatacaca agccaccatc tgtcgttgcc tcctcctcct cagctcatca      60
ctagtcacac gtacaccccgc aatcgattga aaatttatcg cgttcgtcca aacaatacca    120
gagctcgacg atcatcttaa ttgttggatc gatctgaata atctttcttc attcgtggcc    180
tcgacgagta agtaggtagc tcatttgatc gatcaaccgc gagtgtgtgc ttgatcgaag    240
gcggcaatgg cgacctacta ctcttcgcgg cgtccatgca acgcctgcag cacgaaggcg    300
atggccggga gcgtggtcgg cgagcccgtc gtgctgggggc agagggtgac ggtgctgacg    360
gtggacggcg gcggcatccg tggtctcatc cccggaacca tccttgcctt cctcgaggcc    420
cggctgcagg agctggacgg gccggaggtt aggctcgcgg actacttcga ctacatcgcc    480
gggacgagca ccggcgggct catcaccgcc atgctcaccg cgcccggcaa ggacaggcgg    540
cctctctacg ctgccaagga catcaaccaa ttctacatgg agaattgccc tcgcatcttc    600
cctcaaaagt gagtccgatc atcccggccg gccgccattg ttggcctcgc attattgatc    660
gatcatgcat gcatgcatgc atgtgatgtg taggagcagc aggcttgcgg ccgccatgtc    720
cgcgctgagg aagccaaggt acaacggcaa gtgcctccgt aacctgatca tgagcatgct    780
cggcgagacg agggtgagcg cacgctcac caacgtcatc atccctacct tcgacgtcag    840
gctgctgcag cccatcatct tctccaccta cgacgtacgt acgccgccgg ccgccgtcgt    900
catgaataat caatcagctg tacattattg cacatggctg catgcctact gaacatgttt    960
aatttgcagg ccaagagcat gcctctgaag aacgcgctgc tctccgacgt gtgcatcggc   1020
acgtccgccg cgccgaccta cctcccggcg cactacttcc agaccaagga cgccggcagt   1080
ggcaaggaac gcgagtacaa cctcatcgac ggcggtgtcg ccgccaacaa tccggtaatt   1140
aattaactga aaacgaacga acgcaattcc atatccattg tccagaagat cgatgctaat   1200
tgttgcttag gcacgtcgtt gccgccggcc gattgcattg cacttgcaca tgcgtagacg   1260
atggttgcga tgacgcagat caccaagaag atgcttgcca gcaaggagaa ggccgaggag   1320
ctgtacccag tgaagccgtg gaactgccgc aagttcctgg tgctgtccat cgggacgggg   1380
tcgacgtcgg agcagggcct gtacacgcgg cggcagtgct cgcggtgggg catctgccgg   1440
tggatccgga acaacggcat ggcccccatc atcgacatct tcatggcggc gagctcggac   1500
ctggtggaca tccacgtcgc cgcgatgttc cagtcgctcc acagcgacgg cgactacctg   1560
cgcatccagg acaactcgct gcacggcgcc gcggccaccg tggacgcggc gacgccggag   1620
aacatgcgga cgctcgtcgg gatcggggag cggatgctgg cgcagcgggt gtccagggtc   1680
aacgtggaga cagggaggta cgaaccggtg cctggggaag gaagcaacgc tgatgcgctc   1740
gctgggatcg caaggcagct ctcggaggag aggaggacaa ggctcgcgcg ccgcacctcc   1800
gccatcgtca gctccggtgg tgcctctaga cgtacgtgtg cctcaaaggt ctccaatgtc   1860
taagagaagt gaatttgttg cctgattaaa atcttaatta attaattctg tgggctgtgg   1920
```

```
ctcaaataaa actatatcat taaaaaaccc gccatgaact agttctagga aaatacgcat     1980
ggttttagaa agaaaaacat aaactaattc taacaaaatg tacacacctc t              2031
```

<210> SEQ ID NO 2
<211> LENGTH: 1314
<212> TYPE: DNA
<213> ORGANISM: Artificial Sequence
<220> FEATURE:
<223> OTHER INFORMATION: cDNA of Sorghum bicolor Phospholipase

<400> SEQUENCE: 2

```
atggcgacct actactcttc gcggcgtcca tgcaacgcct gcagcacgaa ggcgatggcc       60
gggagcgtgg tcggcgagcc cgtcgtgctg gggcagaggg tgacggtgct gacggtggac      120
ggcggcggca tccgtggtct catccccgga accatcct tg ccttcctcga ggcccggctg     180
caggagctgg acgggccgga ggttaggctc gcggactact cgactacat cgccgggacg       240 agcaccggcg ggctcatcac cgccatgctc accgcgcccg gcaaggacag gcggcctctc      300
tacgctgcca aggacatcaa ccaattctac atggagaatt gccctcgcat cttccctcaa      360
aagagcagca ggcttgcggc cgccatgtcc gcgctgagga agccaaggta caacggcaag      420
tgcctccgta acctgatcat gagcatgctc ggcgagacga gggtgagcga cacgctcacc      480
aacgtcatca tccctacctt cgacgtcagg ctgctgcagc ccatcatctt ctccacctac      540
gacgccaaga gcatgcctct gaagaacgcg ctgctctccg acgtgtgcat cggcacgtcc      600
gccgcgccga cctacctccc ggcgcactac ttccagacca aggacgccgg cagtggcaag      660
gaacgcgagt acaacctcat cgacggcggt gtcgccgcca acaatccgac gatggttgcg      720
atgacgcaga tcaccaagaa gatgcttgcc agcaaggaga aggccgagga gctgtaccca      780
gtgaagccgt ggaactgccg caagttcctg gtgctgtcca tcgggacggg gtcgacgtcg      840
gagcagggcc tgtacacggc gcggcagtgc tcgcggtggg gcatctgccg gtggatccgg      900
aacaacggca tggcccccat catcgacatc ttcatggcgg cgagctcgga cctggtggac      960
atccacgtcg ccgcgatgtt ccagtcgctc cacagcgacg cgactacct gcgcatccag      1020 gacaactcgc tgcacggcgc cgcggccacc gtggacgcgg cgacgccgga gaacatgcgg      1080
acgctcgtcg ggatcgggga gcggatgctg gcgcagcggg tgtccagggt caacgtggag      1140
acagggaggt acgaaccggt gcctggggaa ggaagcaacg ctgatgcgct cgctgggatc      1200
gcaaggcagc tctcggagga gaggaggaca aggctcgcgc gccgcacctc cgccatcgtc      1260
agctccggtg gtgcctctag acgtacgtgt gcctcaaagg tctccaatgt ctaa           1314
```

<210> SEQ ID NO 3
<211> LENGTH: 437
<212> TYPE: PRT
<213> ORGANISM: Sorghum bicolor

<400> SEQUENCE: 3

```
Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Gly Ile Arg Gly Leu Ile
        35                  40                  45

Pro Gly Thr Ile Leu Ala Phe Leu Glu Ala Arg Leu Gln Glu Leu Asp
    50                  55                  60
```

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
            85                  90                  95

Arg Arg Pro Leu Tyr Ala Ala Lys Asp Ile Asn Gln Phe Tyr Met Glu
            100                 105                 110

Asn Cys Pro Arg Ile Phe Pro Gln Lys Ser Arg Leu Ala Ala Ala
            115                 120                 125

Met Ser Ala Leu Arg Lys Pro Arg Tyr Asn Gly Lys Cys Leu Arg Asn
130                 135                 140

Leu Ile Met Ser Met Leu Gly Glu Thr Arg Val Ser Asp Thr Leu Thr
145                 150                 155                 160

Asn Val Ile Ile Pro Thr Phe Asp Val Arg Leu Leu Gln Pro Ile Ile
                165                 170                 175

Phe Ser Thr Tyr Asp Ala Lys Ser Met Pro Leu Lys Asn Ala Leu Leu
            180                 185                 190

Ser Asp Val Cys Ile Gly Thr Ser Ala Ala Pro Thr Tyr Leu Pro Ala
            195                 200                 205

His Tyr Phe Gln Thr Lys Asp Ala Gly Ser Gly Lys Glu Arg Glu Tyr
210                 215                 220

Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
                245                 250                 255

Glu Leu Tyr Pro Val Lys Pro Trp Asn Cys Arg Lys Phe Leu Val Leu
            260                 265                 270

Ser Ile Gly Thr Gly Ser Thr Ser Glu Gln Gly Leu Tyr Thr Ala Arg
            275                 280                 285

Gln Cys Ser Arg Trp Gly Ile Cys Arg Trp Ile Arg Asn Asn Gly Met
290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Ala Thr Val Asp
            340                 345                 350

Ala Ala Thr Pro Glu Asn Met Arg Thr Leu Val Gly Ile Gly Glu Arg
            355                 360                 365

Met Leu Ala Gln Arg Val Ser Arg Val Asn Val Glu Thr Gly Arg Tyr
370                 375                 380

Glu Pro Val Pro Gly Glu Gly Ser Asn Ala Asp Ala Leu Ala Gly Ile
385                 390                 395                 400

Ala Arg Gln Leu Ser Glu Glu Arg Arg Thr Arg Leu Ala Arg Arg Thr
                405                 410                 415

Ser Ala Ile Val Ser Ser Gly Gly Ala Ser Arg Arg Thr Cys Ala Ser
            420                 425                 430

Lys Val Ser Asn Val
        435

<210> SEQ ID NO 4
<211> LENGTH: 2031
<212> TYPE: DNA
<213> ORGANISM: Artificial Sequence
<220> FEATURE:

<223> OTHER INFORMATION: genomic DNA of mutated Sorghum bicolor
      phospholipase R59Q

<400> SEQUENCE: 4

```
acgcagtgcc tatatacaca agccaccatc tgtcgttgcc tcctcctcct cagctcatca      60
ctagtcacac gtacacccgc aatcgattga aaatttatcg cgttcgtcca acaatacca     120
gagctcgacg atcatcttaa ttgttggatc gatctgaata atctttcttc attcgtggcc    180
tcgacgagta agtaggtagc tcatttgatc gatcaaccgc gagtgtgtgc ttgatcgaag    240
gcggcaatgg cgacctacta ctcttcgcgg cgtccatgca acgcctgcag cacgaaggcg    300
atggccggga gcgtggtcgg cgagcccgtc gtgctgggc agagggtgac ggtgctgacg     360
gtggacggcg gcggcatccg tggtctcatc cccggaacca tccttgcctt cctcgaggcc    420
cagctgcagg agctggacgg gccggaggtt aggctcgcgg actacttcga ctacatcgcc    480
gggacgagca ccggcgggct catcaccgcc atgctcaccg cgcccggcaa ggacaggcgg    540
cctctctacg ctgccaagga catcaaccaa ttctacatgg agaattgccc tcgcatcttc    600
cctcaaaagt gagtccgatc atcccggccg gccgccattg ttggcctcgc attattgatc    660
gatcatgcat gcatgcatgc atgtgatgtg taggagcagc aggcttgcgg ccgccatgtc    720
cgcgctgagg aagccaaggt acaacggcaa gtgcctccgt aacctgatca tgagcatgct    780
cggcgagacg agggtgagcg cacgctcac caacgtcatc atccctacct tcgacgtcag     840
gctgctgcag cccatcatct tctccaccta cgacgtacgt acgccgccgg ccgccgtcgt    900
catgaataat caatcagctg tacattattg cacatggctg catgcctact gaacatgttt    960
aatttgcagg ccaagagcat gcctctgaag aacgcgctgc tctccgacgt gtgcatcggc   1020
acgtccgccg cgccgaccta cctcccggcg cactacttcc agaccaagga cgccggcagt   1080
ggcaaggaac gcgagtacaa cctcatcgac ggcggtgtcg ccgccaacaa tccggtaatt   1140
aattaactga aaacgaacga acgcaattcc atatccattg tccagaagat cgatgctaat   1200
tgttgcttag gcacgtcgtt gccgccggcc gattgcattg cacttgcaca tgcgtagacg   1260
atggttgcga tgacgcagat caccaagaag atgcttgcca gcaaggagaa ggccgaggag   1320
ctgtacccag tgaagccgtg gaactgccgc aagttcctgg tgctgtccat cgggacgggg   1380
tcgacgtcgg agcagggcct gtacacggcg cggcagtgct cgcggtgggg catctgccgg   1440
tggatccgga caacggcat ggcccccatc atcgacatct tcatggcggc gagctcggac    1500
ctggtggaca tccacgtcgc cgcgatgttc cagtcgctcc acagcgacgg cgactacctg   1560
cgcatccagg acaactcgct gcacggcgcc gcggccaccg tggacgcggc gacgccggag   1620
aacatgcgga cgctcgtcgg gatcggggag cggatgctgg cgcagcgggt gtccagggtc   1680
aacgtggaga cagggaggta cgaaccggtg cctggggaag gaagcaacgc tgatgcgctc   1740
gctgggatcg caaggcagct ctcggaggag aggaggacaa ggctcgcgcg ccgcacctcc   1800
gccatcgtca gctccggtgg tgcctctaga cgtacgtgtg cctcaaaggt ctccaatgtc   1860
taagagaagt gaatttgttg cctgattaaa atcttaatta attaattctg tgggctgtgg   1920
ctcaaataaa actatatcat taaaaaaccc gccatgaact agttctagga aaatacgcat   1980
ggttttagaa agaaaaacat aaactaattc taacaaaatg tacacacctc t            2031
```

<210> SEQ ID NO 5
<211> LENGTH: 1314
<212> TYPE: DNA
<213> ORGANISM: Artificial Sequence
<220> FEATURE:

<223> OTHER INFORMATION: cDNA of Sorghum bicolor phospholipase mutant
R59Q

<400> SEQUENCE: 5

```
atggcgacct actactcttc gcggcgtcca tgcaacgcct gcagcacgaa ggcgatggcc      60
gggagcgtgg tcggcgagcc cgtcgtgctg gggcagaggg tgacggtgct gacggtggac     120
ggcggcggca tccgtggtct catccccgga accatccttg ccttcctcga ggcccagctg     180
caggagctgg acgggccgga ggttaggctc gcggactact tcgactacat cgccgggacg     240
agcaccggcg ggctcatcac cgccatgctc accgcgcccg gcaaggacag gcggcctctc     300
tacgctgcca aggacatcaa ccaattctac atggagaatt gccctcgcat cttccctcaa     360
aagagcagca ggcttgcggc cgccatgtcc gcgctgagga agccaaggta caacggcaag     420
tgcctccgta acctgatcat gagcatgctc ggcgagacga gggtgagcga cacgctcacc     480
aacgtcatca tccctacctt cgacgtcagg ctgctgcagc ccatcatctt ctccacctac     540
gacgccaaga gcatgcctct gaagaacgcg ctgctctccg acgtgtgcat cggcacgtcc     600
gccgcgccga cctacctccc ggcgcactac ttccagacca aggacgccgg cagtggcaag     660
gaacgcgagt acaacctcat cgacggcggt gtcgccgcca acaatccgac gatggttgcg     720
atgacgcaga tcaccaagaa gatgcttgcc agcaaggaga aggccgagga gctgtaccca     780
gtgaagccgt ggaactgccg caagttcctg gtgctgtcca tcgggacggg gtcgacgtcg     840
gagcagggcc tgtacacggc gcggcagtgc tcgcggtggg gcatctgccg gtggatccgg     900
aacaacggca tggcccccat catcgacatc ttcatggcgg cgagctcgga cctggtggac     960
atccacgtcg ccgcgatgtt ccagtcgctc cacagcgacg cgactacct gcgcatccag    1020
gacaactcgc tgcacggcgc cgcggccacc gtggacgcgg cgacgccgga gaacatgcgg    1080
acgctcgtcg ggatcgggga gcggatgctg cgcagcgggg tgtccagggt caacgtggag    1140
acagggaggt acgaaccggt gcctggggaa ggaagcaacg ctgatgcgct cgctgggatc    1200
gcaaggcagc tctcggagga gaggaggaca aggctcgcgc gccgcacctc cgccatcgtc    1260
agctccggtg gtgcctctag acgtacgtgt gcctcaaagg tctccaatgt ctaa           1314
```

<210> SEQ ID NO 6
<211> LENGTH: 437
<212> TYPE: PRT
<213> ORGANISM: Artificial Sequence
<220> FEATURE:
<223> OTHER INFORMATION: amino acid sequence of mutated Sorghum bicolor
phospholipase R59Q

<400> SEQUENCE: 6

```
Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Ile Arg Gly Leu Ile
        35                  40                  45

Pro Gly Thr Ile Leu Ala Phe Leu Glu Ala Gln Leu Gln Glu Leu Asp
    50                  55                  60

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
                85                  90                  95
```

Arg Arg Pro Leu Tyr Ala Ala Lys Asp Ile Asn Gln Phe Tyr Met Glu
            100                 105                 110

Asn Cys Pro Arg Ile Phe Pro Gln Lys Ser Ser Arg Leu Ala Ala Ala
        115                 120                 125

Met Ser Ala Leu Arg Lys Pro Arg Tyr Asn Gly Lys Cys Leu Arg Asn
130                 135                 140

Leu Ile Met Ser Met Leu Gly Glu Thr Arg Val Ser Asp Thr Leu Thr
145                 150                 155                 160

Asn Val Ile Ile Pro Thr Phe Asp Val Arg Leu Leu Gln Pro Ile Ile
                165                 170                 175

Phe Ser Thr Tyr Asp Ala Lys Ser Met Pro Leu Lys Asn Ala Leu Leu
                180                 185                 190

Ser Asp Val Cys Ile Gly Thr Ser Ala Ala Pro Thr Tyr Leu Pro Ala
                195                 200                 205

His Tyr Phe Gln Thr Lys Asp Ala Gly Ser Gly Lys Glu Arg Glu Tyr
            210                 215                 220

Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
                245                 250                 255

Glu Leu Tyr Pro Val Lys Pro Trp Asn Cys Arg Lys Phe Leu Val Leu
                260                 265                 270

Ser Ile Gly Thr Gly Ser Thr Ser Glu Gln Gly Leu Tyr Thr Ala Arg
            275                 280                 285

Gln Cys Ser Arg Trp Gly Ile Cys Arg Trp Ile Arg Asn Asn Gly Met
            290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Thr Val Asp
            340                 345                 350

Ala Ala Thr Pro Glu Asn Met Arg Thr Leu Val Gly Ile Gly Glu Arg
            355                 360                 365

Met Leu Ala Gln Arg Val Ser Arg Val Asn Val Glu Thr Gly Arg Tyr
        370                 375                 380

Glu Pro Val Pro Gly Glu Gly Ser Asn Ala Asp Ala Leu Ala Gly Ile
385                 390                 395                 400

Ala Arg Gln Leu Ser Glu Glu Arg Arg Thr Arg Leu Ala Arg Arg Thr
            405                 410                 415

Ser Ala Ile Val Ser Ser Gly Gly Ala Ser Arg Arg Thr Cys Ala Ser
            420                 425                 430

Lys Val Ser Asn Val
        435

<210> SEQ ID NO 7
<211> LENGTH: 2031
<212> TYPE: DNA
<213> ORGANISM: Artificial Sequence
<220> FEATURE:
<223> OTHER INFORMATION: genomic DNA of mutated Sorghum bicolor
      phospholipase V162I

<400> SEQUENCE: 7

```
acgcagtgcc tatatacaca agccaccatc tgtcgttgcc tcctcctcct cagctcatca      60
ctagtcacac gtacacccgc aatcgattga aaatttatcg cgttcgtcca acaatacca     120
gagctcgacg atcatcttaa ttgttggatc gatctgaata atctttcttc attcgtggcc    180
tcgacgagta agtaggtagc tcatttgatc gatcaaccgc gagtgtgtgc ttgatcgaag    240
gcggcaatgg cgacctacta ctcttcgcgg cgtccatgca acgcctgcag cacgaaggcg    300
atggccggga gcgtggtcgg cgagcccgtc gtgctggggc agagggtgac ggtgctgacg    360
gtggacggcg gcggcatccg tggtctcatc cccggaacca tccttgcctt cctcgaggcc    420
cggctgcagg agctggacgg gccggaggtt aggctcgcgg actacttcga ctacatcgcc    480
gggacgagca ccggcgggct catcaccgcc atgctcaccg cgcccggcaa ggacaggcgg    540
cctctctacg ctgccaagga catcaaccaa ttctacatgg agaattgccc tcgcatcttc    600
cctcaaaagt gagtccgatc atcccggccg gccgccattg ttggcctcgc attattgatc    660
gatcatgcat gcatgcatgc atgtgatgtg taggagcagc aggcttgcgg ccgccatgtc    720
cgcgctgagg aagccaaggt acaacggcaa gtgcctccgt aacctgatca tgagcatgct    780
cggcgagacg agggtgagcg cacgctcac caacatcatc atccctacct tcgacgtcag    840
gctgctgcag cccatcatct tctccaccta cgacgtacgt acgccgccgg ccgccgtcgt    900
catgaataat caatcagctg tacattattg cacatggctg catgcctact gaacatgttt    960
aatttgcagg ccaagagcat gcctctgaag aacgcgctgc tctccgacgt gtgcatcggc   1020
acgtccgccg cgccgaccta cctcccggcg cactacttcc agaccaagga cgccggcagt   1080
ggcaaggaac gcgagtacaa cctcatcgac ggcggtgtcg ccgccaacaa tccggtaatt   1140
aattaactga aaacgaacga acgcaattcc atatccattg tccagaagat cgatgctaat   1200
tgttgcttag gcacgtcgtt gccgccggcc gattgcattg cacttgcaca tgcgtagacg   1260
atggttgcga tgacgcagat caccaagaag atgcttgcca gcaaggagaa ggccgaggag   1320
ctgtacccag tgaagccgtg gaactgccgc aagttcctgg tgctgtccat cgggacgggg   1380
tcgacgtcgg agcagggcct gtacacgcg cggcagtgct cgcggtgggg catctgccgg   1440
tggatccgga caacggcat ggcccccatc atcgacatct tcatggcggc gagctcggac   1500
ctggtggaca tccacgtcgc cgcgatgttc cagtcgctcc acagcgacgg cgactacctg   1560
cgcatccagg caactcgct gcacggcgcc gcggccaccg tggacgcggc gacgccggag   1620
aacatgcgga cgctcgtcgg gatcggggag cggatgctgg cgcagcgggt gtccagggtc   1680
aacgtggaga cagggaggta cgaaccggtg cctggggaag gaagcaacgc tgatgcgctc   1740
gctgggatcg caaggcagct ctcggaggag aggaggacaa ggctcgcgcg ccgcacctcc   1800
gccatcgtca gctccggtgg tgcctctaga cgtacgtgtg cctcaaaggt ctccaatgtc   1860
taagagaagt gaatttgttg cctgattaaa atcttaatta attaattctg tgggctgtgg   1920
ctcaaataaa actatatcat taaaaaaccc gccatgaact agttctagga aaatacgcat   1980
ggttttagaa agaaaaacat aaactaattc taacaaaatg tacacacctc t            2031
```

<210> SEQ ID NO 8
<211> LENGTH: 1314
<212> TYPE: DNA
<213> ORGANISM: Artificial Sequence
<220> FEATURE:
<223> OTHER INFORMATION: cDNA Sorghum bicolor Phospholipase mutant V162I

<400> SEQUENCE: 8

```
atggcgacct actactcttc gcggcgtcca tgcaacgcct gcagcacgaa ggcgatggcc      60
gggagcgtgg tcggcgagcc cgtcgtgctg gggcagaggg tgacggtgct gacggtggac     120
ggcggcggca tccgtggtct catccccgga accatccttg ccttcctcga ggcccggctg     180
caggagctgg acgggccgga ggttaggctc gcggactact cgactacat cgccgggacg      240
agcaccggcg ggctcatcac cgccatgctc accgcgcccg gcaaggacag gcggcctctc     300
tacgctgcca aggacatcaa ccaattctac atggagaatt gccctcgcat cttccctcaa     360
aagagcagca ggcttgcggc cgccatgtcc gcgctgagga agccaaggta caacggcaag     420
tgcctccgta acctgatcat gagcatgctc ggcgagacga gggtgagcga cacgctcacc     480
aacatcatca tccctacctt cgacgtcagg ctgctgcagc ccatcatctt ctccacctac     540
gacgccaaga gcatgcctct gaagaacgcg ctgctctccg acgtgtgcat cggcacgtcc     600
gccgcgccga cctacctccc ggcgcactac ttccagacca aggacgccgg cagtggcaag     660
gaacgcgagt acaacctcat cgacggcggt gtcgccgcca caatccgac gatggttgcg      720
atgacgcaga tcaccaagaa gatgcttgcc agcaaggaga aggccgagga gctgtaccca     780
gtgaagccgt ggaactgccg caagttcctg gtgctgtcca tcgggacggg gtcgacgtcg     840
gagcagggcc tgtacacggc gcggcagtgc tcgcggtggg gcatctgccg gtggatccgg     900
aacaacggca tggcccccat catcgacatc ttcatggcgg cgagctcgga cctggtggac     960
atccacgtcg ccgcgatgtt ccagtcgctc cacagcgacg gcgactacct gcgcatccag    1020
gacaactcgc tgcacggcgc gcggccacc gtggacgcgg cgacgccgga gaacatgcgg     1080
acgctcgtcg ggatcgggga gcggatgctg gcgcagcggg tgtccagggt caacgtggag    1140
acagggaggt acgaaccggt gcctggggaa ggaagcaacg ctgatgcgct cgctgggatc    1200
gcaaggcagc tctcggagga gaggaggaca aggctcgcgc cgcgcacctc cgccatcgtc    1260
agctccggtg gtgcctctag acgtacgtgt gcctcaaagg tctccaatgt ctaa          1314
```

<210> SEQ ID NO 9
<211> LENGTH: 437
<212> TYPE: PRT
<213> ORGANISM: Artificial Sequence
<220> FEATURE:
<223> OTHER INFORMATION: amino acid sequence of mutated Sorghum bicolor phospholipase V162I

<400> SEQUENCE: 9

```
Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Ile Arg Gly Leu Ile
        35                  40                  45

Pro Gly Thr Ile Leu Ala Phe Leu Glu Ala Arg Leu Gln Glu Leu Asp
    50                  55                  60

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
                85                  90                  95

Arg Arg Pro Leu Tyr Ala Ala Lys Asp Ile Asn Gln Phe Tyr Met Glu
            100                 105                 110
```

Asn Cys Pro Arg Ile Phe Pro Gln Lys Ser Ser Arg Leu Ala Ala Ala
    115                 120                 125

Met Ser Ala Leu Arg Lys Pro Arg Tyr Asn Gly Lys Cys Leu Arg Asn
130                 135                 140

Leu Ile Met Ser Met Leu Gly Glu Thr Arg Val Ser Asp Thr Leu Thr
145                 150                 155                 160

Asn Ile Ile Ile Pro Thr Phe Asp Val Arg Leu Leu Gln Pro Ile Ile
                165                 170                 175

Phe Ser Thr Tyr Asp Ala Lys Ser Met Pro Leu Lys Asn Ala Leu Leu
                180                 185                 190

Ser Asp Val Cys Ile Gly Thr Ser Ala Ala Pro Thr Tyr Leu Pro Ala
            195                 200                 205

His Tyr Phe Gln Thr Lys Asp Ala Gly Ser Gly Lys Glu Arg Glu Tyr
        210                 215                 220

Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
                245                 250                 255

Glu Leu Tyr Pro Val Lys Pro Trp Asn Cys Arg Lys Phe Leu Val Leu
            260                 265                 270

Ser Ile Gly Thr Gly Ser Thr Ser Glu Gln Gly Leu Tyr Thr Ala Arg
        275                 280                 285

Gln Cys Ser Arg Trp Gly Ile Cys Arg Trp Ile Arg Asn Asn Gly Met
    290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Ala Thr Val Asp
            340                 345                 350

Ala Ala Thr Pro Glu Asn Met Arg Thr Leu Val Gly Ile Gly Glu Arg
        355                 360                 365

Met Leu Ala Gln Arg Val Ser Arg Val Asn Val Glu Thr Gly Arg Tyr
    370                 375                 380

Glu Pro Val Pro Gly Glu Gly Ser Asn Ala Asp Ala Leu Ala Gly Ile
385                 390                 395                 400

Ala Arg Gln Leu Ser Glu Glu Arg Arg Thr Arg Leu Ala Arg Arg Thr
                405                 410                 415

Ser Ala Ile Val Ser Ser Gly Gly Ala Ser Arg Arg Thr Cys Ala Ser
            420                 425                 430

Lys Val Ser Asn Val
        435

<210> SEQ ID NO 10
<211> LENGTH: 2031
<212> TYPE: DNA
<213> ORGANISM: Artificial Sequence
<220> FEATURE:
<223> OTHER INFORMATION: genomic DNA of mutated Sorghum bicolor
      phospholipase S291L

<400> SEQUENCE: 10
acgcagtgcc tatatacaca agccaccatc tgtcgttgcc tcctcctcct cagctcatca      60
ctagtcacac gtacacccgc aatcgattga aaatttatcg cgttcgtcca acaatacca     120

-continued

```
gagctcgacg atcatcttaa ttgttggatc gatctgaata atctttcttc attcgtggcc      180
tcgacgagta agtaggtagc tcatttgatc gatcaaccgc gagtgtgtgc ttgatcgaag      240
gcggcaatgg cgacctacta ctcttcgcgg cgtccatgca acgcctgcag cacgaaggcg      300
atggccggga gcgtggtcgg cgagcccgtc gtgctgggc agagggtgac ggtgctgacg       360
gtggacggcg gcggcatccg tggtctcatc cccggaacca tccttgcctt cctcgaggcc      420
cggctgcagg agctggacgg gccggaggtt aggctcgcgg actacttcga ctacatcgcc      480
gggacgagca ccggcgggct catcaccgcc atgctcaccg cgcccggcaa ggacaggcgg      540
cctctctacg ctgccaagga catcaaccaa ttctacatgg agaattgccc tcgcatcttc      600
cctcaaaagt gagtccgatc atcccggccg gccgccattg ttggcctcgc attattgatc      660
gatcatgcat gcatgcatgc atgtgatgtg taggagcagc aggcttgcgg ccgccatgtc      720
cgcgctgagg aagccaaggt acaacggcaa gtgcctccgt aacctgatca tgagcatgct      780
cggcgagacg agggtgagcg acacgctcac caacgtcatc atccctacct tcgacgtcag      840
gctgctgcag cccatcatct tctccaccta cgacgtacgc acgccgccgg ccgccgtcgt      900
catgaataat caatcagctg tacattattg cacatggctg catgcctact gaacatgttt      960
aatttgcagg ccaagagcat gcctctgaag aacgcgctgc tctccgacgt gtgcatcggc     1020
acgtccgccg cgccgaccta cctcccggcg cactacttcc agaccaagga cgccggcagt     1080
ggcaaggaac gcgagtacaa cctcatcgac ggcggtgtcg ccgccaacaa tccggtaatt     1140
aattaactga aaacgaacga acgcaattcc atatccattg tccagaagat cgatgctaat     1200
tgttgcttag gcacgtcgtt gccgccggcc gattgcattg cacttgcaca tgcgtagacg     1260
atggttgcga tgacgcagat caccaagaag atgcttgcca gcaaggagaa ggccgaggag     1320
ctgtacccag tgaagccgtg gaactgccgc aagttcctgg tgctgtccat cgggacgggg     1380
tcgacgtcgg agcagggcct gtacacggcg cggcagtgct tgcggtgggg catctgccgg     1440
tggatccgga caacggcat ggcccccatc atcgacatct tcatggcggc gagctcggac      1500
ctggtggaca tccacgtcgc cgcgatgttc cagtcgctcc acagcgacgg cgactacctg     1560
cgcatccagg acaactcgct gcacggcgcc gcggccaccg tggacgcggc gacgccggag     1620
aacatgcgga cgctcgtcgg gatcggggag cggatgctgg cgcagcgggt gtccagggtc     1680
aacgtggaga cagggaggta cgaaccggtg cctggggaag gaagcaacgc tgatgcgctc     1740
gctgggatcg caaggcagct ctcggaggag aggaggacaa ggctcgcgcg ccgcacctcc     1800
gccatcgtca gctccggtgg tgcctctaga cgtacgtgtg cctcaaaggt ctccaatgtc     1860
taagagaagt gaatttgttg cctgattaaa atcttaatta attaattctg tgggctgtgg     1920
ctcaaataaa actatatcat taaaaaaccc gccatgaact agttctagga aaatacgcat     1980
ggttttagaa agaaaaacat aaactaattc taacaaaatg tacacacctc t             2031
```

<210> SEQ ID NO 11
<211> LENGTH: 1314
<212> TYPE: DNA
<213> ORGANISM: Artificial Sequence
<220> FEATURE:
<223> OTHER INFORMATION: cDNA of Sorghum bicolor phospholipase mutant
      S291L

<400> SEQUENCE: 11

```
atggcgacct actactcttc gcggcgtcca tgcaacgcct gcagcacgaa ggcgatggcc       60
gggagcgtgg tcggcgagcc cgtcgtgctg gggcagaggg tgacggtgct gacggtggac     120
```

```
ggcggcggca tccgtggtct catccccgga accatccttg ccttcctcga ggcccggctg    180
caggagctgg acgggccgga ggttaggctc gcggactact tcgactacat cgccgggacg    240
agcaccggcg ggctcatcac cgccatgctc accgcgcccg gcaaggacag gcggcctctc    300
tacgctgcca aggacatcaa ccaattctac atggagaatt gccctcgcat cttccctcaa    360
aagagcagca ggcttgcggc cgccatgtcc gcgctgagga agccaaggta acggcaag     420 tgcctccgta acctgatcat gagcatgctc ggcgagacga gggtgagcga cacgctcacc    480
aacgtcatca tccctacctt cgacgtcagg ctgctgcagc ccatcatctt ctccacctac    540
gacgccaaga gcatgcctct gaagaacgcg ctgctctccg acgtgtgcat cggcacgtcc    600
gccgcgccga cctacctccc ggcgcactac ttccagacca aggacgccgg cagtggcaag    660
gaacgcgagt acaacctcat cgacggcggt gtcgccgcca acaatccgac gatggttgcg    720
atgacgcaga tcaccaagaa gatgcttgcc agcaaggaga aggccgagga gctgtaccca    780
gtgaagccgt ggaactgccg caagttcctg gtgctgtcca tcgggacggg gtcgacgtcg    840
gagcagggcc tgtacacggc gcggcagtgc ttgcggtggg catctgccg gtggatccgg    900 aacaacggca tggcccccat catcgacatc ttcatggcgg cgagctcgga cctggtggac    960
atccacgtcg ccgcgatgtt ccagtcgctc acacagcgacg gcgactacct gcgcatccag   1020
gacaactcgc tgcacggcgc cgcggccacc gtggacgcgg cgacgccgga gaacatgcgg   1080
acgctcgtcg ggatcgggga gcggatgctg gcgcagcggg tgtccagggt caacgtggag   1140
acagggaggt acgaaccggt gcctggggaa ggaagcaacg ctgatgcgct cgctgggatc   1200
gcaaggcagc tctcggagga gaggaggaca aggctcgcgc gccgcacctc cgccatcgtc   1260
agctccggtg gtgcctctag acgtacgtgt gcctcaaagg tctccaatgt ctaa         1314
```

<210> SEQ ID NO 12
<211> LENGTH: 437
<212> TYPE: PRT
<213> ORGANISM: Artificial Sequence
<220> FEATURE:
<223> OTHER INFORMATION: amino acid sequence of mutated Sorghum bicolor phospholipase S291L

<400> SEQUENCE: 12

```
Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Ile Arg Gly Leu Ile
        35                  40                  45

Pro Gly Thr Ile Leu Ala Phe Leu Glu Ala Arg Leu Gln Glu Leu Asp
    50                  55                  60

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
                85                  90                  95

Arg Arg Pro Leu Tyr Ala Ala Lys Asp Ile Asn Gln Phe Tyr Met Glu
            100                 105                 110

Asn Cys Pro Arg Ile Phe Pro Gln Lys Ser Ser Arg Leu Ala Ala Ala
        115                 120                 125

Met Ser Ala Leu Arg Lys Pro Arg Tyr Asn Gly Lys Cys Leu Arg Asn
    130                 135                 140
```

Leu Ile Met Ser Met Leu Gly Glu Thr Arg Val Ser Asp Thr Leu Thr
145                 150                 155                 160

Asn Val Ile Ile Pro Thr Phe Asp Val Arg Leu Leu Gln Pro Ile Ile
            165                 170                 175

Phe Ser Thr Tyr Asp Ala Lys Ser Met Pro Leu Lys Asn Ala Leu Leu
        180                 185                 190

Ser Asp Val Cys Ile Gly Thr Ser Ala Ala Pro Thr Tyr Leu Pro Ala
        195                 200                 205

His Tyr Phe Gln Thr Lys Asp Ala Gly Ser Gly Lys Glu Arg Glu Tyr
    210                 215                 220

Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
                245                 250                 255

Glu Leu Tyr Pro Val Lys Pro Trp Asn Cys Arg Lys Phe Leu Val Leu
            260                 265                 270

Ser Ile Gly Thr Gly Ser Thr Ser Glu Gln Gly Leu Tyr Thr Ala Arg
        275                 280                 285

Gln Cys Leu Arg Trp Gly Ile Cys Arg Trp Ile Arg Asn Asn Gly Met
    290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Ala Thr Val Asp
            340                 345                 350

Ala Ala Thr Pro Glu Asn Met Arg Thr Leu Val Gly Ile Gly Glu Arg
        355                 360                 365

Met Leu Ala Gln Arg Val Ser Arg Val Asn Val Glu Thr Gly Arg Tyr
    370                 375                 380

Glu Pro Val Pro Gly Glu Gly Ser Asn Ala Asp Ala Leu Ala Gly Ile
385                 390                 395                 400

Ala Arg Gln Leu Ser Glu Glu Arg Arg Thr Arg Leu Ala Arg Arg Thr
                405                 410                 415

Ser Ala Ile Val Ser Ser Gly Gly Ala Ser Arg Arg Thr Cys Ala Ser
            420                 425                 430

Lys Val Ser Asn Val
        435

<210> SEQ ID NO 13
<211> LENGTH: 2031
<212> TYPE: DNA
<213> ORGANISM: Artificial Sequence
<220> FEATURE:
<223> OTHER INFORMATION: genomic DNA of mutated Sorghum bicolor
      phospholipase Q372stop

<400> SEQUENCE: 13
acgcagtgcc tatatacaca agccaccatc tgtcgttgcc tcctcctcct cagctcatca      60
ctagtcacac gtacacccgc aatcgattga aaatttatcg cgttcgtcca acaatacca     120 gagctcgacg atcatcttaa ttgttggatc gatctgaata atctttcttc attcgtggcc     180
tcgacgagta agtaggtagc tcatttgatc gatcaaccgc gagtgtgtgc ttgatcgaag     240
gcggcaatgg cgacctacta ctcttcgcgg cgtccatgca acgcctgcag cacgaaggcg     300

```
atggccggga gcgtggtcgg cgagcccgtc gtgctggggc agagggtgac ggtgctgacg      360
gtggacggcg gcggcatccg tggtctcatc cccggaacca tccttgcctt cctcgaggcc      420
cggctgcagg agctggacgg gccggaggtt aggctcgcgg actacttcga ctacatcgcc      480
gggacgagca ccggcgggct catcaccgcc atgctcaccg cgcccggcaa ggacaggcgg      540
cctctctacg ctgccaagga catcaaccaa ttctacatgg agaattgccc tcgcatcttc      600
cctcaaaagt gagtccgatc atcccggccg gcgccattg ttggcctcgc attattgatc       660
gatcatgcat gcatgcatgc atgtgatgtg taggagcagc aggcttgcgg ccgccatgtc      720
cgcgctgagg aagccaaggt acaacggcaa gtgcctccgt aacctgatca tgagcatgct      780
cggcgagacg agggtgagcg acacgctcac caacgtcatc atccctacct cgacgtcag      840 gctgctgcag cccatcatct ctccaccta cgacgtacgt acgccgccgg ccgccgtcgt       900
catgaataat caatcagctg tacattattg cacatggctg catgcctact gaacatgttt      960
aatttgcagg ccaagagcat gcctctgaag aacgcgctgc tctccgacgt gtgcatcggc      1020
acgtccgccg cgccgaccta cctcccggcg cactacttcc agaccaagga cgccggcagt      1080
ggcaaggaac gcgagtacaa cctcatcgac ggcggtgtcg ccgccaacaa tccggtaatt      1140
aattaactga aaacgaacga acgcaattcc atatccattg tccagaagat cgatgctaat      1200
tgttgcttag gcacgtcgtt gccgccggcc gattgcattg cacttgcaca tgcgtagacg      1260
atggttgcga tgacgcagat caccaagaag atgcttgcca gcaaggagaa ggccgaggag      1320
ctgtacccag tgaagccgtg gaactgccgc aagttcctgg tgctgtccat cgggacgggg      1380
tcgacgtcgg agcagggcct gtacacgcgc cggcagtgct cgcggtgggg catctgccgg      1440
tggatccgga caacggcat ggcccccatc atcgacatct tcatggcggc gagctcggac       1500
ctggtggaca tccacgtcgc cgcgatgttc cagtcgctcc acagcgacgg cgactacctg      1560
cgcatccagg acaactcgct gcacggcgcc gcggccaccg tggacgcggc gacgccggag      1620
aacatgcgga cgctcgtcgg gatcggggag cggatgctgg cgtagcgggt gtccagggtc      1680
aacgtggaga cagggaggta cgaaccggtg cctggggaag gaagcaacgc tgatgcgctc      1740
gctgggatcg caaggcagct ctcggaggag aggaggacaa ggctcgcgcg ccgcaccctcc     1800 gccatcgtca gctccggtgg tgcctctaga cgtacgtgtg cctcaaaggt ctccaatgtc      1860
taagagaagt gaatttgttg cctgattaaa atcttaatta attaattctg tgggctgtgg      1920
ctcaaataaa actatatcat taaaaaaccc gccatgaact agttctagga aaatacgcat      1980
ggttttagaa agaaaaacat aaactaattc taacaaaatg tacacacctc t               2031
```

<210> SEQ ID NO 14
<211> LENGTH: 1116
<212> TYPE: DNA
<213> ORGANISM: Artificial Sequence
<220> FEATURE:
<223> OTHER INFORMATION: cDNA of Sorghum bicolor phospholipase mutant
      Q372stop

<400> SEQUENCE: 14

```
atggcgacct actactcttc gcggcgtcca tgcaacgcct gcagcacgaa ggcgatggcc       60
gggagcgtgg tcggcgagcc cgtcgtgctg ggcagaggg tgacggtgct gacggtggac        120
ggcggcggca tccgtggtct catccccgga accatccttg ccttcctcga ggcccggctg      180
caggagctgg acgggccgga ggttaggctc gcggactact tcgactacat cgccgggacg      240
agcaccggcg ggctcatcac cgccatgctc accgcgcccg gcaaggacag gcggcctctc      300
```

```
tacgctgcca aggacatcaa ccaattctac atggagaatt gccctcgcat cttccctcaa      360
aagagcagca ggcttgcggc cgccatgtcc gcgctgagga agccaaggta caacggcaag      420
tgcctccgta acctgatcat gagcatgctc ggcgagacga gggtgagcga cacgctcacc      480
aacgtcatca tccctacctt cgacgtcagg ctgctgcagc ccatcatctt ctccacctac      540
gacgccaaga gcatgcctct gaagaacgcg ctgctctccg acgtgtgcat cggcacgtcc      600
gccgcgccga cctacctccc ggcgcactac ttccagacca aggacgccgg cagtggcaag      660
gaacgcgagt acaacctcat cgacggcggt gtcgccgcca caatccgac gatggttgcg       720 atgacgcaga tcaccaagaa gatgcttgcc agcaaggaga aggccgagga gctgtaccca      780
gtgaagccgt ggaactgccg caagttcctg gtgctgtcca tcgggacggg gtcgacgtcg      840
gagcagggcc tgtacacggc gcggcagtgc tcgcggtggg gcatctgccg gtggatccgg      900
aacaacggca tggcccccat catcgacatc ttcatggcgg cgagctcgga cctggtggac      960
atccacgtcg ccgcgatgtt ccagtcgctc cacagcgacg cgactacct gcgcatccag      1020 gacaactcgc tgcacggcgc cgcggccacc gtggacgcgg cgacgccgga gaacatgcgg     1080
acgctcgtcg ggatcgggga gcggatgctg gcgtag                                1116
```

<210> SEQ ID NO 15
<211> LENGTH: 371
<212> TYPE: PRT
<213> ORGANISM: Artificial Sequence
<220> FEATURE:
<223> OTHER INFORMATION: amino acid sequence of mutated Sorghum bicolor
      phospholipase Q372stop

<400> SEQUENCE: 15

```
Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Ile Arg Gly Leu Ile
        35                  40                  45

Pro Gly Thr Ile Leu Ala Phe Leu Glu Ala Arg Leu Gln Glu Leu Asp
    50                  55                  60

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
                85                  90                  95

Arg Arg Pro Leu Tyr Ala Ala Lys Asp Ile Asn Gln Phe Tyr Met Glu
            100                 105                 110

Asn Cys Pro Arg Ile Phe Pro Gln Lys Ser Ser Arg Leu Ala Ala Ala
        115                 120                 125

Met Ser Ala Leu Arg Lys Pro Arg Tyr Asn Gly Lys Cys Leu Arg Asn
    130                 135                 140

Leu Ile Met Ser Met Leu Gly Glu Thr Arg Val Ser Asp Thr Leu Thr
145                 150                 155                 160

Asn Val Ile Ile Pro Thr Phe Asp Val Arg Leu Leu Gln Pro Ile Ile
                165                 170                 175

Phe Ser Thr Tyr Asp Ala Lys Ser Met Pro Leu Lys Asn Ala Leu Leu
            180                 185                 190

Ser Asp Val Cys Ile Gly Thr Ser Ala Ala Pro Thr Tyr Leu Pro Ala
        195                 200                 205
```

```
His Tyr Phe Gln Thr Lys Asp Ala Gly Ser Gly Lys Glu Arg Glu Tyr
    210                 215                 220

Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
                245                 250                 255

Glu Leu Tyr Pro Val Lys Pro Trp Asn Cys Arg Lys Phe Leu Val Leu
            260                 265                 270

Ser Ile Gly Thr Gly Ser Thr Ser Glu Gln Gly Leu Tyr Thr Ala Arg
        275                 280                 285

Gln Cys Ser Arg Trp Gly Ile Cys Arg Trp Ile Arg Asn Asn Gly Met
    290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Ala Thr Val Asp
            340                 345                 350

Ala Ala Thr Pro Glu Asn Met Arg Thr Leu Val Gly Ile Gly Glu Arg
        355                 360                 365

Met Leu Ala
    370

<210> SEQ ID NO 16
<211> LENGTH: 2979
<212> TYPE: DNA
<213> ORGANISM: Helianthus annuus

<400> SEQUENCE: 16
atgaataaca tcaatcttgt aatagtttcg cttgtaatcg cgattgtagc catccaaccc      60
cttgcgcaag agcaaaccga tgtaggtgag gcaaatttcg tcactgttct tagcatcgat     120
ggtgggggtg ttcgtggcat tgttcccgcc accttgcttg cttttcttga atccaaaatt     180
caggtactcg aacttaaaat gcacatgtgc atcatattac aagctgtaac ttattattga     240
aatgtgccgt ctcttcggat aggaaataga tgggccagat gcacgaattg cggattattt     300
tgatgtaata gccggaacaa gcacaggagg gctgatgaca actatgcttg cagctcctaa     360
tgagaaaaat cgtcccatgt cgccgcaaaa agacattacc aacttctact tcaacattc     420 gcctaggatc ttccctaaaa tagggtaaac tctaactagt ttccggatct ataagatcat     480
cattaaatac aagtttcatt ttcttttttcg aatcaaatac agacacacat ttgatgaggc     540
gcaaccttat ccttctcaaa acgaagcctg cgaaatgggg tattctccta caaagacttt     600
tgtaattcat gttctagtgg gtgtttggat gtgcgtttta aaactgatta ttatttacat     660
gtagtttctg aagaaaataa aacagttatt caaacacttt tgttaataa ttctactaga      720 aaaaaaaaat ccttgtcagg aaattaatta aaaaaaagtt accatctatt aaagttcttt     780
cttactaatc aaaagttttt aaattttatt atcatgttat tataactaaa catacacatc     840
caaacactat ctcataccac atgattacac aagtctatta tttgaatatg ctaacttagt     900
attttcatat aataagtttt taaaacgcca catccaaaac ccttgattct tattttacat     960
tgtgtagcta aaacagtgtt tatacataaa acaatcagt tatataaatc aaagcattat     1020
ttaactaaag taagctcggt tcaaactcga taagagaatt aatatatacg agtcgagttc     1080
ctgttgacca gatttcgcta gtgttaagtt tcgagttcaa aattgtatat gaacttgaac     1140
```

```
ctgtgtatca tcatacttga catttaaacc ataatgttgt tgaataaata aagtgatttt     1200
attttgtagt cggaccaaat tcatgaattc ggtagtaacc gtacttggtg aggccaccgg     1260
accaaagtat gatggtaaat atcttcgagc catggcaaag atgatgttaa aaaacctcac     1320
tattaaagat acgttgacga atgttgtcat acctgctttc gacattaggc ggcttcaacc     1380
tgttatcttc tcctctgctc aagtaattaa actcgttttt tatatttata gcagttctct     1440
atttaaaatt gattgtgtat cataaaatgg tttctgtttg atacgtttag ggaaaagagg     1500
tcgcgtggaa aaatgctttg ctagcagacg tatgcattag taccgcggcg gcaccaacat     1560
ttttcccgcc atactatttt gagactagag acgtcgatgg aaccaagcac acttttgatc     1620
taatcgatgg cggggtagct gcaaacaatc cggtagttac atttcaacaa tattgagttt     1680
gcattttatt tttaggacaa gtagtcacat tagggtgaag ggtgtgttca agctcatccc     1740
gaaggtggga gcggtgttcc cactcgtacc tcatggcgca ttttcttctt tgttgcagct     1800
ccaattttaa aaagccaccc cgccttttcc attccatagc gccacgtcaa ctgggaaatg     1860
gtgttcccac tggtattgga gatttggagg cgctacgcca cctctgtcat cccgaagcca     1920
caccctccac ccttaggagt gttatcggtt cagttttcgg tttatacagt ttaaaggttt     1980
ttttttggtt gaaaccaaaa accgaactga actgaacgga attcgggtag ttcacaactg     2040
aaccaaaaac tgaatccata ttcggttttc tgtttgaccg aataatcatt atttgttatt     2100
tgattgtgcg aggttaaata agattgagca aaaattgtaa ttaattggat ttggctaaat     2160
gacaatttaa ataaccgtta tttgttatcc gattcaaacc gaacacccaa ctcgatttgg     2220
tttaataccg aaccgacaac cggatacgta attcagttcg ctattaaaag gttcgggttt     2280
ggtagggttt aacccatttg aaatcgaatc ttcagagaaa gggttcgcta atgtcaccca     2340
cataaccaaa gaaatcttgt ttaaatgtta atggcagaca catttggcta tcacacatat     2400
aaccaaagaa gcggtgatgg ggaaatacag gttctctggc ccggaggttt tcgacggaag     2460
acggatgctt gtgctttcac tcggcactgg tacgcagacg tacaatgact tatatactgc     2520
acaaaaggct gcaaaatggg ggttgcttag ttggatcttt accatggta ctgcgccaat     2580 cctccgcatt tttggtgatg ccatgtcaga tatggtcgac atccatgtgt caactatatt     2640
ccaatcgttg caagtcgaaa aaaactatct gcgtattcag gtataactaa gaacatataa     2700
atataatgtt gtataggtta catgtttagt aacaaggagt tttttatgg gcaggaagat     2760 aacttgaaag gggaagcaac tgcaatggat atttcatcac ctgagaacat gagggcgcta     2820
gaggacattg caagaaatt gttgaagaaa ccgttgtcga gattggatgt ggagacaggc     2880
aagcttgaac cagttaaagg agaaggtacg aatgctgatg cattagcacg tttcgccact     2940
ttgctttgtg ccgaacgaaa gcgccgcaat ccagcttaa                           2979
```

<210> SEQ ID NO 17
<211> LENGTH: 1305
<212> TYPE: DNA
<213> ORGANISM: Artificial Sequence
<220> FEATURE:
<223> OTHER INFORMATION: cDNA of Helianthus annuus phospholipase

<400> SEQUENCE: 17

```
atgaataaca tcaatcttgt aatagtttcg cttgtaatcg cgattgtagc catccaaccc       60
cttgcgcaag agcaaaccga tgtaggtgag gcaaatttcg tcactgttct tagcatcgat      120
ggtgggggtg ttcgtggcat tgttcccgcc accttgcttg cttttcttga atccaaaatt      180
```

-continued

```
caggaaatag atgggccaga tgcacgaatt gcggattatt ttgatgtaat agccggaaca      240
agcacaggag ggctgatgac aactatgctt gcagctccta atgagaaaaa tcgtcccatg      300
ttcgccgcaa aagacattac caacttctac tttcaacatt cgcctaggat cttccctaaa      360
ataggcacac catttgatga ggcgcaacct tatccttctc aaaacgaagc ctgcgaaatg      420
ggtcggacca aattcatgaa ttcggtagta accgtacttg gtgaggccac cggaccaaag      480
tatgatggta aatatcttcg agccatggca aagatgatgt taaaaaacct cactattaaa      540
gatacgttga cgaatattgt catacctgct ttcgacatca ggcggcttca acctgttatc      600
ttctcctctg ctcaaggaaa agaggtcgcg tggaaaaatg ctttgctagc agacgtatgc      660
attagtaccg cggcggcacc aacgttttc cgccatact attttgagac tagagatgtc        720
gatggaacca agcacacttt tgatctaatc gatggcgggg tagctgcaaa caatccgaca      780
catttggcta tcacacatat aaccaaagaa gcggtgatgg ggaaatacag gttctctggc      840
ccggaggttt tcgacggcag acggatgctt gtgctttcac tcggcactgg tacgcagacg      900
tacaatgact tatacactgc acaaaaggct gcaaaatggg ggttgcttag ttggatcttt      960
accaatggta ctgcgccaat cctccgcatt tttggtgatg ccatgtcaga tatggtcgac     1020
atccatgtgt caactatatt ccaatcgttg caagtcgaaa aaaactatct gcgtattcag     1080
gaagataact tgaaggggga agcaactgca atggatattt catcacccga aacatgagg      1140 gcgctagagg acattggcaa gaaattgttg aagaaaccgt tgtcgagatt ggatgtggag     1200
acaggcaagc ttgaaccagt taaggagaa ggtacgaatg ctgatgcatt agcacgtttc      1260
gccactttgc tttgtgccga acgaaagcgc cgcaatccag cttaa                     1305
```

<210> SEQ ID NO 18
<211> LENGTH: 434
<212> TYPE: PRT
<213> ORGANISM: Helianthus annuus

<400> SEQUENCE: 18

```
Met Asn Asn Ile Asn Leu Val Ile Val Ser Leu Val Ile Ala Ile Val
1               5                   10                  15

Ala Ile Gln Pro Leu Ala Gln Glu Gln Thr Asp Val Gly Glu Ala Asn
            20                  25                  30

Phe Val Thr Val Leu Ser Ile Asp Gly Gly Val Arg Gly Ile Val
        35                  40                  45

Pro Ala Thr Leu Leu Ala Phe Leu Glu Ser Lys Ile Gln Glu Ile Asp
    50                  55                  60

Gly Pro Asp Ala Arg Ile Ala Asp Tyr Phe Asp Val Ile Ala Gly Thr
65                  70                  75                  80

Ser Thr Gly Gly Leu Met Thr Thr Met Leu Ala Ala Pro Asn Glu Lys
                85                  90                  95

Asn Arg Pro Met Phe Ala Ala Lys Asp Ile Thr Asn Phe Tyr Phe Gln
            100                 105                 110

His Ser Pro Arg Ile Phe Pro Lys Ile Gly His Thr Phe Asp Glu Ala
        115                 120                 125

Gln Pro Tyr Pro Ser Gln Asn Glu Ala Cys Glu Met Gly Arg Thr Lys
    130                 135                 140

Phe Met Asn Ser Val Val Thr Val Leu Gly Glu Ala Thr Gly Pro Lys
145                 150                 155                 160

Tyr Asp Gly Lys Tyr Leu Arg Ala Met Ala Lys Met Met Leu Lys Asn
                165                 170                 175
```

```
Leu Thr Ile Lys Asp Thr Leu Thr Asn Ile Val Ile Pro Ala Phe Asp
            180                 185                 190

Ile Arg Arg Leu Gln Pro Val Ile Phe Ser Ser Ala Gln Gly Lys Glu
        195                 200                 205

Val Ala Trp Lys Asn Ala Leu Leu Ala Asp Val Cys Ile Ser Thr Ala
    210                 215                 220

Ala Ala Pro Thr Phe Phe Pro Pro Tyr Tyr Phe Glu Thr Arg Asp Val
225                 230                 235                 240

Asp Gly Thr Lys His Thr Phe Asp Leu Ile Asp Gly Val Ala Ala
                245                 250                 255

Asn Asn Pro Thr His Leu Ala Ile Thr His Ile Thr Lys Glu Ala Val
            260                 265                 270

Met Gly Lys Tyr Arg Phe Ser Gly Pro Glu Val Phe Asp Gly Arg Arg
        275                 280                 285

Met Leu Val Leu Ser Leu Gly Thr Gly Thr Gln Thr Tyr Asn Asp Leu
    290                 295                 300

Tyr Thr Ala Gln Lys Ala Ala Lys Trp Gly Leu Leu Ser Trp Ile Phe
305                 310                 315                 320

Thr Asn Gly Thr Ala Pro Ile Leu Arg Ile Phe Gly Asp Ala Met Ser
                325                 330                 335

Asp Met Val Asp Ile His Val Ser Thr Ile Phe Gln Ser Leu Gln Val
            340                 345                 350

Glu Lys Asn Tyr Leu Arg Ile Gln Glu Asp Asn Leu Lys Gly Glu Ala
        355                 360                 365

Thr Ala Met Asp Ile Ser Ser Pro Glu Asn Met Arg Ala Leu Glu Asp
    370                 375                 380

Ile Gly Lys Lys Leu Leu Lys Lys Pro Leu Ser Arg Leu Asp Val Glu
385                 390                 395                 400

Thr Gly Lys Leu Glu Pro Val Lys Gly Glu Gly Thr Asn Ala Asp Ala
                405                 410                 415

Leu Ala Arg Phe Ala Thr Leu Leu Cys Ala Glu Arg Lys Arg Arg Asn
        420                 425                 430

Pro Ala

<210> SEQ ID NO 19
<211> LENGTH: 1531
<212> TYPE: DNA
<213> ORGANISM: Hordeum vulgare

<400> SEQUENCE: 19
atggcaagct actggtgccg gcgaccgtgc gagtcgtgca gcacgagggc gatggcgggc      60
agcgtggtcg gccagccggt ggcgccgggg cagagggtga cggtgctgac catcgacggc     120
ggcggcatcc gcggcctcat cccgggcacc atcctcgcct tcctcgaggc caggctgcag     180
gagctggacg gccggacgc gcgcctggcc gactacttcg actgcatcgc cggcaccagc     240
accggcgggc tcatcaccgc catgctcacc gcgcccggcc aggacggccg cccgctcttc     300
gccgccaagg acgtcaaccg cttctacctc gacaacgggc cctacatctt cccccaaagg     360
cgagagcacg agcgatctca tggccatgga tcatgccagc tgaaccggtg attgatgtgt     420
gaattgtgtt gagctgtgcc aggaggtgcg cgctcgccgc ggtgaccgcg tcgctgaggc     480
ggccgaggta cagcggcaag tacctgcacg gcaagatcag gagcatgctg gcgagacga     540 ggctgtgcga cgcgctcacc gacgtcgtca tccccacctt cgacgtcaag cttctccagc     600
ccatcatctt ctccacatac gacgtatgct aatttacgcc attgatcaga tagatccatc     660
```

-continued

```
ctccttggat cagacagaca tggggctaaa atcgttgaag gatcatgcgt gcaggccagg      720
aacatgcccc tgaagaacgc gcggcttgcc gacatctgca tcggcacctc cgccgccccg      780
acctacctcc cggcgcacca cttccacacc caagacgaca cggtaagga gcgcgagtac       840 aacctcatcg acggcggcgt cgccgccaac aatccggtaa ccaaccaatc aagcgtccat      900
cagtcatcac atattcagat acgctgcccg agcacactga tgaactgagt tgtgagagat      960
gcagacgatg gtgaccatga cgcagatcac caagaagatg atggtcaagg acagggagga     1020
gctgtacccg gtgaagccgt cggactgcgg caagttcctg gtgctgtcca tcgggaccgg     1080
ctcgacgtcg gaccaggggc tgtacacggc caagcagtgc tcccagtggg gcatcatccg     1140
ctggctgcgc aacaagggca tggcgcccat catcgacatc ttcatggcgg ccagctccga     1200
cctcgtcgac atccacgccg ccgtgctctt ccagtcgctg cacagcgacg gtaactacct     1260
ccgcatccag acaactcgc tccacggccc agccgcgacg gtggacgccg ccacgcccga      1320
gaacatggcg gagctcctca ggatcggcga gcggatgttg gcacagaggg tgtccagggt     1380
gaacgtcgag accgggaggt acgaggagat acggggcgcc gggagcaacg ccgacgcgct     1440
cgccggcttc gccaaacagc tctccgacga ggaggaggaca aggctcggcc gccggcgcgt    1500
tggcgccggc cgtctgaaat ccagacgctg a                                    1531
```

<210> SEQ ID NO 20
<211> LENGTH: 1269
<212> TYPE: DNA
<213> ORGANISM: Artificial Sequence
<220> FEATURE:
<223> OTHER INFORMATION: cDNA of Hordeum vulgare phospholipase

<400> SEQUENCE: 20

```
atggcaagct actggtgccg cgaccgtgc gagtcgtgca gcacgagggc gatggcgggc       60
agcgtggtcg ccagccggt ggcgccgggg cagagggtga cggtgctgac catcgacggc      120
ggcggcatcc gcggcctcat cccgggcacc atcctcgcct cctcgaggc caggctgcag      180 gagctggacg ggccggacgc gcgcctggcc gactacttcg actgcatcgc cggcaccagc     240
accggcgggc tcatcaccgc catgctcacc gcgcccggcc aggacggccg cccgctcttc     300
gccgccaagg acgtcaaccg cttctacctc gacaacgggc cctacatctt cccccaaagg     360
aggtgcgcgc tcgccgcggt gaccgcgtcg ctgaggcggc cgaggtacag cggcaagtac     420
ctgcacggca agatcaggag catgctgggc gagacgaggc tgtgcgacgc gctccaccgac    480 gtcgtcatcc ccaccttcga cgtcaagctt ctccagccca tcatcttctc cacatacgac     540
gccaggaaca tgcccctgaa gaacgcgcgg cttgccgaca tctgcatcgg cacctccgcc     600
gccccgacct acctcccggc gcaccacttc cacacccaag acgacaacgg taaggagcgc     660
gagtacaacc tcatcgacgg cggcgtcgcc gccaacaatc cgacgatggt gaccatgacg     720
cagatcacca gaagatgat ggtcaaggac agggaggagc tgtacccggt gaagccgtcg      780
gactgcggca agttcctggt gctgtccatc gggaccggct cgacgtcgga ccaggggctg     840
tacacggcca agcagtgctc ccagtggggc atcatccgct ggctgcgcaa caagggcatg     900
gcgcccatca tcgacatctt catggcggcc agctccgacc tcgtcgacat ccacgccgcc     960
gtgctcttcc agtcgctgca cagcgacggt aactacctcc gcatccagga caactcgctc    1020 cacgcccag ccgcgacggt ggacgccgcc acgcccgaga catggcggga gctcctcagg     1080
atcggcgagc ggatgttggc acagagggtg tccagggtga acgtcgagac cgggaggtac    1140
```

```
gaggagatac ggggcgccgg gagcaacgcc gacgcgctcg ccggcttcgc caaacagctc       1200
tccgacgaga ggaggacaag gctcggccgc cggcgcgttg gcgccggccg tctgaaatcc       1260
agacgctga                                                                1269
```

<210> SEQ ID NO 21
<211> LENGTH: 422
<212> TYPE: PRT
<213> ORGANISM: Hordeum vulgare

<400> SEQUENCE: 21

```
Met Ala Ser Tyr Trp Cys Arg Arg Pro Cys Glu Ser Cys Ser Thr Arg
1               5                   10                  15

Ala Met Ala Gly Ser Val Val Gly Gln Pro Val Ala Pro Gly Gln Arg
            20                  25                  30

Val Thr Val Leu Thr Ile Asp Gly Gly Ile Arg Gly Leu Ile Pro
        35                  40                  45

Gly Thr Ile Leu Ala Phe Leu Glu Ala Arg Leu Gln Glu Leu Asp Gly
    50                  55                  60

Pro Asp Ala Arg Leu Ala Asp Tyr Phe Asp Cys Ile Ala Gly Thr Ser
65                  70                  75                  80

Thr Gly Gly Leu Ile Thr Ala Met Leu Thr Ala Pro Gly Gln Asp Gly
                85                  90                  95

Arg Pro Leu Phe Ala Ala Lys Asp Val Asn Arg Phe Tyr Leu Asp Asn
            100                 105                 110

Gly Pro Tyr Ile Phe Pro Gln Arg Arg Cys Ala Leu Ala Ala Val Thr
        115                 120                 125

Ala Ser Leu Arg Arg Pro Arg Tyr Ser Gly Lys Tyr Leu His Gly Lys
    130                 135                 140

Ile Arg Ser Met Leu Gly Glu Thr Arg Leu Cys Asp Ala Leu Thr Asp
145                 150                 155                 160

Val Val Ile Pro Thr Phe Asp Val Lys Leu Leu Gln Pro Ile Ile Phe
                165                 170                 175

Ser Thr Tyr Asp Ala Arg Asn Met Pro Leu Lys Asn Ala Arg Leu Ala
            180                 185                 190

Asp Ile Cys Ile Gly Thr Ser Ala Ala Pro Thr Tyr Leu Pro Ala His
        195                 200                 205

His Phe His Thr Gln Asp Asp Asn Gly Lys Glu Arg Glu Tyr Asn Leu
    210                 215                 220

Ile Asp Gly Gly Val Ala Ala Asn Asn Pro Thr Met Val Thr Met Thr
225                 230                 235                 240

Gln Ile Thr Lys Lys Met Met Val Lys Asp Arg Glu Glu Leu Tyr Pro
                245                 250                 255

Val Lys Pro Ser Asp Cys Gly Lys Phe Leu Val Leu Ser Ile Gly Thr
            260                 265                 270

Gly Ser Thr Ser Asp Gln Gly Leu Tyr Thr Ala Lys Gln Cys Ser Gln
        275                 280                 285

Trp Gly Ile Ile Arg Trp Leu Arg Asn Lys Gly Met Ala Pro Ile Ile
    290                 295                 300

Asp Ile Phe Met Ala Ala Ser Ser Asp Leu Val Asp Ile His Ala Ala
305                 310                 315                 320

Val Leu Phe Gln Ser Leu His Ser Asp Gly Asn Tyr Leu Arg Ile Gln
                325                 330                 335

Asp Asn Ser Leu His Gly Pro Ala Ala Thr Val Asp Ala Ala Thr Pro
            340                 345                 350
```

```
Glu Asn Met Ala Glu Leu Leu Arg Ile Gly Glu Arg Met Leu Ala Gln
            355                 360                 365
Arg Val Ser Arg Val Asn Val Glu Thr Gly Arg Tyr Glu Glu Ile Arg
        370                 375                 380
Gly Ala Gly Ser Asn Ala Asp Ala Leu Ala Gly Phe Ala Lys Gln Leu
385                 390                 395                 400
Ser Asp Glu Arg Arg Thr Arg Leu Gly Arg Arg Val Gly Ala Gly
                405                 410                 415
Arg Leu Lys Ser Arg Arg
            420

<210> SEQ ID NO 22
<211> LENGTH: 9001
<212> TYPE: DNA
<213> ORGANISM: Beta vulgaris
<220> FEATURE:
<221> NAME/KEY: misc_feature
<222> LOCATION: (2702)..(2702)
<223> OTHER INFORMATION: n is a, c, g, or t

<400> SEQUENCE: 22
```

| | | | | | |
|---|---|---|---|---|---|
| ttttccaaca | acataccgag | tagttttctc | caagtttaag | ttatttatgt | tattgtaatt | 60 |
| gtaatgtaag | agctagtaaa | gctcagttta | gtttctttgt | ttttagtatg | aatgtaccat | 120 |
| ttttagtatg | taattatgct | tttaattaat | gcaaaatttt | ccgttgtaaa | aaaaagtcta | 180 |
| catgtccctc | ttgcagagat | aaatgtaagg | gacattattg | cttagttctc | gactaattta | 240 |
| caataagttt | ataattggtt | atcatggttc | atgagtactc | ctgttcatag | aaggacaata | 300 |
| atttataaag | gtttcttagt | agcttccaat | gacggagctc | aatgaccctg | ttaattagct | 360 |
| aagtaataag | ttggccatta | gccaataaca | actgtattat | tagctagtaa | gttcattaga | 420 |
| tcgatataac | ttataagtct | aatgaatata | aatatgaata | agatggaact | gaaatgagtt | 480 |
| ttatatttga | aaaattagtg | gcatacgtgc | ttaaacgttt | ttttgattat | ggctagaaga | 540 |
| cttagaacga | agttggagga | attcttcatt | catataaatt | tatgctagat | aaactaatag | 600 |
| ccagtcaagt | caagtttatg | ttttttaaaaa | aaatcttatc | tcatgtagta | cgagaatctt | 660 |
| tattttataa | tttcgttata | ataaatatgc | atttcactcc | tttcaaatcg | ttagctacat | 720 |
| cacttctgca | accaagcaag | caagccataa | tatttaatca | caggttcttt | aatactatag | 780 |
| tctatatata | catgcaatcc | acttacatta | attatcatct | tattctccca | tcatcaagaa | 840 |
| aacacattac | aatccaaaga | aataaaacat | ggagaattct | agatctctgg | gtaaccctgt | 900 |
| tagccctaga | cccctaatc | atggtaatct | cataacaatt | ttaagtattg | atggggagg | 960 |
| cattagggga | ataatccctg | cagttatgct | tgaattcctt | gaatcacaac | tccaggtatg | 1020 |
| tacataatta | agaaatgatg | atatacgatc | atctttagta | ctcttgttaa | atgatttgac | 1080 |
| gtaagaaatc | atgtatatat | tatgcatgcc | ttactataat | attgcgtgca | tgttcataat | 1140 |
| cacaacagaa | gttagatggt | gaggaagcaa | gattggctga | ttattttgat | gttattgccg | 1200 |
| gaacgagcac | cggtggcctc | ataactgcca | tgttaaccgc | ccctaacgac | aaaactcggc | 1260 |
| cactctacgc | cgccaaggag | attactcctt | tttatcttga | gcattgtccg | aagatcttcc | 1320 |
| gccaaccaag | gtaaataaat | caaatttatc | atctatgtat | atcaggattg | gtaaattaga | 1380 |
| gaggatgaaa | aacccttaaa | tgcttggaac | tattaacgct | cgagttccaa | ttatgggcca | 1440 |
| ttgtctctta | taggtctcaa | ctattgattt | ttttctatag | caggcgcgga | tgtaagattt | 1500 |
| tgaatttgga | agggtcctaa | ctaaaccaaa | gaaataaatt | acaatgacca | tattaacata | 1560 |

```
taagaagttt agttttaaca ataagaaaac caacagttgg tcttgtaaga gaccgtctac    1620
ttttaattta aaagtaggcg cggcccaagc ccaatattaa gaagagaata gatcatattt    1680
cttaatatag tgactacttt aatctattta gtgaccattt taatctattt agtgaccagt    1740
ttaatctatt cattaataac attctttaat tcatttagtg actgatttaa tccatttagt    1800
gactagctta atccattttg taagactgac ggactatttt taaaaattgt tgttctaat     1860 tcaaaattta gaagggaaat aaaagaagga gaagagaatg gacgactagg atggtgcaag    1920
atacctaaaa aaagtgttag gttagagaga aattgaatgg gcttcttagg agaatgtagg    1980
tttgcattgt ctaattttat attaaaatta gaccgtctat tataataatt tgtggaaaac    2040
aaaactttat attatttgaa tcatgtatta gatataccct aattatattg atatcttaat    2100
gttatcttca ttttagtaa attcaacaga tttgatttgt acatccgtta acatatgcga    2160
cactaacatt tgatatcttc agttatatgt tcataatttt ttttttttaaa aagttggaca    2220 taaatttggt aaacgaaaat agagacaaat tcacaatttt acatagtaat attattttca    2280
agtatttgga aacaagcttg gtcaaactta atatagcaat accgtagaaa gtcaaattat    2340
tgaatttatt tgaaacaaaa ggagaataat cgttatatca caaaaaaaaa agtattaaaa    2400
ttagagctaa attaagagag attggtagca ttcaagataa tgaaatgatg attagatata    2460 aaaagaaaa gatgataaaa gagaaaagtt aagaacagg aagggcatgt tctcttcagc     2520
ataaaacagc tgaactgaac taacctgaat tgaactgatt ggagctgaac tgaactgaac    2580
tgaactgaac tgaattgaat ttaatttaat ttaattgtat tgaattaaat taaatttaat    2640
ttaatttaat tgaattgaat taaattgaat gtaataaata tataaataat atttaaacaa    2700
tnagtacagt tattataata ataattgtgc ccttctgaaa ttgttaaggc acgtcgtttg    2760
caagatttgt cctttttgcat taaaatttgg gtgcaaatcc tgcacaaatt gaaatatata    2820
gtattatctc tccactcatt tttatcttct tgtatcattt taggctcgac aataatgact    2880
ctgccagagg ggtagttgaa ccttcttata tcatcatcat aattcataat aataatttta    2940
ttatatatac tccctccgtt ccaaaatata gttctcgttt ctttttttta cgatgatttg    3000
tgcaagtaga atcaagtgg aataataaaa ttttttttgtt tatttaaata aatattgtat    3060
ggaaaaggat gattttagga gagaaaaatg gaaaataatt ggtgaaagag tattaattgt    3120 aatatttag ttgaataaat aacagaaaaa ccaaaatata gaagcaaat aaatgatggg     3180 acacgatctt tgtagacaaa ttacagaaaa atttggaaac gaatatggaa atgggaacta    3240
tattttggga cacccaaata gaaatgggaa ctatattttg ggacggaggg agtaatatta    3300
ataatcataa attattaata ataatagtaa taattaatga tactaatgat aattaataac    3360
cgaagatcgc gtgattattt tgttggagt tgtagtggga tatttggttc aatagggact     3420
ctaatgaagc tgctaagcgg gccgaaatac gatggaaagt accttcacaa tctagtaaag    3480
gaattgctcg gacaaagaag gttgcatcaa gcgttgacta atgtggttat cccaactttt    3540
gatatcaaga atcttcagcc tgttctcttt tctacttata tggtatgttg ttgaatttcc    3600
aatttattga agtacattat tattgtaccc ttggttatct tattcattag caaatactag    3660
cattcaaata gcatttatag tgatttgtca agaaaaaaaa taagtagagg aatcatagtt    3720
atcacttatt agaactacct cttttagaag aatatacttc ctctattttt ttagatggaa    3780
catttacctt tttggtgagt agattaaaat aatcatatgt tgtatttaaa aaacagaat     3840 tagtatatat cttcttttgt gtcatataat acacttgatc aatttaaaag ataacatgat    3900
```

```
tccaatattg actttttat acacataatt tcacatgtca aataatagaa aaaaagtcaa    3960
ctttgctgaa tttggagatg ataatacata gtttatgtgt tggttaagta atttcatact    4020
actacattga tagattatga aattgatcaa gaaaactaat caataattaa tgattataat    4080
gatctaggtc ccaattgcta aagaattgga cgtgttgctg tcagacatat gcataggcac    4140
gtctgcagct ccaacgttcc taccagcgca tcattttgaa aacaaagatg atcagggcaa    4200
tgtcaaagaa ttcaacctca ttgatggtgg tattgctgcc aataatcctg taagattatt    4260
tcttcatcca tgtttggatt ttctctccat ccctaaattt aatttgatta ggaattagtc    4320
attcttaata aaattatga atcatcaatt aaattatcta ataaaagta attcaaacat      4380 ttgttcgata taatgtactt atttttttta ttaaatttta atttttcagac atattccaaa    4440 tgtcgtccta caaagaaat tgcaaatcca tctaaaaact tcgtttgata catctaataa     4500
tgtatgttcg agtcaatcat taaattttca tatcaagata aatatcaaag taagatgttt    4560 caaacttta cttagtcgat taattctatt aattccagtc aatttaccat caacttcttc     4620
ggtcttccca aaacaaatgg aaaaatatat attcactgca tacgtgtctt tgtgttatat    4680
tcctatctct aaagtattta agtttttatg atattaggac atatatattc tctagtattt    4740
aatgagaaag atcgaaaagt tttcgtatat tcataaaacc ttaacaactg ctattcaaaa    4800
tatacgataa gtttcatcaa cattacccac taattaaatg taatttcact gtataagtac    4860
agtcattagt ggcaataagc gaagtgacaa aacaaatagt gaagagcaac ccgaatttct    4920
tcccgataaa ggccacggat cgtgaacggt tgctggtgat atcgttaggg actggatccg    4980
acaaggtaga gcagctctat aatgctaaaa gcgcagcaaa gtggggaatt atttcatggt    5040
tatttgacaa tggtaatact ccactacttg atgctttaaa tcaatcaaag ctgatatgg    5100 tcgatttcca caattctgtg gccttcaag catatggttc tcttgacaat tatcttcgca    5160
tccaagtaag ttattttat tatacggatt tggatgttta tgtacgtata tatacttctg    5220
ttaaaggttg ataagatgag agttacgcgc tcattttacc aaggatcttt ggtttcaatg    5280
gtaatttggg accggtcaga cccgtggctg cgggcctatc acggtcaaga attttttatt    5340
caggctcgca ccgtcacgag cctgcctaga tggctcgcga gccgaacact catttccttt    5400 gcttttagc ctaaaactgt caaaagtcca aaaaacgaca taaaacacgg gccagctcgc     5460
aggagccacg agcccagtcc gtggataaaa tcttgaaatt tcaggcccga cccaccattt    5520
ccccaaaccc gcgggccgag cccgtgaaca agctcatgcc ctgatgccca ggtctaggtc    5580
tgcctcgcac ggagccttca tcccgaagcc cattacaagc cagacaccca actccctaca    5640
acaccacatc aaccccttcca atccactcgc cttccctctt cactgctgcc ggctgccctc    5700
taggtttatc atttttttcta agctcttttg tctaagttaa atccactggt ttctttcatt    5760 ttcttttga tttaagttcg attaccaatg tttcttaac tttgcaactt ttggggagat      5820
accttattgt aatttgctct aatgaaagtt tcttatgctt ataataatgc tcaattgtct    5880
ttcttgatct agtaatctga gagttatcca gttttaaata gttagagcta gtttcactaa    5940
tggtggcaat aagggtgtgg caggggcga tgcttggttt tggactttgg taatggtggt      6000
aatgaaggga ggttacacag tgaggatggt ggttggtgta attggtgggg aaactcgggg    6060
tagagagata accctaaag gcgagattat gcttagtcaa tcgaaggtg tgcctatttt      6120 aagcggacca cctaaaggtc ggattattat aatcaatttt tcctaaataa attgcaattt    6180
gtggttggat ttctagtttg aaactaaatc tcaattgcaa gtctgcaacc gtatgaacta    6240
tgaaccattt tgaggttaat atatctatag attttttattt caaaaaaata taaaaatata    6300
```

```
ttatttcaaa aaggtccaag aatacgtctt ttaagagtgt ccaagaacat ctaaccacga    6360
gttatatatt tgtctattat gtggtgatca cttttcaag atttgaggtc tttaattagg     6420
ccttgatgat atagatttgt tagagaaaaa catttgcttg attaaaaaag gaaataaatg    6480
atatgacaaa tgactaattg actcatgtct aacctttaa atgtggtgtg atttaactcg    6540
acatttaata tgtggttggt ttgataaatt ttagcgagca cgctttatat aagtgtaact    6600
tatatatctt gtgcataagt ttagttattt attttttact ttattaaaca aaattgataa    6660
atatgatata gttaattaaa tatattactc tcataaatca agctacccta aatctgtaaa    6720
tgcaaattat attgcaggat gatacactaa agggagtatc agcatcagtc gatgtggcaa    6780
ccacagaaaa tttggcaaat cttgtcacaa ttggaaaggc actcttgaaa aagccagtat    6840
ccaggattaa tttcgatacg ggtagatatc aacctatccc taatggaggg accaatgagg    6900
aagccttaat taggtacttg atttaaataa atcattcata aagaatcacg ctcattgctt    6960
gtcaataaaa tatttatgtt tatgtttaat actaatgctt gttttctaat acttttaaca    7020
ctttactttc ttacatgaga tgccgagacg agtgtagagt aatttattgt gtaggtaact    7080
ttttgctcta tatgagtcac ttatataaaa gtgacatata tatggtaata agttacctgt    7140
aagacgaggt taactatttg ccataaatag gtcactttac ttatatagaa gtgactcatt    7200
taagattaaa attaagttac cttttatta aaattgaccc atattgattt gaaaagtgac    7260
ccatattgat ttgaaaagtg acccatttaa gctttaagtg aactgatgtg acaataaatt    7320
tattatacac ccggtgcaca taatacaaat tgtttaaatt atcaagggtt tgttggacaa    7380
aagtaattgt tagttgtaag cttctagcta tgagtttgtg agcttttaga tgcctaggta    7440
gtttctaact tttagttatg aaactagttg tctaaagtgt ttggtaataa taattattga    7500
cgaaatttta acatgtaaat aatatttaaa tttggcaact tttgataaaa gctaccgaaa    7560
agcttaatca tcttagattt tgaccaagac tactcaaaag ctaaaagtta tctaaaagtt    7620
acatccaaaa gctactttga ggaatattta acaattttt tcaaagacta aaagctatct    7680
taactacata aaaagtatgt caaaagttac accaaacatg tcctacattg accacgttat    7740
tctaacctac aaaactgact gggcaaacct gctactttgc aagaggtatc agtttattag    7800
ggtgtttcat cttacctacc taaacagtaa aagtaaatat ataaataaaa caaatattaa    7860
ttttatataa atattttatg agattagtat taatgtatat cctataatat caacattcaa    7920
aaaactttta cgaatagata aaagatata ttaagaatta aaattatgca aattcaaaag    7980
tcaattcaaa ttactcctat taaaaattgg cggtatatga tttaaacttt caaaaataag    8040
aaaattataa aattatgtca ctctttgtta ctactgaata catgtttgtc caattgacag    8100
gtttgcgaaa ctccttaccg aggaaaagag cagacgcgaa caatatcgga cgaaccgaag    8160
tgactaatat cacattttt aaacccatgt ttcaatggat actatgatta tatagtatat    8220
atatatgtat acaatacatc atgatctgga aaaaaactta cgctcgattt atgataaata    8280
aatttgtcaa accatgtagc tctcacaaaa tctgtaatat ttaatgaatt ttagtatgcg    8340
tagatatggc ctatgggcgt ggaatattta tccatgtaac tcatttatt ttacagctaa    8400 gtcattgcat tttaatctac gaatttctc ttttaatcaa taacctaaaa ataaatagtt    8460
tgtgcatcaa tttctctcta tttactctgt aagtatttgt tgttttctt tattgaacga    8520 taactacagt gccactccta tatatacaag agatcacttt ctaaacctag ggataactat    8580
acaagaagag aaactaaccg ttaaaatctt tctacgatca ataaaaggag gaatatataa    8640
```

```
tcacatgaaa gtgcgaaata atcaatacaa gtgagtttaa ttccctccgc cactctaact    8700
catttcccta ctctacactt aattctccca cgctatcaat cccattcatt tactccagta    8760
tcagatgcta gtaattcttc atagaatatg aaatatacta ggattatatt ttgcgtttgg    8820
atatagtttt ggtagaataa caattctact ctagttacgt tttctactat tattgggata    8880
tcctttagaa tgtaacctat aaaatatgat caataaaaac actcaaatca aggaagttta    8940
cgcaaatata gcctggtatc aaagctatac taatcttaaa gattattttt tccttcgatc    9000
c                                                                    9001

<210> SEQ ID NO 23
<211> LENGTH: 1224
<212> TYPE: DNA
<213> ORGANISM: Artificial Sequence
<220> FEATURE:
<223> OTHER INFORMATION: cDNA of Beta vulgaris phospholipase 1

<400> SEQUENCE: 23
atggagaatt ctagatctct gggtaaccct gttagcccta gacccctaa tcatggtaat      60 ctcataacaa ttttaagtat tgatggggga ggcattaggg gaataatccc tgcagttatg     120
cttgaattcc ttgaatcaca actccagaag ttagatggtg aggaagcaag attggctgat    180
tattttgatg ttattgccgg aacgagcacc ggtggcctca taactgccat gttaaccgcc    240
cctaacgaca aaactcggcc actctacgcc gccaaggaga ttactccttt ttatcttgag    300
cattgtccga agatcttccg ccaaccaagt gggatatttg gttcaatagg gactctaatg    360
aagctgctaa gcgggccgaa atacgatgga aagtaccttc acaatctagt aaaggaattg    420
ctcggacaaa gaaggttgca tcaagcgttg actaatgtgg ttatcccaac ttttgatatc    480
aagaatcttc agcctgttct cttttctact tatatggtcc caattgctaa gaattggac    540 gtgttgctgt cagacatatg cataggcacg tctgcagctc caacgttcct accagcgcat    600 catttttgaaa acaaagatga tcagggcaat gtcaaagaat tcaacctcat tgatggtggt    660
attgctgcca ataatccttc attagtggca ataagcgaag tgacaaaaca aatagtgaag    720
agcaacccga atttcttccc gataaaggcc acggatcgtg aacggttgct ggtgatatcg    780
ttagggactg gatccgacaa ggtagagcag ctctataatg ctaaaagcgc agcaaagtgg    840
ggaattattt catggttatt tgacaatggt aatactccac tacttgatgc ttttaatcaa    900
tcaaaggctg atatggtcga tttccacaat tctgtggcct tcaagcata tggttctctt    960 gacaattatc ttcgcatcca agatgataca ctaaagggag tatcagcatc agtcgatgtg   1020
gcaaccacag aaaatttggc aaatcttgtc acaattggaa aggcactctt gaaaaagcca   1080
gtatccagga ttaatttcga tacgggtaga tatcaaccta tccctaatgg agggaccaat   1140
gaggaagcct taattaggtt tgcgaaactc cttaccgagg aaaagagcag acgcgaacaa   1200
tatcggacga accgaagtga ctaa                                         1224

<210> SEQ ID NO 24
<211> LENGTH: 407
<212> TYPE: PRT
<213> ORGANISM: Beta vulgaris

<400> SEQUENCE: 24

Met Glu Asn Ser Arg Ser Leu Gly Asn Pro Val Ser Pro Arg Pro Pro
1               5                   10                  15

Asn His Gly Asn Leu Ile Thr Ile Leu Ser Ile Asp Gly Gly Gly Ile
            20                  25                  30
```

Arg Gly Ile Ile Pro Ala Val Met Leu Glu Phe Leu Glu Ser Gln Leu
        35                  40                  45

Gln Lys Leu Asp Gly Glu Ala Arg Leu Ala Asp Tyr Phe Asp Val
 50                  55                  60

Ile Ala Gly Thr Ser Thr Gly Leu Ile Thr Ala Met Leu Thr Ala
 65                  70                  75                  80

Pro Asn Asp Lys Thr Arg Pro Leu Tyr Ala Ala Lys Glu Ile Thr Pro
                85                  90                  95

Phe Tyr Leu Glu His Cys Pro Lys Ile Phe Arg Gln Pro Ser Gly Ile
                100                 105                 110

Phe Gly Ser Ile Gly Thr Leu Met Lys Leu Leu Ser Gly Pro Lys Tyr
                115                 120                 125

Asp Gly Lys Tyr Leu His Asn Leu Val Lys Glu Leu Leu Gly Gln Arg
                130                 135                 140

Arg Leu His Gln Ala Leu Thr Asn Val Ile Pro Thr Phe Asp Ile
145                 150                 155                 160

Lys Asn Leu Gln Pro Val Leu Phe Ser Thr Tyr Met Val Pro Ile Ala
                165                 170                 175

Lys Glu Leu Asp Val Leu Leu Ser Asp Ile Cys Ile Gly Thr Ser Ala
                180                 185                 190

Ala Pro Thr Phe Leu Pro Ala His His Phe Glu Asn Lys Asp Asp Gln
                195                 200                 205

Gly Asn Val Lys Glu Phe Asn Leu Ile Asp Gly Gly Ile Ala Ala Asn
                210                 215                 220

Asn Pro Ser Leu Val Ala Ile Ser Glu Val Thr Lys Gln Ile Val Lys
225                 230                 235                 240

Ser Asn Pro Asn Phe Phe Pro Ile Lys Ala Thr Asp Arg Glu Arg Leu
                245                 250                 255

Leu Val Ile Ser Leu Gly Thr Gly Ser Asp Lys Val Glu Gln Leu Tyr
                260                 265                 270

Asn Ala Lys Ser Ala Ala Lys Trp Gly Ile Ile Ser Trp Leu Phe Asp
                275                 280                 285

Asn Gly Asn Thr Pro Leu Leu Asp Ala Phe Asn Gln Ser Lys Ala Asp
                290                 295                 300

Met Val Asp Phe His Asn Ser Val Ala Phe Gln Ala Tyr Gly Ser Leu
305                 310                 315                 320

Asp Asn Tyr Leu Arg Ile Gln Asp Asp Thr Leu Lys Gly Val Ser Ala
                325                 330                 335

Ser Val Asp Val Ala Thr Thr Glu Asn Leu Ala Asn Leu Val Thr Ile
                340                 345                 350

Gly Lys Ala Leu Leu Lys Lys Pro Val Ser Arg Ile Asn Phe Asp Thr
                355                 360                 365

Gly Arg Tyr Gln Pro Ile Pro Asn Gly Gly Thr Asn Glu Glu Ala Leu
                370                 375                 380

Ile Arg Phe Ala Lys Leu Leu Thr Glu Glu Lys Ser Arg Arg Glu Gln
385                 390                 395                 400

Tyr Arg Thr Asn Arg Ser Asp
                405

<210> SEQ ID NO 25
<211> LENGTH: 14701
<212> TYPE: DNA
<213> ORGANISM: Beta vulgaris
<220> FEATURE:

<210> NAME/KEY: misc_feature
<222> LOCATION: (10783)..(10802)
<223> OTHER INFORMATION: n is a, c, g, or t

<400> SEQUENCE: 25

```
gagtgtggag tagttgcttt gtgcgagcgt gttttgtttg tgcgaacttc tgctgtcacg      60
ttttgtttgt ggaattgctg tcacgtttaa ttaccattca agtgtgatct ccttctagta     120
gattgtgatc ttgcttgtgg tatattggat ggtgtgagcc ccagacgtga ttttgttcgg     180
ttgatgcggt tgtgcatcgt ttctccaaaa ccctagttgg ttttggtgcgg ttacgcatcg    240
ttattttgat gggttatggt ggcccatcca agctattgtg ttggtgcggt tgtacatagt     300
tgatgcccta agtgacgaat tgaatcatga aggttggttg gttgtccata attcaaaaag    360
ggtatttctt ggttgtccat aattcaaaaa aggtatttct tggttgtccc taatccaaaa    420
tggtgtgtat tggttgtccc taatcttaaa agctggttat tgaaggcgtt gatttcacgt    480
cttattggtc tcctagtaat aattctttta tatatttttt caattggagt gttggtgtta    540
ctatcctatg attgagggggg gagtattaga gttatggtaa gtatattata ttagagtatt   600
atgtttggag tattatattt attaggagtc ttgtattata tacctacgag ctttcatatg    660
cacgcgatgc gtgcgttaat ttcaaaattt gttattctat tagatactcc attcgtactt    720
tatttatgat taaacttaaa tgtgaaaaat tcaacagtta gatgaattta gatatattaa    780
ttcgctaatg taaaaaaata aaaaggttgt gagtgattgt taacattaat tttttgtgaa    840
tgaatattga acagaaagaa caaaaataat gagttggttt aactaaatta aatagtatca    900
aaagtagtga atgttcagac ttttcatgtg cacgttatgt atgccatctt ttttttataa    960
gttataaata ttttgtccat ttaatttttg attgaagtat ttgatgcata taccatttta  1020
aacttgtttt aaatggcaag ttggaatgag aattttttaa atgatttgct tttgtaattt  1080
tttatattct attgattaga tcattaaggg tattttggtc actttaaaag aggacaccac  1140
acctcctccc ttggcttata taatagagat ctgttaagtt gttagtacgt atatctagtt  1200
cagtaaggat ttctgatatt aggttgtata tatatattcc tcaaaagttt gataagtttc  1260
ccatattcta aaccttaaca ctttgagtga gtgaaatgtg gcagaagcta atttcttttta 1320
tgtatattga tgatatacac agaatgcatg catgtgttta tagaagactt accattcaaa  1380
atcaacaata tacatggatt agaacaattt ttaaaatgta cttcaatttt ctctcactgg  1440
acttggacac gattggggag aagaaggtgg tggacaccgt gtaggaggag aagactgaag  1500
agaagacata caccatacct ttcaagaaga aggatagagt atgtgtgtat gtattagcta  1560
ggcagactgt tggagtctag aggttgagat gtggaataag aaggagaata atacgggtga  1620
gaggttttag ttaattgtca aatgttgcgc tctagcatat gtccttattg atagatgact  1680
gtcaaagttt ttgatcacta gctccttatt tcactactaa atactaatta cactaatcga  1740
ctgtacatac acccacacac atatatatac atatatgaga atgagggata acctagtggt  1800
taatgcttct ctcccggttc caggagtcct atgatcgatt ctcacccttg acaagttagg  1860
ttctcccttta ttccccaagc ttatcacacg tacacacgtc gctgtcatag acatgtcatc  1920
tttaagttta agttaaaaat ttataataaa ttaattaagt gtatggcatg catgtatagt  1980
tgcttccagc aattaattcc tcctaaaatt aaatagttag cttaccagtc cacaatgtag  2040
gaataacaaa gaataaatgg gggaagtaga gtgaatatat tatataattc atataatagt  2100
ctcgcggcta ttaagaagac gattttttgct aagctggtta tggtgtgttg tttcttcttt  2160
tttttctctc ttgctcaggt aattaggttg gtgtttgaga ataatactg aaaatgacga   2220
```

```
acttacaaag ctctcctcca tccttcaatt actacaacag gaagaaattg gtcacaatcc    2280
ttagcatcga cggtggtggc attcgaggca ttattcctgc tgtcattctt gcttttcttg    2340
agcgacttct tcaggtacgt acataaaaca taatcatact acatatacat atctcctata    2400
tatccattca tctctcgcac tcatttgtac tcatttagcg tgtgaatcgt gcatatcaca    2460
tcgaacaatg ttattttgat atgaataatg ataattaggt tcctagtaga gttgggcatg    2520
atagccgggc tagtccaaca cgttccacca tgactttatc cggttatccc cacacgatac    2580
aattttgttc gaaagtgaaa gacactgtta tgggtcatat atagacatca tttttaaaat    2640
ttggcataaa tatgagaact atgtaatttc tatcttgtta tcattgatac cttgtaaaac    2700
tatgcaatcg tgcatgcacc taatgaataa taacaataaa caataaagta actaattaag    2760
tataatgagt agtgtacaat tgtacatgtg cacaataatt tcagatgcga aatgaaaata    2820
ttatttacta cgttcataat atgttaaaaa aagcactcct gagacataat gtgatgcata    2880
gttaccccgc aaaaaacaat taattaatat gatgtcaggt taattggtta taattatgta    2940
ggagttggat ggagaggaag taagactagc agattatttt gatgtgatag caggaacaag    3000
cacgggaggg ttgattacag ccatgttaac tgcaccagat gactataatc gtcctctata    3060
tgctgcgaaa gatatcacaa cattttactt gaagcatggt cctcaaatat ttcctcagga    3120
aaggtaaaaa atttaaatgt cagaatattc cataccacaa tataattttt aataagtagc    3180
ctataaatgg tggtcacacg ctaagcatga caatttttatt aaaagatcaa tcgaattttt    3240
attaaatctt ataggattaa aaattagaat tcattgggtg gaaaaaaaaa tgaaaaaggt    3300
tgtgattttt cgtccatcgt taaatcgaaa caaaagaaa agtcaaagta aaggcttatt    3360
atttctcatt tataaatatc caaattttag tacccaatac ccataaatag ttcgaaccat    3420
atagacacaa taatcaattt tcgtgtgaat ggtttgtagg gaaaccctat cctttcttat    3480
ccataatggt gtataaataa atttttacccca caaaaatata caagtttctt catatactat    3540
atcatgaaaa taactattat gacatatatc tacttagtta cccgtcgagt aggttttacta    3600 aacttatcca tacatcaaat atgtcaaaaa gaatccagtt aattgtttga ggatgtgagt    3660
catgtgattg gtgagctatc aattgttcat cactttctaa attcaaactc gaggaagtaa    3720
tcaattggtc ttggcatagt ggttgtccac tttgtccctt aatcaattat cgaggattcg    3780
attctcaatt tttgggaatg gaaagatatt tttgaccagt cctttaccct taagtgtagc    3840
actcgaagcg agaggattaa tcattgctgt cggcggtgaa tacttagatt gttttttaaaa    3900 aaaacttgag ggagtgatac tagcagatca tgtatcctca tgtttgtcaa tgaaggtgtg    3960
caaagtatat gctagtatgc tactaccgcc catgaccctg aaattcaatt tttcattgtt    4020
tgttttagtt gcattgtcct atttggctat ttcaatactt tagtaacttt aaaaaaaaaa    4080
tacttcctcc atctcttttt actcgctaca ctttttatta tgggaagttt cacattactt    4140
gctacacttc ttttttgggc aataaactat ctctatctct ctcctcccac atgagtcccg    4200
tgttgagatc ctctagagtt ccaaaaaaac tctacacggt agagttcgtt aaatatcagt    4260
cgttgattaa gaaatcaaag gcttgtattt tgttttccaa aaatccccccc tattttcccc    4320 cgaatatcct gccaatatct tttccttttc caccaatcat gagcctttga ttttatgata    4380
tatggtcagg attcaactct actttgtaga gttttcataa aactctagag gatccggacc    4440
ccatgagtcc cttttctttt tattctctac ttctctcttc tccaaaaatt gcctaggagt    4500
ccgtgaaatg agaagtgtag cgagtaaaaa gaaacggatg aagtatattg ttaatatttt    4560
```

```
ttaaaatata tatattttat tgtaggatta atcttaataa ttactaaggg atttccaaca    4620
tgtttgatgt cgcctgtatt ttgctgacca agtttagaaa aattgatagg ttgtttctaa    4680 catcttttg  ccggccacca agctggagat gtagacatat agaagtagtt tatgattttc    4740
ccactttgaa ctggttatac atacattaat tagttattac aagtctttt  tagatgatta    4800 ctccatcgat tccaccattg ttcatgtcat cttgtcatat acagcgactt tcgtaactat    4860
tgtgtattat tattatatac tccctcttta ccaatctaga tgcaattatt ttcctttat    4920 ggtttctccg gacacacttt ttacatctat gattatatat tagtagaatt tagttataga    4980
tgatatattg taaatttata cattattgaa acaaatctaa tatgatattt atatgataat    5040
tttatttgct tatatcagta aaaaaatatg cttagttaac attgatgatc tttaacccta    5100
gaaaaacaaa tgttgcaagt tatatggaat taacaaagga ggttatattt ttcttggaaa    5160
agaaccatag ttgtctcttt ccttgaagta caattatgat gtcagtgggt aatggaatct    5220
acccggatcc aaatcatttt ttagcgattt gtatcctcaa attttggacc caacggatat    5280
ggatcatgtc ttaaatcatt acatggagtc gtatccattt accccatttt taaaaattat    5340
tttaaaatat ataattaaaa gtgaaaaact taaaggattt tttaactgga ataatacaaa    5400
ctttgggccg ttctctcgca ataatacaaa ctttgatta ttttttaata atacaaactt    5460
taggccaaaa ttcctccagt aggttaatac cggttggtaa cttgttgtag gaggtaacca    5520
agctgacgtg gcacctttag gacacgtgtc tttatttgat tggctgtttt tttaaatta    5580 gggaaaaaaa aaaccaaaat ttttctttt  ttttctttc ttctcctgct ccccccttca    5640
ttctctttct cactactcca ccccaccgac ccccacccct ggccctgcc  ccagccccct    5700 ccctgcctgc acaccgcatc cctccgacga ccaaccccc  atctctggcc cttcccccac    5760
cccgaaacca taccgcaccc ctccgacaac cacccctggc ccctccccca cccgaaaacc    5820
acaccgcacc tcttcgacaa ccaaccccca tttctggccc ctccccacc  ccgaaaccac    5880 actgcacccc tccaacggcc atcacctgac gccattctcg atcgctcgaa cttagatcct    5940
ttcccgcaca acaacaagtc gtcgtcgtca ccgcgcgaaa tcaatacgat attcgaaaat    6000
ggcggtcatt ttattatcga cgaattggag gaggaggaag agacgtcgtt gttgacgatt    6060
tcgcatagtt acgcgatctg gggaagtggt ttcgtgtggt ggtgagtttg aggtggtttc    6120
gtggtggggg agtttgaggc ggtttcatgg ttggggacga ggtggtgatg gtggtttcat    6180
ccgtgggggt ggagctgtgg gagggggtgg aactgtggag gtgagggtgg ggggaggggg    6240 tggggggtgga gctgtggagg tggggaaggg gggtgggagt ggagccgtgg aggtggagga    6300 ggggggtggga gtgggctttc acattttcag ttggttggct aggggaagga ggaagagatt    6360
ttggagttta aaaaaatcga cctattctac atgttaatgg tcaacttgac ctactggagg    6420
aattttggcc taaagtttgt attattaaaa aataatcaaa agtttgtatt attgcgagag    6480
aacggcccaa agtttgtatt attcgagtta aaaaatccaa acttaaaacc attttatgat    6540
tttatctttc aaattactta tatgtttatt gtgatgaata tttatgttgt cattattatt    6600
ctttgtaatg tacaaatatg attttgcaat gaacaacata ctatcatata cttcctccat    6660
ttctaaataa gtgcaacatt tcttgttttc acatttgcca atgcattatt ttaaccagta    6720
atatcttcaa ttatcaataa gtaaaaatta taaaagttg  atattaaaaa aattcacatt    6780
tagatgaatc taacaagatc ccacatgact atgttttcc  taaaatgcaa atcactaaag    6840
ctaattgatg tttaaactgt gaatagtaaa cactatgcaa atgttacact tatttagaaa    6900
cggaggaagt aataaataac ccaattgaat agttatataa ttatcaaaaa ataagtaatt    6960
```

```
acaaaagatg gttaattcat aatgtagtat gtacccaagt gtagaaatat aaccaaaata    7020
atataatata tttctaatta aacactattg agttcattaa gaagatattc ttgcttttga    7080
gcttccttcc atttccgatt gatttgaata gtgagatctc gacaccataa cgtatcttag    7140
ttgtttgaac tagtcgaatt gaactgatac aagaaaggaa atagcagtag ttaaaaaaaa    7200
ttattcaagt ttataataca atgaacataa ttttcaaac atacaattaa cacattctaa     7260
taatacaata aacatgctcc cgcacatagt cccgactatt aggctgtgca aacaacccaa    7320
tagcacagga ccccgaattt cttagggtcc ccaaaatctg gaaacaaaaa aatatagttg    7380
attacggcgc taaaacaatt caactacata tattagcaga gttgttatat gagattaact    7440
ctacaacaag aatacgcaag ttcgactcat gttccgggaa tatctttaca tactttttgc    7500
aagtgtttat gatattttct tctagtttga gcatttcact catctcccca ccacttcata    7560
cttactttct aactattttc cttactttt tttcaatact ttttttttgat aaattgtttt    7620 tctcaattct ttagggtact tttttgataa attcttttat caattcctta gggtacttat    7680 ttttttttgga agtgtatatt tgtccaataa gaattgaata atttcctgcc acaagtttac    7740
tagtttaccg gttagtcac ctcatcatat atataaattt tttttttttt gttgtacctt     7800
ttagagtgag atagaaaaat tattatcgtt atctttataa gtagaacatc agtcataatg    7860 tggtttata ttgagttgtt acacacaatt tcaaatgagt ttgaggtttt agttttcga      7920 tttacaagat aaatttatat aattgtaata ttataaaaga tttttttttat catttgagtt   7980 gcaaaaaaat gagattaggg gtccaatcct aaaattggaa caagacctcc aaaatgttta    8040
agacggccct gcccgcacac aatgagcatg tgattaaaat gagcatgtta gtaatacaat    8100
gaacatcaac ctaaaaatgt gcaccttgta tttgtaaatg gtacaataaa tatcacataa    8160
tcatacaaag aacatttgaa caaatatcac acatttatag acaaatatat atgataatca    8220
acccatcatt aattcatatc atttcattga atatattaca aacacataac gaattatgac    8280
tgaaatgcaa taaacatctg accaacatgt gtttcagtga acatattctg attggacaat    8340
gaacatatgc cataattcat gttattaatg caattaaat gtgtcaaaga cataataaat     8400
atatgaagaa ctgtacataa catctgaaca aacacataat aaacatatgg ctaaatgtaa    8460
taaacatatg accaacacaa attcaattag tacattacaa taatacaacg aacatatatt    8520
tacagtacaa cattacctgt tttttctag atgtcgaact cgttcatctc ctttattcat     8580
tgggctctct catttgttca ttgggacatc aattgcaagg ttgttttcat ttttcacaaa    8640
tatcaagatc ttcactagaa aagatggaaa aaaaataag aaatgaaagt gcaatatgta     8700
aaaaaaaata ttctttttc ttatcaaatg catagatcta ataacttatg ttctttgcaa     8760
ctcgttgtat tcatcttcat gtacgaaaat tgtttaaaaa aatgaagaat ttaaaaaggt    8820
tgatgagaaa ggttagagag aagttaaaga gatgttggag gatttgggga aagagataa     8880 aaagtctttg aaaatttctg gggaaaaatg aaagtaatga attcaaattt ttttatgttt    8940
tttggtgttc attggagatc aacaaatgtt catttcgtgc attttttggtt taatgaatac   9000 gcgttttatg ttttgttgac atccgttttg acccatgcac accttcctca acatacatcc    9060
gttcgcacgg ttgatctact gatcattcgc ttgaaagggg aataaggtca tgacagcgtt    9120
aagaatgaaa caagaaagat cgtatatttg ttggtaactt ggtactacaa ttagggttgt    9180
tcaccggtcc aggatcggat cgaacctgac ctgcctggac cgttctttat gggattcttc    9240
ggaccaggtg tggatcggaa aaatcaggtc tggtcttcag tccggacctg ttgggccgga    9300
```

-continued

```
aaaattaact tgtatctctg attcttcgga cctgttacga cccaccatca ataaatatca   9360
gaattccata gatttatcag tttacagagg accaactaca acaagcaaac aaaaaaacaa   9420
ttctagtact tcctccgttt ttttttttac ttgcaacact ttttttttcat caactccaat   9480 gtaaaatttg ggtatgagat aggcatacag gaaaaaaaga gagatcccca tgtgattgga   9540
gagagataga gagaaaggaa aagaaaaagt agaaagtgtt gcaagtaatt aattattttc   9600
tttttaggaa agtgttgcaa gtaaaaagac ggaggaagta tttagtttttt attacaaatt   9660 gtttgggggg gggggcagg agacatggag tcacactaga ctaggacact caaagaggca   9720
ccaatgctac tcactaagtg attaaagtta aagatagaaa agggtgaaaa agactcgcga   9780
actgaaaaac aaacctgatc ggtggtgggc ggtagctgcg gtcgcctgag cggcgtcgtg   9840
gcgtcggtgc gactggtttg gcgaggcgtg accgcgtgag gactgaggtg tttgagttct   9900
cttagggttt cttttagaat gactaaatga gagagggaga agtaggaata aagggctggc   9960 attttttta aaaaaaaaaa tactaaaaag cttccgagtt ttcggtctgg accggatttt   10020
ttcgagtttg aaccagaccg aaccggaaac ccggaataga cacattccac ggaccgggga   10080
ccggattgga atcgccggtc cggttcgatc cgatccaaaa tccggtccga ttagatccga   10140
cccacctatg tgaacagccc tagctacaat actacatgac tacctgcctt attaactctc   10200
ccttttatta gattttcgt tagctaataa ctcccttagg atattgaatc tactttgttg   10260
gttataactc ttataagtta ctattatagt aggagaacaa ctattattat gtgcaaaatt   10320
acacagaatt tgttttttctt ccatttttag gggaccactt gctcagctga ttagcttcat   10380
caaagcaatg acagggccaa aatatgatgg caagtattta cgccatatac taagggaaaa   10440
attgaaagag acaaggttgc atcacacact aacaaatgtt gtcattccaa cttttgacat   10500
taagaccttc caaccagtta tattctcttc ctacaaggta aataaattat aatcgtgtgc   10560
tcatctccaa taatttacc ttaaatgaat tttcatcaac taatcatttg ctttgctgat   10620
gaccatcctt gatttgaatg aagagaatat atatatatat atatatatat atatatatat   10680
atatatatat atatatatat attatatata ctatatatat agtacgtagt acgtacgtac   10740
gttacgtacg ttacgtagta cgtacgggta cttaacgtcg tannnnnnnn nnnnnnnnnn   10800
nnagtatagt agtatatata tatatatata tatatatata tatatatata tatatatata   10860
tatatatata tatatatata tatatatata tatataggat gaggaactag ctcatgtggt   10920
agagcactcc cctctgatcc ttgaggtcag gggttcgatc cttaccccca acattatgtt   10980
ggggcatttc cttagcatgc tttgcatgct ttaccagcca atgtgctggt agttcctaca   11040
aggctagtag aatgaatttt acgtgttata actcatatga ataagtgatg taactccaaa   11100
aaaaaaaata ttagaaaaaa gaaattcaag aaaaaaaaaa ttgggatcaa attttttaa   11160 ggggtataac tctaataaag tattgtaact ctaatccaat catgtggtcg aaattcattc   11220
tcatttctca tttaaagagc attctctat gatattactc ctatatatat tcgtgcttgt   11280
tttttctttt attagatgat cctagcttga tatcgacgca aactaagaac ttcaaaagga   11340
aataatgaaa ttactatttt aatgttttct ttttgtttta ttccatatat atgtaaacac   11400
agtattatcg atctgatagg cataaatgtt atacttaatg tgattatcca aatagtttaa   11460
ttgagagttt tactcttatc aagttatcat gtcgtctagt gttaataatt ctttagtttt   11520 atgtctatttt tgtcgtagct atagtccgac tggtcaagta cttgatcaaa cagtttaagc   11580
ggtgaaccta ttgcatgact tttacctagg caactagtat atgtctggaa aagtgaatga   11640
cgatctctca ttttcatagt gaaatttaca atattctcta agcttttatg atattaatga   11700
```

```
taggtgatat atgatgcgag gttattgaag tgtgtggatt ttcctagtgc cctttagtta    11760
cattgttaat ttgttagggt tgattcaagt agatttacag acctatatga gggcataact    11820
aagagaccat attttattga tggaagaaaa gtagagaggg tcactttagc agctactcct    11880
actacgagta gctaagtatt acggatttaa aaaatattcc tcccaatgat agaaattaag    11940
gtcgaaataa aacaacattt taagataaca catatttata aaaacaaaac tagtgaaaaa    12000
taacctagac aaaattcgaat cttatttgca tcgacaaact ccaacatttt catcattatt    12060
ttcaaaaaca tatcaaaaca ttgaaaatgc cagatcttct gtccgcccccc tcctttgac    12120 caaaatatga atttatacgt aagtagtttt accttcgtaa ttttacattt gtgattttgt    12180
agacttcaat taacattttc atttgtgttc aattaaactt tgcgacttag tcaacggatt    12240
aattacatcc ttctttatgc ataaaaaagt ccatttatca atcaacccaa gaagactcac    12300 aatgtttta tcatttaatt tttgcaaatt ctaagttatc atttaatttt tacagattct    12360
aagttatcct gatctggatg cgaaattatc agatatatgt ataggcacat cggccgctcc    12420
taccattctg ccttctttct atttccaaaa tgcatttgaa aacgaaaaga caagggaatt    12480
caacctcatt gatggtggaa ttgtgagtac aaatccggta agtcaagctc aatcaatcat    12540
attattattc ttatgcttag aggatgcaca atagcatggt ttcacttggg gcaaaggtga    12600
accaatgggt gaggttggtc ttaccattgg ggtgagtcaa ggcaaacatg gcttaatgag    12660
gttgggataa tttgctcccc ctctctccca acccatgcat cggaccaaga gcccaagcta    12720
gtaacaaaag gcttgtgtac tttcacagag aatgagcttc atgtctttga gtgtagagct    12780
tttttccttc ccaaacgtcc tactcttaga attgttattt acataaccta ctttaattat    12840
ttttttttat taatttataa aatagttgtt atgttattac atagtaagtt gtcgtatcag    12900
agttcttttc acgaaaactc aaagctgaaa cataaaaaca gacgagttta ttcatcatac    12960
cacctagata taccacaatg ttagtacatt ttgttaattt ggaactatcc aaatgaacaa    13020
taagcagaaa aatagtcttg agtgtaatgt ctacaatgtt cacaatacat tcaagtgtat    13080
gttgaatttt ttgtataaga gcctaaaaaa ctttttatcca acaatacttt aaaccagcag    13140
atagaatatt atttgatgta tcaataattt cattctatct ttttgtttg tcgtctgggc    13200 agacttatct ggcaataaat gaagttacca acaaatgat gaaggagaat ccagattacg    13260
ggaccatcca taataagttg ctggttttat cgataggaac aggatcagga aaaattgagc    13320
agaaatacaa tgctaaaact gcaggaaagt gggggcttgt ctcttggctt tttcaaaatg    13380
gatcatcacc aattataagt gcttttttatg aagccggggc tgacttagtt gattaccaaa    13440
ataatatcct cttccaatcg tttcgttcag aggacaagta ccttcgtgtg caagtaagtc    13500
gcatgatacc cttcaaattt aactttaatg tagtaatccg tttacgatta tcggcacat    13560 attgttggaa ataaaacagg atgacagctt aacaggaaca actgcttcaa cagatgtagc    13620
aacagagaag aacttggaaa atctagtgaa aattggtcaa gaattgctta acaaaccagc    13680
cagcagggtg gacccagaaa ctgggcatct gaaagcaatt ccacaccttg gtaccaatgc    13740
agatgctctt cgaaggttgg ttcataaatt ttataatatt gccaatataa attgcacatt    13800
attagttatt actactagat agattaacaa gtcattaaca aataggttcg caaaacaact    13860
ctcggatgaa agaaaatacc gcaggggcaa agactccaat cagatgcaag agtacagctg    13920
agctgacgat gtgcaggcat ttctgagtac tgagctgtct ttgattgtat actatatgat    13980
aaatgtgtgc aatgtaattg acctcaaatc ttctatctca taatttttgt actattctgt    14040
```

```
tggttgatta taaatttgta acgttctaaa gattatctta aaaggtacta gaccgtagta   14100
caatacctgc taataatata tagtagcata cattcttttt ttggctccct tccgggaatc   14160
cgtggtaaga tgaatttcct ttagactgtc ctcacacagg gccactcacc cagaagacca   14220 acaaccccc  tcccccaac  tatattgaaa ttttgcttg  caccaagatt tgaaccttgg   14280
```
(Note: original shows acaaccccccc tcccccaac tatattgaaa ttttgcttg ...; preserved below)
```
acaaccccc  tcccccaac  tatattgaaa ttttgcttg  caccaagatt tgaaccttgg   14280
cttcccatat gtgagacacg aaaccatacc attggaccca agggtccttg gtatataaag   14340
tagcatacat gtgacacaca aagagagaca gtagatgttg cttcaggtaa tgcagaaacc   14400
ccctatatga tcaacatgat caacagaact atgtatatct atacttcttt ccctagataa   14460
gcaagaattt atggaggcta actatccttg tttccctgta atgcttatac aagaagatgc   14520
aaaatagaaa gctcagagcc agatactctc ttaatagacc caggagtaac ctgaacttgc   14580
taccatattc aacacattta agccagaagg taaaacacag aagttcgaaa gtaaagacag   14640
caagttcaca aagctaggga tcttttgaa  gtgcaaccat cggacattat gggattgcta   14700
a                                                                   14701

<210> SEQ ID NO 26
<211> LENGTH: 1215
<212> TYPE: DNA
<213> ORGANISM: Artificial Sequence
<220> FEATURE:
<223> OTHER INFORMATION: cDNA of Beta vulgaris phospholipase 2

<400> SEQUENCE: 26
atgacgaact tacaaagctc tcctccatcc ttcaattact acaacaggaa gaaattggtc     60
acaatcctta gcatcgacgg tggtggcatt cgaggcatta ttcctgctgt cattcttgct    120
tttcttgagc gacttcttca ggagttggat ggagaggaag taagactagc agattatttt    180
gatgtgatag caggaacaag cacgggaggg ttgattacag ccatgttaac tgcaccagat    240
gactataatc gtcctctata tgctgcgaaa gatatcacaa cattttactt gaagcatggt    300
cctcaaatat ttcctcagga aaggggacca cttgctcagc tgattagctt catcaaagca    360
atgacagggc caaaatatga tggcaagtat ttacgccata tactaaggga aaaattgaaa    420
gagacaaggt tgcatcacac actaacaaat gttgtcattc aacttttga  cattaagacc    480 ttccaaccag ttatattctc ttcctacaag attctaagtt atcctgatct ggatgcgaaa    540
ttatcagata tatgtatagg cacatcggcc gctcctacca ttctgccttc tttctatttc    600
caaaatgcat ttgaaaacga aaagacaagg gaattcaacc tcattgatgg tggaattgtg    660
agtacaaatc cgacttatct ggcaataaat gaagttacca acaaatgat  gaaggagaat    720 ccagattacg ggaccatcca taataagttg ctggttttat cgataggaac aggatcagga    780
aaaattgagc agaaatacaa tgctaaaact gcaggaaagt gggggcttgt ctcttggctt    840
tttcaaaatg gatcatcacc aattataagt gcttttatg  aagccggggc tgacttagtt    900
gattaccaaa ataatatcct cttccaatcg tttcgttcag aggacaagta ccttcgtgtg    960
caagatgaca gcttaacagg aacaactgct tcaacagatg tagcaacaga gaagaacttg   1020
gaaaatctag tgaaaattgg tcaagaattg cttaacaaac cagccagcag ggtggaccca   1080
gaaactgggc atctgaaagc aattccacac cttggtacca atgcagatgc tcttcgaagg   1140
ttcgcaaaac aactctcgga tgaaagaaaa taccgcaggg gcaaagactc caatcagatg   1200
caagagtaca gctga                                                    1215

<210> SEQ ID NO 27
<211> LENGTH: 404
```

<212> TYPE: PRT
<213> ORGANISM: Beta vulgaris

<400> SEQUENCE: 27

```
Met Thr Asn Leu Gln Ser Ser Pro Ser Phe Asn Tyr Tyr Asn Arg
1               5                   10                  15

Lys Lys Leu Val Thr Ile Leu Ser Ile Asp Gly Gly Ile Arg Gly
                20                  25                  30

Ile Ile Pro Ala Val Ile Leu Ala Phe Leu Glu Arg Leu Leu Gln Glu
                35                  40                  45

Leu Asp Gly Glu Glu Val Arg Leu Ala Asp Tyr Phe Asp Val Ile Ala
        50                  55                  60

Gly Thr Ser Thr Gly Gly Leu Ile Thr Ala Met Leu Thr Ala Pro Asp
65                      70                  75                  80

Asp Tyr Asn Arg Pro Leu Tyr Ala Ala Lys Asp Ile Thr Thr Phe Tyr
                    85                  90                  95

Leu Lys His Gly Pro Gln Ile Phe Pro Gln Glu Arg Gly Pro Leu Ala
                100                 105                 110

Gln Leu Ile Ser Phe Ile Lys Ala Met Thr Gly Pro Lys Tyr Asp Gly
                115                 120                 125

Lys Tyr Leu Arg His Ile Leu Arg Glu Lys Leu Lys Glu Thr Arg Leu
            130                 135                 140

His His Thr Leu Thr Asn Val Val Ile Pro Thr Phe Asp Ile Lys Thr
145                 150                 155                 160

Phe Gln Pro Val Ile Phe Ser Ser Tyr Lys Ile Leu Ser Tyr Pro Asp
                    165                 170                 175

Leu Asp Ala Lys Leu Ser Asp Ile Cys Ile Gly Thr Ser Ala Ala Pro
                180                 185                 190

Thr Ile Leu Pro Ser Phe Tyr Phe Gln Asn Ala Phe Glu Asn Glu Lys
                195                 200                 205

Thr Arg Glu Phe Asn Leu Ile Asp Gly Gly Ile Val Ser Thr Asn Pro
    210                 215                 220

Thr Tyr Leu Ala Ile Asn Glu Val Thr Lys Gln Met Met Lys Glu Asn
225                 230                 235                 240

Pro Asp Tyr Gly Thr Ile His Asn Lys Leu Leu Val Leu Ser Ile Gly
                245                 250                 255

Thr Gly Ser Gly Lys Ile Glu Gln Lys Tyr Asn Ala Lys Thr Ala Gly
                260                 265                 270

Lys Trp Gly Leu Val Ser Trp Leu Phe Gln Asn Gly Ser Ser Pro Ile
            275                 280                 285

Ile Ser Ala Phe Tyr Glu Ala Gly Ala Asp Leu Val Asp Tyr Gln Asn
290                 295                 300

Asn Ile Leu Phe Gln Ser Phe Arg Ser Glu Asp Lys Tyr Leu Arg Val
305                 310                 315                 320

Gln Asp Asp Ser Leu Thr Gly Thr Thr Ala Ser Thr Asp Val Ala Thr
                325                 330                 335

Glu Lys Asn Leu Glu Asn Leu Val Lys Ile Gly Gln Glu Leu Leu Asn
                340                 345                 350

Lys Pro Ala Ser Arg Val Asp Pro Glu Thr Gly His Leu Lys Ala Ile
                355                 360                 365

Pro His Leu Gly Thr Asn Ala Asp Ala Leu Arg Phe Ala Lys Gln
                370                 375                 380

Leu Ser Asp Glu Arg Lys Tyr Arg Gly Lys Asp Ser Asn Gln Met
385                 390                 395                 400
```

Gln Glu Tyr Ser

<210> SEQ ID NO 28
<211> LENGTH: 40
<212> TYPE: DNA
<213> ORGANISM: Artificial Sequence
<220> FEATURE:
<223> OTHER INFORMATION: R59Q mutant - primer AlleleX

<400> SEQUENCE: 28
gaaggtgacc aagttcatgc tccgtccagc tcctgcagct        40

<210> SEQ ID NO 29
<211> LENGTH: 39
<212> TYPE: DNA
<213> ORGANISM: Artificial Sequence
<220> FEATURE:
<223> OTHER INFORMATION: R59Q mutant - primer alleleY

<400> SEQUENCE: 29
gaaggtcgga gtcaacggat tcgtccagct cctgcagcc        39

<210> SEQ ID NO 30
<211> LENGTH: 22
<212> TYPE: DNA
<213> ORGANISM: Artificial Sequence
<220> FEATURE:
<223> OTHER INFORMATION: R59Q mutant - primer common

<400> SEQUENCE: 30
tccccggaac catccttgcc tt        22

<210> SEQ ID NO 31
<211> LENGTH: 201
<212> TYPE: DNA
<213> ORGANISM: Artificial Sequence
<220> FEATURE:
<223> OTHER INFORMATION: partial sequence indicating detectable single
     nucleotide polymorphism that causes amino acid substitution R59Q
     in Sorghum bicolor phospholipase

<400> SEQUENCE: 31
gagcccgtcg tgctggggca gagggtgacg gtgctgacgg tggacggcgg cggcatccgt        60
ggtctcatcc ccggaaccat ccttgccttc ctcgaggccc rgctgcagga gctgacgggg       120
ccggaggtta ggctcgcgga ctacttcgac tacatcgccg ggacgagcac cggcgggctc       180
atcaccgcca tgctcaccgc g                                                  201

<210> SEQ ID NO 32
<211> LENGTH: 41
<212> TYPE: DNA
<213> ORGANISM: Artificial Sequence
<220> FEATURE:
<223> OTHER INFORMATION: V162I mutant - primer AlleleX

<400> SEQUENCE: 32
gaaggtgacc aagttcatgc tgagcgacac gctcaccaac a        41

<210> SEQ ID NO 33
<211> LENGTH: 41
<212> TYPE: DNA
<213> ORGANISM: Artificial Sequence
<220> FEATURE:
<223> OTHER INFORMATION: V162I mutant - primer AlleleY

<400> SEQUENCE: 33
gaaggtcgga gtcaacggat tgagcgacac gctcaccaac g                41

<210> SEQ ID NO 34
<211> LENGTH: 21
<212> TYPE: DNA
<213> ORGANISM: Artificial Sequence
<220> FEATURE:
<223> OTHER INFORMATION: V162I mutant - primer common

<400> SEQUENCE: 34
ctgcagcagc ctgacgtcga a                                      21

<210> SEQ ID NO 35
<211> LENGTH: 201
<212> TYPE: DNA
<213> ORGANISM: Artificial Sequence
<220> FEATURE:
<223> OTHER INFORMATION: partial sequence indicating detectable single
      nucleotide polymorphism that causes amino acid substitution V162I
      in Sorghum bicolor phospholipase

<400> SEQUENCE: 35
catgtccgcg ctgaggaagc caaggtacaa cggcaagtgc ctccgtaacc tgatcatgag    60
catgctcggc gagacgaggg tgagcgacac gctcaccaac rtcatcatcc ctaccttcga   120
cgtcaggctg ctgcagccca tcatcttctc cacctacgac gtacgtacgc cgccggccgc   180
cgtcgtcatg aataatcaat c                                            201

<210> SEQ ID NO 36
<211> LENGTH: 39
<212> TYPE: DNA
<213> ORGANISM: Artificial Sequence
<220> FEATURE:
<223> OTHER INFORMATION: S291L mutant - primer AlleleX

<400> SEQUENCE: 36
gaaggtgacc aagttcatgc tggcagatgc cccaccgcg                   39

<210> SEQ ID NO 37
<211> LENGTH: 39
<212> TYPE: DNA
<213> ORGANISM: Artificial Sequence
<220> FEATURE:
<223> OTHER INFORMATION: S291L mutant - primer AlleleY

<400> SEQUENCE: 37
gaaggtcgga gtcaacggat tggcagatgc cccaccgca                   39

<210> SEQ ID NO 38
<211> LENGTH: 19
<212> TYPE: DNA
<213> ORGANISM: Artificial Sequence
<220> FEATURE:
<223> OTHER INFORMATION: S291L mutant - primer common

<400> SEQUENCE: 38
gcctgtacac ggcgcggca                                         19

<210> SEQ ID NO 39
<211> LENGTH: 201
<212> TYPE: DNA
<213> ORGANISM: Artificial Sequence

```
<220> FEATURE:
<223> OTHER INFORMATION: partial sequence indicating detectable single
      nucleotide polymorphism that causes amino acid substitution S291L
      in Sorghum bicolor phospholipase

<400> SEQUENCE: 39
ctgtacccag tgaagccgtg gaactgccgc aagttcctgg tgctgtccat cgggacgggg      60
tcgacgtcgg agcagggcct gtacacggcg cggcagtgct ygcggtgggg catctgccgg    120
tggatccgga caacggcat ggcccccatc atcgacatct tcatggcggc gagctcggac    180
ctggtggaca tccacgtcgc c                                              201

<210> SEQ ID NO 40
<211> LENGTH: 39
<212> TYPE: DNA
<213> ORGANISM: Artificial Sequence
<220> FEATURE:
<223> OTHER INFORMATION: Q372stop mutant - primer AlleleX

<400> SEQUENCE: 40
gaaggtgacc aagttcatgc tgaccctgga cacccgctg                             39

<210> SEQ ID NO 41
<211> LENGTH: 42
<212> TYPE: DNA
<213> ORGANISM: Artificial Sequence
<220> FEATURE:
<223> OTHER INFORMATION: Q372stop mutant - primer AlleleY

<400> SEQUENCE: 41
gaaggtcgga gtcaacggat tgttgaccct ggacacccgc ta                         42

<210> SEQ ID NO 42
<211> LENGTH: 20
<212> TYPE: DNA
<213> ORGANISM: Artificial Sequence
<220> FEATURE:
<223> OTHER INFORMATION: Q372stop mutant - primer common

<400> SEQUENCE: 42
gtcgggatcg gggagcggat                                                  20

<210> SEQ ID NO 43
<211> LENGTH: 197
<212> TYPE: DNA
<213> ORGANISM: Artificial Sequence
<220> FEATURE:
<223> OTHER INFORMATION: partial sequence indicating detectable single
      nucleotide polymorphism that causes amino acid substitution
      Q372stop in Sorghum bicolor phospholipase

<400> SEQUENCE: 43
gcatccagga caactcgctg cacggcgccg cggccaccgt ggacgcggcg acgccggaga      60
acatgcggac gctcgtcggg atcggggagc ggatgctggc gyagcgggtg tccaggtca     120 acgtggagac agggaggtac gaaccggtgc ctggggaagg aagcaacgct gatgcgctcg    180
ctgggatcgc aaggcag                                                   197

<210> SEQ ID NO 44
<211> LENGTH: 19
<212> TYPE: DNA
<213> ORGANISM: Artificial Sequence
<220> FEATURE:
<223> OTHER INFORMATION: Forward Primer
```

```
<400> SEQUENCE: 44
ggcccccatc atcgacatc                                              19

<210> SEQ ID NO 45
<211> LENGTH: 24
<212> TYPE: DNA
<213> ORGANISM: Artificial Sequence
<220> FEATURE:
<223> OTHER INFORMATION: Reverse Primer

<400> SEQUENCE: 45
aatcaggcaa caaattcact tctc                                        24
```

HAPLOIDIZATION IN SORGHUM

CROSS-REFERENCE TO RELATED APPLICATIONS

This is a U.S. national phase application under 35 U.S.C. § 371 of International Patent Application No. PCT/EP2018/054901, filed Feb. 28, 2018, and claims benefit of priority to European Patent Application No. 17158439.4, filed Feb. 28, 2017. The entire contents of these applications are hereby incorporated by reference.

FIELD OF THE INVENTION

The present invention relates to the field of simplification of laborious breeding programs by means of molecular biological methods, marker technology and genetic engineering. In particular, sorghum plants are provided which are capable of inducing haploidy through modifications in the genome concerning a preferably pollen-specific expressed patatin phospholipase, thereby producing haploid offspring and capable of producing inbred lines for hybrid breeding in a short time by chromosome doubling. In particular, sorghum plants are provided which have mutations in the patatin phospholipase, methods for producing and identifying these mutations or the mutated plant and the corresponding nucleic acid molecule which encodes the mutated patatin phospholipase and vectors and host cells, in particular plant cells containing the nucleic acid molecule and plants generated from such plant cells which are capable of producing haploidy and their offspring, crossbred products, inbred lines and their respective plant parts and products.

Based on the knowledge of sorghum, the present invention provides methods for the production and identification of transgenic and non-transgenic plant haploid inducers and the corresponding plants which have obtained the property of haploidy induction or whose induction performance has been improved. Furthermore, the invention also encompasses seeds or offspring, organs, plant parts, tissues or cells of the plant according to the invention and their use.

BACKGROUND OF THE INVENTION

Sorghum is a relatively new crop in Germany, but due to its mass growth, drought tolerance and good water and nutrient efficiency, it comes into the focus of science and practice in the search for further high-yield crops for substrate production, in particular with regard to biogas production but also for use as feed, food and for ethanol production.

General breeding goals for sorghum are adaptation to the climate of Central Europe, that is, improved cold tolerance, improved yield, stability coupled with good youth development and development of disease and pest resistance.

Sorghum can be improved by breeding like a self-pollinating crop. The improvement of the population can be achieved by elaborate selection breeding by a targeted selection of the best plants for seed production for the next crop year. In addition, hybrid breeding has created new options for improving varieties. However, the process of hybrid breeding relies on several generations of continuing generation of homozygous father and mother lines, which also makes the process of hybrid breeding time consuming and costly, despite good results.

The object of the present invention was therefore to provide an efficient system for breeding sorghum.

SUMMARY OF THE INVENTION

The present invention relates to the field of simplification of laborious breeding programs, marker technology and genetic engineering. The invention provides sorghum plants which are capable of inducing haploidy by modifications in the genome which concern a pollen-specific expressed patatin phospholipase, thereby producing haploid offspring and can be made for hybrid breeding in short time by chromosome doubling inbred lines, that is, homozygous father and mother lines. In addition, the findings can be used to produce transgenic and non-transgenic plant haploid inducers or to improve the induction performance of plants.

The present invention therefore relates to the embodiments listed in the following items [1] to [29] and illustrated in the examples.

[1] Sorghum plant which is capable of inducing haploidy, characterized in that the plant has one or more modifications relating to an endogenous patatin phospholipase, which is preferably expressed pollen-specific.

[2] Plant according to [1], characterized in that the patatin phospholipase is encoded by the nucleotide sequence according to SEQ ID No.: 1 or 2 or by a nucleotide sequence which is at least 80% identical to SEQ ID No.: 1 or 2 or is encoded by a nucleotide sequence which hybridizes with the sequence complementary to the nucleotide sequence according to SEQ ID No.: 1 or 2 under stringent conditions, or which comprises the amino acid sequence shown in SEQ ID No.: 3 or a homologous amino acid sequence.

[3] Plant according to [1] or [2], wherein the modification of the patatin phospholipase is the cause of the suitability as haploid inducer.

[4] Plant according to one of [1] to [3], characterized in that the one or more modifications
  a) are one or more mutations in the endogenous gene encoding the patatin phospholipase defined in [2], preferably substitutions, resulting in one or more amino acid exchanges or generation of a stop codon;
  b) one or more insertions of an expression cassette which comprises a promoter operatively linked to
    (i) a nucleic acid molecule encoding dsRNA, wherein the dsRNA comprises at least 19 nucleotides, which is complementary to a partial sequence of the nucleotide sequence defined in [2]; or
    (ii) a nucleic acid molecule encoding the patatin phospholipase defined in [2] or a functional part of the patatin phospholipase, wherein the encoded patatin phospholipase or functional part thereof has one or more mutations resulting in one or more amino acid exchanges or generation of a stop codon; or
  c) causes a knock-out of the patatin phospholipase.

[5] Plant according to [4], characterized in that the one or more mutations result in an amino acid exchange
  a) in the range of amino acid positions 37 to 240 according to SEQ ID No.: 3, preferably wherein this range corresponds to the functional domain of the patatin phospholipase; and/or
  b) in the range of amino acid positions 241 to 385 according to SEQ ID No.: 3, or
  c) in the generation of a stop codon in the range of amino acid positions 241 to 385 according to SEQ ID No.: 3.

[6] Plant according to [4] or [5], characterized in that the one or more mutations for an amino acid exchange in the range of amino acid positions 40-93, 135-204 and/or 270-320 according to SEQ ID NO.: 3, preferably in the range of amino acid positions 53-85, 150-192 and/or 285-311 according to SEQ ID No.: 3, or more preferably in the range of amino acid positions 55-75, 157-167 and/or 285-298 according to SEQ ID No.: 3, or generating a stop codon in the range of amino acid positions 322-402 according to SEQ ID No.: 3, preferably in the range of amino acid positions 342-392 according to SEQ ID No.: 3, or more preferably in the range of amino acid positions 362-382 according to SEQ ID No.: 3.

[7] Plant according to one of [4] to [6], characterized in that the one or more mutations results in an amino acid exchange at the amino acid position 59, 162 and/or 291 according to SEQ ID No.: 3, and/or in a stop codon at amino acid position 372 according to SEQ ID No.: 3.

[8] Plant according to one of [1] to [7], characterized in that the modified patatin phospholipase
  (i) comprises an amino acid sequence according to SEQ ID No.: 3 or a homologous amino acid sequence in which at least one amino acid exchange is present, wherein arginine (R) at position 59, valine (V) at position 162, and/or serine (S) at position 291 according to SEQ ID No.: 3 is replaced by another amino acid, preferably by glutamine (Q) at position 59, isoleucine (I) at position 162 and/or leucine (L) at position 291;
  (ii) is encoded by a nucleotide sequence which comprises the coding sequence of the DNA sequence according to SEQ ID No.: 1 (derivable from the corresponding cDNA according to SEQ ID No.: 2) or a DNA sequence which is at least 80% identical to SEQ ID No.: 1, in which at least one nucleotide exchange is present, resulting in an amino acid exchange, wherein one or more nucleotides are exchanged at nucleotide positions 421-423, 815-817, 1420-1422 and/or 1663-1665 according to SEQ ID No.: 1 (corresponding to nucleotide positions 175-177, 484-486, 871-873 and/or 1114-1116 according to SEQ ID No.: 2);
  (iii) comprises an amino acid sequence according to SEQ ID No.: 6, 9 or 12; or
  (iv) is encoded by a nucleotide sequence which comprises the coding sequence of the DNA sequence according to SEQ ID No.: 4 (derivable from the corresponding cDNA according to SEQ ID No.: 5), SEQ ID No.: 7 (derivable from the corresponding cDNA according to SEQ ID No.: 8), SEQ ID No.: 10 (derivable from the corresponding cDNA according to SEQ ID No.: 11) or SEQ ID No.: 13 (derivable from the corresponding cDNA according to SEQ ID No.: 14).

[9] Plant according to one of [1] to [8], characterized in that the plant is homozygous or heterozygous for the one or more mutations, preferably characterized in that the plant is homozygous for the one or more mutations.

[10] Nucleic acid molecule encoding one of the identified patatin phospholipase mutated in [4] to [8].

[11] Nucleic acid molecule according to [10], characterized in that its presence in a plant, preferably in the absence of a wild type patatin phospholipase, results in the plant being able to induce haploidy.

[12] Nucleic acid molecule of at least 15, 16, 17, 18, 19 or 20, preferably at least 21, 22, 23, 24 or 25, more preferably at least 30, 35, 40, 45 or 50, and most preferably at least 100, 200, 300, 500 or 1000 nucleotides in length that specifically hybridizes to a nucleotide sequence as defined in one of [5] to [8], and comprises one of the mutations or a pair of nucleic acid molecules that is suitable for a range containing at least one of the mutations, to amplify in a polymerase chain reaction (PCR), preferably in the form of an oligonucleotide, preferably having a maximum length of 50 nucleotides, which preferably has one of the nucleotide sequences according to SEQ ID No.: 28-30, 32-34, 36-38 or 40-42.

[13] Vector, preferably a plant vector, comprising a nucleic acid molecule according to one of [10] to [12], or an expression cassette defined in [4].

[14] Host cell, preferably a plant cell, containing a nucleic acid molecule according to one of [10] to [12], an expression cassette defined in [4], a vector according to [13] or the nucleic acid molecule according to one of [10] to [12] as transgene, optionally under the control of a heterologous promoter, preferably a pollen-specific promoter.

[15] Method for obtaining a plant capable of inducing haploidy or having an increased induction rate with respect to the wild type, comprising the following steps:
  (a) (i) mutagenizing plant cells and then regenerating plants from the mutagenized plant cells or mutagenizing plants;
    (ii) identifying a plant from (i) having one or more mutations in an endogenous DNA sequence which correspond to and/or which result in one or more of the mutations identified in [4] to [8], where aspartic acid (D) at position 75, glycine (G) at position 79, and/or proline (P) at position 203 of the amino acid sequence according to SEQ ID No.: 3 is replaced by another amino acid, preferably by asparagine (N) at position 75, arginine (R) at position 79 and/or leucine (L) at position 203, or which corresponds to these, and capable of inducing the obtaining of haploid offspring at an increased rate compared to a non-mutagenized plant; or
  (b) (i) introducing the nucleic acid molecule having one or more mutations corresponding to one or more of the mutations identified in [4] to [8] and/or resulting in where aspartic acid (D) at position 75, glycine (G) at position 79, and/or proline (P) at position 203 of the amino acid sequence according to SEQ ID No: 3 is replaced by another amino acid, preferably by asparagine (N) at position 75, arginine (R) at position 79 and/or leucine (L) at position 203 or which correspond to them, in plant cells, or introducing the expression cassette defined in [4] into plant cells; and
    (ii) regenerating a plant, for example, a transgenic plant, from the plant cells of (i).

[16] Method according to [15], wherein the endogenous DNA sequence or the nucleic acid molecule is a coding nucleotide sequence which comprises amino acid sequences shown in SEQ ID No.: 3 for sorghum (*Sorghum bicolor*), SEQ ID No.: 18 for sunflower (*Helianthus annuus*), SEQ ID No.: 21 for barley (*Hordeum vulgare*), or in SEQ ID No.: 24 or 27 for *Beta vulgaris* (for example, sugar beet).

[17] Method according to [16], wherein the introduction of the nucleic acid molecule can be carried out, for example, by *Agrobacterium* transformation, homologous recombination, for example, by means of CRISPR/Cas or CRISPR/Cpf1 and repair template, and comprises mutagenizing chemical and physical mutagenesis, TILLING, targeted mutagenesis, for example, by using zinc finger nucleases, of TALE (Transcription Activator-like Effector) nucleases, meganucleases, and the CRISPR/Cas or CRISPR/Cpf1 systems.

[18] Plant containing a plant cell according to [14] and/or obtainable by a method according to one of [15] to [17], preferably wherein the plant is sorghum, sunflower, rye, wheat, potato, barley or sugar beet.

[19] Organ, plant part, tissue or cell of the plant according to one of [1] to [9] or [18] or seeds or offspring of the plant according to one of [1] to [9] or [18], wherein the seed or the offspring have a mutation defined in [4] to [8] and/or a nucleic acid molecule according to one of [10] to [12], an expression cassette according to [4] or a vector according to [13].

[20] Method for obtaining a haploid plant, comprising the following steps:
  (a) crossing a plant according to one of [1] to [9] or [18] with a plant of the same genus, preferably of the same species,
  (b) selecting a fertilized haploid seed or embryo, and
  (c) producing a haploid plant from the seed or embryo from (b).

[21] Haploid plant, haploid fertilized seed or embryo obtainable by the method according to [20].

[22] Organ, plant part, tissue, cell, seed or offspring of the plant according to [21].

[23] Method for obtaining diploid plants, comprising the following steps:
  (a) producing a haploid plant according to a method according to [20];
  (b) doubling the haploid chromosome set in at least one cell of the haploid plant, and
  (c) regenerating the diploid plant from the cell of (b).

[24] Diploid plant obtainable by the method according to [23].

[25] Method for producing hybrid plants comprising the following steps:
  (a) crossing a plant according to [24] with a second plant of the same genus, preferably of the same species,
  (b) selecting the hybrid plants with respect to the desired trait.

[26] Hybrid plant obtainable by the method according to [25].

[27] Method of identifying a plant according to one of [1] to [9] or [18] by detecting a mutation in the patatin phospholipase gene, for example, a mutation defined in [4] to [9], or a marker allele, which is coupled to the mutation, preferably using nucleic acid according to [12] as a molecular marker.

[28] Use of the nucleic acid according to [10] or [11], the expression cassette defined in [4] or the vector according to [13] in a plant for conferring the property of a haploid inducer or for increasing the induction rate for the production of a plant or transgenic plant which is able to induce haploidy.

[29] Use of the plant according to one of [1] to [9] or [18] for the production of a haploid fertilized seed or embryo or a haploid plant.

[30] Use of the nucleic acid according to [12] as a molecular marker for detecting a mutation in the patatin phospholipase gene.

First, some of the terms used in this application are explained in more detail in the following:

"To confer the property of a haploid inducer" or "Conferring the property of a haploid inducer" or "to be able to induce haploidy" means an expression comparable to that of a plant, by use of a nucleic acid according to the invention or by modification of the genome, in particular by mutation a patatin phospholipase, being altered to be able to produce fertilized seeds or embryos having a simple (haploid) chromosome set from a crossing with a plant of the same genus, preferably the same species, which does not have the property of a haploid inducer. The property of a haploid inducer, given as the absolute haploid induction rate, means that at least 0.1%, 0.2%, 0.3%, 0.4%, 0.5%, 0.6%, 0.7%, 0.8%, 0.9% or 1%, preferably at least 1.5%, 2%, 2.5%, 3%, 3.5%, 4%, 4.5% or 5%, more preferably at least 6%, 7%, 8%, 9%, 10%, 11%, 12%, 13%, 14% or 15%, or even more preferably at least 20%, 25%, 30%, 35%, 40%, 45% or 50% of fertilized seeds or embryos have a haploid chromosome set.

A "functional fragment" of a nucleotide sequence means a section of a nucleotide sequence which has the identical or comparable functionality as the total nucleotide sequence from which the functional fragment is derived. As such, the functional fragment can have a nucleotide sequence which is identical or homologous with the total nucleotide sequence over a length of at least 50%, 55%, 60%, 65%, 70%, 75%, 80%, 85%, 90%, 92%, 94%, 96%, 97%, 98% or 99%. Furthermore, a "functional fragment" of a nucleotide sequence can also mean a section of a nucleotide sequence which alters the functionality of the entire nucleotide sequence, for example, in the course of post-transcriptional or transcriptional gene silencing. As such, the functional fragment of a nucleotide sequence can comprise at least 14, 15, 16, 17, 18, 19, 20, 21, 22, 23, 24 or 25, preferably at least 30, 35, 40, 45, 50, 60, 70, 80, 90, 100, 120 or 140, more preferably at least 160, 180, 200, 250, 300, 350, 400, 450, 500, 600, 700, 800, 900 or 1000 consecutive nucleotides of the total nucleotide sequence.

A "functional part" of a protein means a section of a protein or a section of the amino acid sequence that encodes the protein, wherein the section can perform the identical or comparable functionality as the total protein in a plant cell. A functional part of a protein has a length of at least 50%, 55%, 60%, 65%, 70%, 75%, 80%, 85%, 90%, 92%, 94%, 96%, 97%, 98% or 99% of an identical or similar amino acid sequence, taking into account conservative and semi-conservative amino acid exchanges, as the protein from which the functional part is derived.

"Haploid inducer" also means an in vivo haploid inducer.

The term "heterologous" means that the introduced polynucleotide, for example, originates from one cell or organism having another genetic background of the same species or another species, or is homologous to the prokaryotic or eukaryotic host cell, but is then located in a different genetic environment and thus differs from any naturally occurring corresponding polynucleotide. A heterologous polynucleotide can be present in addition to a corresponding endogenous gene.

"Hybridizing" or "hybridization" is understood to mean a process in which a single-stranded nucleic acid molecule attaches to a largely complementary nucleic acid strand, that is, enters into bases pairings with it. Standard methods for hybridization are described, for example, in Sambrook et al., Molecular Cloning: A Laboratory Manual 3rd Ed. Cold Spring Harbor Laboratory Press, Cold Spring Harbor, N.Y., 2001. Preferably, it is understood that at least 80% or 85%, preferably at least 90%, 91%, 92%, 93%, 94% or 95%, particularly preferably at least 96%, 97%, 98% or 99% of the bases of the nucleic acid molecule enter into a base pairing with the largely complementary nucleic acid strand. The possibility of such attachment depends on the stringency of the hybridization conditions. The term "stringency" refers to the hybridization conditions. High stringency is given when base pairing is difficult, low stringency when base pairing is facilitated. The stringency of the hybridization conditions depends, for example, on the salt concentration or ionic strength and the temperature. In general, the stringency can be increased by increasing the temperature and/or lowering the salt content. "Stringent hybridization conditions" are understood to mean those conditions in which a hybridization takes place predominantly only between homologous nucleic acid molecules and homologs. The term "hybridization conditions" does not only refer to the conditions prevailing in the actual attachment of the nucleic acids, but also to the conditions prevailing during the subsequent washing steps. Stringent hybridization conditions are, for example, conditions under which predominantly only those nucleic acid molecules which have at least 80%, at least 85%, at least 90% or at least 95% sequence identity hybridize. Stringent hybridization conditions are, for example: hybridization in 4×SSC at 65° C. followed by multiple washes in 0.1×SSC at 65° C. for a total of about 1 hour. The term "stringent hybridization conditions" used herein can also mean: hybridization at 68° C. in 0.25 M sodium phosphate, pH 7.2, 7% SDS, 1 mM EDTA and 1% BSA for 16 hours and then washing twice with 2×SSC and 0.1% SDS at 68° C. Preferably, hybridization takes place under stringent conditions.

"Increasing the induction performance of a haploid inducer" or "the increase of the induction performance of a haploid inducer" or similar expressions mean that the haploid induction rate of a plant having the property of a haploid inducer is increased. Thus, the number of fertilized seeds which have a haploid chromosome set and a crossing of the haploid inducer with a plant of the same genus, preferably of the same species, which does not have the property of a haploid inducer, have increased to at least 0.1%, 0.2%, 0.3%, 0.4%, 0.5%, 0.6%, 0.7%, 0.8%, 0.9% or 1%, preferably at least 1.5%, 2%, 2.5%, 3%, 3.5%, 4%, 4.5% or 5%, and most preferably at least 6%, 7%, 8%, 9%, 10%, 15%, 20%, 30% or 50% higher than the number of haploid fertilized seeds, which is achieved without the use of the nucleic acid or without modification of the genome, in particular without mutation of a patatin phospholipase in the context of the present invention, that is, the haploid induction rate can be increased at least 0.1%, 0.2%, 0.3%, 0.4%, 0.5%, 0.6%, 0.7%, 0.8%, 0.9% or 1%, preferably at least 1.5%, 2%, 2.5%, 3%, 3.5%, 4%, 4.5% or 5%, and most preferably at least 6%, 7%, 8%, 9%, 10%, 15%, 20%, 30% or 50% relative to the previously achieved haploid induction rate.

"Complementary" nucleotide sequence with respect to a nucleic acid in the context of a double-stranded DNA means that the second DNA strand complementary to the first DNA strand has the nucleotides in accordance with the base pairing rules that correspond to the bases of the first strand corresponding to the Watson-Crick rules.

A "molecular marker" is a nucleic acid that is polymorphic in a plant population and is used as a reference or orientation point. A marker for detecting a recombination event should be capable of monitoring differences or polymorphisms within a plant population. Thus, such a marker is capable of detecting and distinguishing various allelic states (alleles). The term "molecular marker" also refers to nucleotide sequences which are complementary or at least largely complementary or homologous to genomic sequences, for example, nucleic acids, which are used as probes or primers. For markers, these differences can be found at the DNA level and are, for example, polynucleotide sequence differences such as SSRs (simple sequence repeats), RFLPs (restriction fragment length polymorphisms), FLPs (fragment length polymorphisms), or SNPs (single nucleotide polymorphisms). The markers can be derived from genomic or expressed nucleic acids, such as spliced RNA, cDNA or ESTs, and can also refer to nucleic acids used and considered suitable as probe or primer pairs to amplify a sequence fragment using PCR-based methods. Markers that describe genetic polymorphisms (between parts of a population) can be detected using well-established methods according to the prior art (An Introduction to Genetic Analysis. 7th Edition, Griffiths, Miller, Suzuki et al., 2000). These include, for example, DNA sequencing, PCR-based sequence-specific amplification, detection of RFLPs, detection of polynucleotide polymorphisms by means of allele-specific hybridization (ASH), detection of amplified variable sequences of the plant genome, detection of a 3SR (self-sustained sequence replication), detection of SSRs, SNPs, RFLPs or AFLPs (amplified fragment length polymorphisms). Furthermore, the methods for the detection of ESTs (expressed sequence tags) and SSR markers derived from EST sequences and RAPD (randomly amplified polymorphic DNA) are also known. Depending on the context, the term marker in the specification can also mean a specific chromosome position in the genome of a species where a specific marker (for example, SNP) can be found.

"Operatively linked" means connected in a common nucleic acid molecule in a manner such that the combined elements are positioned and oriented to each other such that transcription of the nucleic acid molecule can take place. A DNA operatively linked to a promoter is under the transcriptional control of this promoter.

A "plant" in the context of the invention can, unless stated otherwise, be of any species of the dicotyledonous and monocotyledonous plants. Preference is given to plants in agriculture or horticulture or for the production of bioenergy (bioethanol, biogas, etc.). These include, by way of example, *Solanum tuberosum, Triticum aestivum, Triticum durum, Triticum spelta, Helianthus annuus, Secale cereale, Hordeum vulgare, Hordeum bulbosum, Brassica napus, Brassica oleracea, Brassica rapa, Brassica juncacea, Brassica nigra, Glycine max, Gossypium* sp., *Sorghum bicolor, Sorghum sudanense, Sorghum bicolor×Sorghum sudanense, triticale, Saccharum officinarium, Setaria italica, Oryza sativa, Oryza minuta, Oryza australiensis, Oryza alta, Brachypodium distachyon, Hordeum marinum, Aegilops tauschii, Daucus glochidiatus, Daucus pusillus, Daucus muricatus, Daucus carota, Eucalyptus grandis, Erythranthe guttata, Genlisea aurea, Musa* sp., *Avena* sp., *Nicotiana sylvestris, Nicotiana tabacum, Nicotiana tomentosiformis, Solanum lycopersicum, Coffea canephora, Vitis vinifera, Cucumis sativus, Morus notabilis, Crucihimalaya himalaica, Crucihimalaya wallichii, Cardamine flexuosa, Lepidium virginicum, Capsella bursa-pastoris, Olmarabidopsis pumila, Arabis hirsuta, Raphanus sativus, Eruca vesicaria sativa, Citrus sinensis, Jatropha curcas, Populus trichocarpa* or *Beta vulgaris.*

A sorghum plant according to the invention is a plant of the genus Sorghum, in particular of the species *Sorghum bicolor, Sorghum sudanense, Sorghum bicolor×Sorghum sudanense, Sorghum×almum (Sorghum bicolor×Sorghum halepense), Sorghum arundinaceum, Sorghum×drummondii, Sorghum halepense* and/or *Sorghum propinquum* or their hybrids and all varieties derived therefrom.

Plant "organs" mean, for example, leaves, stem axis, stem, roots, vegetative buds, meristems, embryos, anthers, ovules, seeds or fruits, in particular grains. The term "plant part" or "plant parts" includes, but is not limited to, the shoot axis or stem, leaves, flowers, inflorescences, roots, fruits and seeds and the pollen. Plant "parts" further mean a combination of several organs, for example, a flower or a seed, or a part of an organ, for example, a cross section from the shoot axis. Plant "tissues" are, for example, callus tissue, storage tissue, meristematic tissues, leaf tissue, shoot tissue, root tissue, plant tumor tissue or reproductive tissue and the formation tissue, ground tissue (the so-called parenchyma), xylem, supporting tissue and the cover tissue (the so-called epidermis). However, the tissue is not limited by this listing. Plant "cells" are understood to mean, for example, isolated cells having a cell wall or aggregates thereof or protoplasts.

A "promoter" is an untranslated DNA segment, typically upstream of a coding region, which includes the binding site for the RNA polymerase and initiates transcription of the DNA. A promoter also contains other elements that act as regulatory gene of gene expression (for example, cis-regulatory elements). A "core or minimal promoter" is a promoter that has at least the basic elements needed for transcription initiation (for example, TATA box and/or initiator).

In the context of the present invention, the term "modifications" refers to a nucleotide sequence which influences the specificity and/or the expression level, for example, in which the regulatory sequence mediates a specific tissue specificity. Such a regulatory sequence can be located upstream of, but also downstream of, the transcription initiation point of a minimal promoter, such as in a transcribed but untranslated leader sequence or within an intron.

A "transgenic plant" refers to a plant having integrated at least one polynucleotide, preferably a heterologous polynucleotide into its genome. Preferably, the polynucleotide is stably integrated, which means that the integrated polynucleotide is stably maintained in the plant, is expressed and can be stably inherited to the offspring. The stable introduction of a polynucleotide into the genome of a plant also includes integration into the genome of a plant of the previous parental generation, wherein the polynucleotide can be stably further inherited. The term "heterologous" means that the introduced polynucleotide, for example, originates from one cell or organism having another genetic background of the same species or another species, or is homologous to the prokaryotic or eukaryotic host cell, but is then located in a different genetic environment and thus differs from any naturally occurring corresponding polynucleotide. A heterologous polynucleotide can be present in addition to a corresponding endogenous gene.

"Suitable for use as a haploid inducer" or "is capable of inducing haploidy" means that a plant is capable producing fertilized seeds having a simple (haploid) chromosome set from a cross with a plant of the same genus, preferably the same species, which does not have the property of a haploid inducer. The use of a haploid inducer, given as the absolute haploid induction rate, means that at least 0.1%, 0.2%, 0.3%, 0.4%, 0.5%, 0.6%, 0.7%, 0.8%, 0.9% or 1%, preferably at least 1.5%, 2%, 2.5%, 3%, 3.5%, 4%, 4.5% or 5%, more preferably at least 6%, 7%, 8%, 9%, 10%, 11%, 12%, 13%, 14% or 15%, or even more preferably at least 20%, 25%, 30%, 35%, 40%, 45% or 50% of fertilized seeds or embryos have a haploid chromosome set.

Arrangements and embodiments of the present invention are described by way of example with reference to the attached figures and sequences:

FIG. 1: Sequence alignment (CLUSTAL O 1.2.4) of the amino acid sequences of the wild-type patatin phospholipase from sorghum (Sorghum_PPL_AA, SEQ ID No.: 3), of the patatin phospholipase from sorghum with an exchange of the amino acid arginine (R) by glutamine (Q) at amino acid position 59 (Sorghum_PPL_R59Q, SEQ ID No.: 6), the patatin phospholipase from sorghum with an exchange of the amino acid valine (V) by isoleucine (I) at amino acid position 162 (Sorghum_PPL_V162I, SEQ ID No.: 9), the patatin phospholipase from sorghum with an exchange of the amino acid serine (S) by leucine (L) at amino acid position 291 (Sorghum_PPL_S291L, SEQ ID No.: 12) and the patatin phospholipase from sorghum with an exchange of the amino acid glutamine (Q) by a stop codon at amino acid position 372 (Sorghum_PPL_Q372Stop, SEQ ID No.: 15). Amino acid positions 59, 162 and 291 are highlighted in black.

FIG. 2: Sequence alignment (CLUSTAL O 1.2.4) of the amino acid sequences of the wild-type patatin phospholipase from sorghum (*Sorghum bicolor*_PPL_AA, SEQ ID No.: 3), of the patatin phospholipase from barley (*Hordeum vulgare*_PPL_AA, SEQ ID No.: 21), the patatin phospholipase from sunflower (*Helianthus annuus*_PPL_AA, SEQ ID No.: 18), the patatin phospholipase 1 from sugar beet (*Beta vulgaris*_PPL1_AA, SEQ ID No.: 24), and the patatin phospholipase 2 from sugar beet (*Beta vulgaris* phospholipase 2_AA, SEQ ID No.: 27). The amino acid positions which represent the functional domain of phospholipase are shown in bold.

DETAILED DESCRIPTION OF THE INVENTION

The present invention provides a plant of the genus Sorghum, hereinafter also referred to as a sorghum plant, which is capable of inducing haploidy. By virtue of this property of haploid induction, the plant is able to produce fertilized seeds or embryos having a simple (haploid) chromosome set from a cross with a plant of the same genus, preferably of the same species, which does not possess the property of a haploid inducer. Through this system, the inventors have been able to provide an efficient system for breeding sorghum plants, because inoculation lines, that is, homozygous father and mother lines for hybrid breeding, can be generated by chromosome doubling in the haploid offspring.

The sorghum plants according to the invention are characterized in that they have one or more modifications which relate to the patatin phospholipase, which either confers the haploid induction property or also improves a naturally present ability for haploid induction or increases the induction performance. Thus, the modification concerning the patatin phospholipase is the cause of the suitability of the sorghum plant according to the invention as a haploid inducer in breeding programs.

Plants according to the invention are characterized in that they have an induction rate of preferably at least 0.5% and thus differ from wild-type plants or non-haploid inducers.

In the experiments carried out in the context of the present invention, it has been found that the patatin phospholipase in sorghum is pollen-specifically expressed and therefore presumably has an influence on the pollen tube growth or the interaction between the gametophytes. Thus, the sorghum plant according to the invention is preferably characterized in that the patatin phospholipase is pollen-specifically expressed and/or has an influence on the pollen tube growth or the interaction between the gametophytes.

In a preferred embodiment, the patatin phospholipase is encoded by the nucleotide sequence according to SEQ ID No.: 1 or 2, or by a nucleotide sequence which is at least 80%, preferably 85%, more preferably 90%, even more preferably 95% and is most preferably 99% identical to SEQ ID No.: 1 or 2 or is encoded by a nucleotide sequence having a sequence complementary to the nucleotide sequence according to SEQ ID No.: 1 or 2 under stringent conditions, or comprises the amino acid sequence shown in SEQ ID No: 3 or a homologous amino acid sequence. As already mentioned above, the sorghum plant according to the present invention comprises plants of any species of the genus Sorghum, in particular of the species *Sorghum bicolor*, *Sorghum sudanense* and *Sorghum bicolor*×*Sorghum sudanense* or their hybrids and all the varieties derived therefrom. Accordingly, it is reasonable to assume that in the course of speciation and variety breeding, the nucleotide sequence and, correspondingly, the amino acid sequence of the patatin phospholipase have changed. In this context, the term homologous means that the genes in question (from two different plant species or varieties) have substantially the same function and a common precursor, and therefore typically exhibit a significant identity in their nucleic acid or encoded amino acid sequence, respectively preferably at least 80%.

In the context of the invention, a "homolog" is understood to mean a protein of the same phylogenetic origin, an "analog" is understood to mean a protein which performs the same function but has a different phylogenetic origin, and an "ortholog" is understood to mean a protein from another species that performs the same function and a "paralog" is understood to mean a protein that has been created by duplication within a species, wherein this copy either retains the same protein function, its expression pattern changes, but not the function, its protein function changes or the original gene function is divided between both copies.

A coded protein (or amino acid sequence) is in principle a homolog in the context of the present invention when it performs the same function, irrespective of whether it has the same or a different phylogenetic origin or originates from the same or a different species. A homolog is further capable of complementing the property of haploid induction, that is, by a modification of the homolog-encoding gene product of the plant from which the gene originates to confer the property of a haploid inducer or to increase the induction performance of a haploid inducer. Accordingly, the relevant homolog to patatin phospholipase encoded by the nucleotide sequence according to SEQ ID No.: 1 or 2 or comprising the amino acid sequence according to SEQ ID No.: 3 can preferably be characterized as being capable of complementing the property of a haploid inducer, which is observed in the sorghum plant according to the invention. Additionally or alternatively, the patatin phospholipase homolog can preferably be characterized by mediating the property of a haploid inducer or increasing the induction performance of a haploid inducer by modifying the gene product encoded by the homolog.

Corresponding techniques and methods for complementation genetics in sorghum are known to the person skilled in the art, for example, from the publication by Li et al., J Genet. 94 (2015), 445-452, in which the sorghum phenotype, which is characterized by a brown midrib and is caused by a point mutation in the bmr-6 gene, was complemented by introduction of the wildtype bmr-6 gene.

As shown in Example 2, an amino acid sequence in the amino acid sequence of the patatin phospholipase from sorghum (SEQ ID No.: 3) in sorghum results in a haploid induction rate of in part greater than 1.5%. It can be assumed that a further increase in the induction rate can result from further amino acid exchanges, which results in a further modification of the coding sequence of the patatin phospholipase. Thus, sorghum plants comprising one or more modifications or mutations related to patatin phospholipase are included in the present invention.

In the context of the present invention, the abovementioned modifications which relate to patatin phospholipase are preferably characterized in that they are mutations which result in one or more amino acid exchanges or in the production of a stop codon in the endogenous DNA sequence coding for the patatin phospholipase.

A mutation means a modification at the DNA level, that is, a change in genetics and/or epigenetics. For example, a change in genetics can be the exchange of at least one nucleobase in the endogenous DNA sequence or in a regulatory sequence of the endogenous DNA sequence. If such a nucleobase exchange takes place, for example, in a promoter, this can result in an altered activity of the promoter since, for example, cis-regulatory elements are modified in such a way that the affinity of a transcription factor for the mutated cis-regulatory element in comparison to the wild-type promoter is altered so that the activity of the promoter with the mutated cis-regulatory element is increased or decreased, depending on whether the transcription factor is a repressor or inducer, or whether the affinity of the transcription factor for the mutated cis-regulatory element is enhanced or attenuated. If such a nucleobase exchange takes place, for example, in a coding region of the endogenous DNA sequence, this can result in an amino acid exchange in the encoded protein, which can cause a change in the activity or stability of the protein in comparison to the wild-type protein. A further example of a change in genetics is the deletion of nucleotides in the regulatory sequence and/or the endogenous DNA sequence and the addition of nucleotides in the regulatory sequence and/or the endogenous DNA sequence. A change in the epigenetics can take place, for example, by an altered methylation pattern of the DNA.

Methods of mutagenizing DNA sequences are described in more detail in the context of the method of obtaining a plant haploid inducer.

Since the described mutations result in an alteration or shortening of the amino acid sequence of the patatin phospholipase, it can be assumed that the mutations change the activity or stability of the patatin phospholipase encoded by the endogenous DNA sequence in the sorghum plant in comparison to a wild-type plant, that is, increase or decrease.

The generation of stop codons in the functional domains of a protein usually results in a loss of function of the protein, whereas the generation of a stop codon after the functional domain could also result in an increase in the activity or stabilization of the protein. In the case of mutations, which are preferably amino acid exchanges, there can be an increase in the activity of the protein, for example, by optimization of the sequence or equally well to inhibition or loss of the activity. Mutations in the promoter region can also result in a change in the expression of the gene.

In accordance with the present invention, therefore, the mutation described changes the biological activity of the patatin phospholipase so that its original function in pollen is no longer performed to the same extent as is the case in the wild-type sorghum.

This can be done, on the one hand, by overexpression of the gene associated with an increased amount of protein and activity, for example, by mutations in the promoter region, by increasing the stability of the protein, for example, by shortening the protein by the generation of a stop codon, or by the formation of a more active form of the patatin phospholipase, for example, by amino acid exchanges in the functional domain, for example, which could result in a faster growth of the pollen tube, a decoupling of the transport of generative cells in the pollen tube with its growth or a disturbed interaction of gametophytes followed by incomplete fertilization followed by chromosome elimination. On the other hand, the overexpression of the gene could also inhibit, prevent or reduce the correct formation, folding and/or stability of the patatin phospholipase. However, there could also be decreased formation or no formation of a functional patatin phospholipase, for example, by mutations in the promoter region, to the formation of a less active, inactive or unstable form of the patatin phospholipase, for example, by the generation of a stop codon or by amino acid exchanges in the functional domain, which in turn could result in faulty fertilization. Likewise, the localization of the patatin phospholipase could be altered by the described mutations, so that it is no longer pollen-specifically expressed, for example.

As a result, sorghum plants having one or more insertions of an expression cassette are also encompassed in the present invention, which is a nucleic acid molecule encoding the patatin phospholipase, which, through the nucleic acid sequence according to SEQ ID No.: 1 or 2 or through a nucleic acid sequence which is at least 80%, preferably 85%, more preferably 90%, even more preferably 95% and most preferably 99% identical to SEQ ID No.: 1 or 2, or encoding a functional part of this patatin phospholipase, or comprising a nucleic acid molecule having a nucleotide sequence which hybridizes with the sequence complementary to the nucleotide sequence of SEQ ID No: 1 or 2 under stringent conditions, or which comprises a nucleic acid molecule encoding the patatin phospholipase having an amino acid sequence according to SEQ ID No: 3 or a homologous amino acid sequence or a functional part thereof, and operatively linked to a promoter, preferably a pollen-specific promoter, wherein the encoded patatin phospholipase or functional portion thereof has one or more mutations resulting in one or more amino acid exchanges or generation of a stop codon and thus providing patatin phospholipase coding for overexpression of the gene encoding in a plant or part thereof as compared to a wild-type plant or corresponding part thereof.

Likewise encompassed in the present invention are sorghum plants in which the expression of the patatin phospholipase is partially or completely inhibited or a reduced amount of the patatin phospholipase protein is present or no functional patatin phospholipase is formed. Thus, the present invention also comprises sorghum plants in which the expression of said patatin phospholipase is partially or completely inhibited by an RNAi approach (Fire et al., Nature 391 (1998), 806-811). Accordingly, the plant according to the invention is further characterized in that it has one or more insertions of an expression cassette comprising a promoter and optionally a terminator which is operatively linked to a nucleic acid molecule encoding a dsRNA which comprises at least 19 or 20, preferably at least 21, 22, 23, 24 or 25, more preferably at least 30, 35, 40, 45 or 50, and most preferably at least 100, 200, 300 or 500 nucleotides complementary to a partial sequence of the nucleotide sequence according to SEQ ID No.: 1 or 2 or a partial sequence of the nucleotide sequence which is at least 80%, preferably 85%, more preferably 90%, even more preferably 95% and most preferably 99% identical to a partial sequence of the nucleotide sequence according to SEQ ID No.: 1 or 2.

In addition, the present invention also encompasses sorghum plants in which there is a knock-out of patatin phospholipase by mutation.

Suitable promoters useful in the expression cassettes can be promoters that are constitutively induced (for example: 35S promoter from the "Cauliflower mosaic virus" (Odell et al., Nature 313 (1985), 810-812), suitable promoters are those which are development-specific (for example: flower-specific promoters) or tissue-specific, in particular those which are specifically active in pollen, (examples: Chen et al., Molecular Biology Reports 37 (2010), 737-744, Zhao et al., Planta 224 (2006), 405-412 or Twell et al. Genes & Development 5(1991), 496-507). Suitable promoters can also be synthetic or chimeric promoters, which do not occur in nature, are composed of several elements and contain a minimal promoter and upstream of the minimal promoter have at least one cis-regulatory element which serves as a binding site for specific transcription factors. Chimeric promoters can be designed according to the desired specificities and are induced or repressed by different factors. Examples of such promoters can be found in Gurr and Rushton (TRENDS in Biotechnology 23 (2005), 275-282) or Venter (Trends in Plant Science 12 (2007), 118-1249. A suitable terminator is, for example, the nos terminator (Depicker et al., Journal of Molecular and Applied Genetics 126 (1982), 561-573). Promoters and other transcriptional regulatory elements are well known and are available to those skilled in the art; see, for example, WO 00/75359 on page 23, line 5 to page 24, line 17.

As shown in Example 2, an exchange of the amino acid arginine by glutamine at amino acid position 59 according to the amino acid sequence of the patatin phospholipase shown in SEQ ID No.: 6 or an exchange of the amino acid valine by isoleucine at amino acid position 162 according to the amino acid sequence of the patatin phospholipase shown in SEQ ID No.: 9 in sorghum plants results in a haploid induction rate greater than 0.5%. It can be seen from FIG. 2 that these amino acid positions lie in the functional domain of the patatin phospholipase, which corresponds to the range of amino acid positions 37 to 240.

Thus, the present invention provides sorghum plants having one or more mutations resulting in amino acid exchange in the range of amino acid positions 37 to 240 according to SEQ ID No.: 3, which preferably corresponds to the functional domain of patatin phospholipase. In a preferred embodiment, the one or more mutations in the range of amino acid positions 40 to 93 or 135 to 204, preferably in the range of amino acid positions 53-85 or 150-192, more preferably in the range of amino acid positions 55-75 or 157-167 result in an amino acid exchange.

Furthermore, exchange of the amino acid serine for leucine at amino acid position 291 according to the amino acid sequence of the patatin phospholipase shown in SEQ ID No.: 12 in sorghum plants results in a haploid induction rate of more than 1.5%. Also, a sorghum haploid inducer could be generated by a mutation in the nucleotide sequence according to SEQ ID No.: 1, which resulted in a stop codon at amino acid position 372 according to SEQ ID No.: 3. This mutation replaced the amino acid glutamine (Q) at position 372 with a stop codon.

It can be seen from FIG. 2 that these positions lie outside the functional domain of the patatin phospholipase.

Thus, the present invention also provides sorghum plants having one or more mutations resulting in amino acid exchange in the range of amino acid positions 241 to 385 according to SEQ ID No.: 3, which preferably corresponds to a region outside the functional domain of the patatin phospholipase, wherein the mutation can also result in a stop codon and thus to a shortening of the patatin phospholipase. In a preferred embodiment, the one or more mutations in the range of amino acid positions 270 to 320, preferably in the range of amino acid positions 285 to 311, more preferably in the range of amino acid positions 285 to 298, result in an amino acid exchange and/or a stop codon in the range of amino acid positions 322-402, preferably in the range of amino acid positions 342-392, more preferably in the range of amino acid positions 362-382.

In a particularly preferred embodiment of the present invention, the plant according to the invention is characterized in that the one or more mutations result in an amino acid exchange at amino acid position 59, 162 and/or 291 and/or in a stop codon at amino acid position 372 according to SEQ ID: 3.

In this connection, in one embodiment of the present invention, the modified patatin phospholipase comprises an amino acid sequence according to SEQ ID No.: 3, in which at least one amino acid exchange is present, wherein arginine (R) at position 59, valine (V) at position 162, and/or serine (S) at position 291 is replaced by another amino acid, preferably by glutamine (Q) at position 59, isoleucine (I) at position 162 and/or leucine (L) at position 291 or is encoded by a nucleotide sequence according to SEQ ID No.: 1, in which at least one nucleotide exchange is present, resulting in an amino acid exchange and/or a stop codon, wherein one or more nucleotides are exchanged at positions 421-423, 815-817, 1420-1422 and/or 1663-1665 according to SEQ ID No.: 1 (corresponding to nucleotide positions 175-177, 484-486, 871-873 and/or 1114-1116 according to SEQ ID No.: 2).

Plants, as eukaryotes, have two or more copies of their genetic information per cell. Each gene is usually represented by two alleles, which can be identical in the homozygous state or different in the heterozygous state. The phenotype of the plant according to the invention is caused by one or more mutations in the patatin phospholipase, wherein the plant according to the invention is homozygous or heterozygous, preferably homozygous for the mutated patatin phospholipase.

In a further embodiment of the present invention, a nucleic acid molecule is claimed which comprises the previously defined specific mutations resulting in the amino acid exchanges R59Q, V162I, S291L and/or Q372stop based on the amino acid sequence according to SEQ ID No.: 3. In this case, the nucleic acid molecule according to the invention is characterized in that its presence in a plant results in the plant being able to induce haploidy or that the induction performance of a plant already capable of inducing haploid is improved. Preferably, the presence of the nucleic acid molecule according to the invention in the absence of a wild-type patatin phospholipase in a plant results in the plant being able to induce haploidy or in improving the induction performance of a plant already capable of inducing haploid.

The nucleic acid molecule according to the invention can be used as a transgene in order to confer the property of a haploid inducer in a plant or to increase the induction performance of a haploid inducer. Preferably, the nucleic acid molecule according to the invention is an isolated nucleic acid molecule which has been dissolved out of its natural or original environment, that is, the genetic context. A nucleic acid molecule can be double-stranded or single-stranded, linear or circular. This can be genomic DNA, synthetic DNA, cDNA or an RNA type, for example, siRNA or miRNA, wherein the nucleobase uracil occurs in RNA instead of the nucleobase thymine.

In a preferred embodiment of the present invention, the nucleic acid according to the invention or an RNA encoded by the nucleic acid or a protein or polypeptide encoded by the nucleic acid has an effect on pollen tube growth in a plant, on the interaction between the gametophytes or on the fertilization as such.

DNA hybridization probes derived from the modified patatin phospholipase sequence, that is, comprising any of the mutations described above, can be used to identify plants according to the invention, that is, be used to detect the mutations in the patatin phospholipase gene. To achieve specific hybridization, such probes should be specific and have at least a length of 15 nucleotides, preferably at least 20 nucleotides. A detailed guidance on the hybridization of nucleic acids can be found in Tijssen, Laboratory Techniques in Biochemistry and Molecular Biology—Hybridization with Nucleic Acid Probes, Part 1, Chapter 2, "Overview of principles of hybridization and the strategy of nucleic acid assay assays," Elsevier, New York (1993); and in Current Protocols in Molecular Biology, Chapter 2, Ausubel, et al., eds, Greene Publishing and Wiley Interscience, New York (1995). The probes can also be used to amplify a range of the modified sequence of the patatin phospholipase that receives at least one of the previously described mutations by the known polymerase chain reaction (PCR) process.

Therefore, a nucleic acid molecule of at least 15, 16, 17, 18, 19 or 20, preferably at least 21, 22, 23, 24 or 25, more preferably at least 30, 35, 40, 45 or 50, and most preferably at least 100, 200, 300, 500 or 1000 nucleotides in length is a subject of the present invention, wherein said nucleic acid molecule specifically hybridizes to a previously described nucleotide sequence comprising the modified patatin phospholipase gene, and comprises one of the mutations or a pair of nucleic acid molecules suitable in a region containing at least one of the mutations to amplify in a polymerase chain reaction (PCR), preferably in the form of an oligonucleotide, preferably with a maximum length of 50 nucleotides. The nucleic acid molecule preferably has the embodiment described under point [12].

A further subject of the invention is vectors comprising the nucleic acid molecule according to the invention or the aforementioned expression cassette. A vector according to the invention can comprise the mutant patatin phospholipase gene having the aforementioned characteristics of the nucleotide sequence operatively linked to a heterologous promoter or can comprise the mutant patatin phospholipase gene together with its natural promoter.

Another vector can comprise the wild-type gene of patatin phospholipase operably linked to a heterologous promoter. Furthermore, a vector can contain a recombinant DNA molecule which has a nucleotide sequence which codes for a double-stranded RNA and thus results in the expression of the patatin phospholipase gene after expression in a plant cell.

Furthermore, a vector can contain the previously described nucleic acid molecule that specifically binds to the mutated nucleotide sequence of the patatin phospholipase.

The described vector can be a plasmid, a cosmid, a phage or an expression vector, a transformation vector, shuttle vector or cloning vector, it can be double or single stranded, linear or circular or can transform a prokaryotic or eukaryotic host either by integration into its genome or extrachromosomally. Preferably, the nucleic acid molecule according to the invention is operably linked in an expression vector having one or more regulatory sequences which permit transcription and optionally expression in a prokaryotic or eukaryotic host cell; see, for example, Sambrook et al., Molecular Cloning: A Laboratory Manual 3rd Ed. Cold Spring Harbor Laboratory Press, Cold Spring Harbor, N.Y., 2001 and international application WO 00/75359 at page 21, line 20 to page 22, line 32. A regulatory sequence, preferably DNA, can be homologous or heterologous to the nucleic acid according to the invention. Preferably, these regulatory sequences are promoters or terminators, in particular a transcription initiation start point, a ribosome binding site, an RNA processing signal, a transcription termination site and/or a polyadenylation signal. In addition, the vectors usually contain indicator/reporter genes or resistance genes to detect the transfer of the desired vector or DNA molecule/nucleic acid molecule and to select the individuals containing them, since direct detection of the expression of the gene is rather difficult. In a preferred embodiment, the vector is a plant vector.

In addition to the vectors described above, the present invention also provides a method comprising the introduction of a described vector into a host cell. The vector can be introduced, for example, by conjugation, mobilization, biolistic transformation, *Agrobacterium*-mediated transformation, transfection, transduction, vacuum infiltration or electroporation. Such methods and methods for the preparation of described vectors are familiar to the person skilled in the art (Sambrook et al. 2001).

In a further aspect, the present invention relates to host cells containing the described vectors, nucleic acid molecules or expression cassettes. A host cell in the context of the invention can be a prokaryotic (for example, bacterial) or eukaryotic cell (for example, a plant cell or a yeast cell). Preferably, the host cell is an *Agrobacterium* such as *Agrobacterium tumefaciens* or *Agrobacterium rhizogenes* or a plant cell comprising the nucleic acid according to the invention, the vector or the expression cassette described. Numerous methods such as both conjugation or electroporation are known to the person skilled in the art, with which methods he can introduce the nucleic acid according to the invention, the vector of the present invention or the expression cassette into an *Agrobacterium*, and methods such as various transformation methods (biolistic transformation, *Agrobacterium*-mediated transformation), with which he can introduce the nucleic acid according to the invention, the vector or the expression cassette of the present invention into a plant cell (Sambrook et al. 2001).

More preferably, the present invention relates to a transgenic plant cell comprising the nucleic acid molecule according to the invention as transgene, the vector of the present invention, or the expression cassette, and a transgenic plant or a part thereof which comprises the transgenic plant cell. Such a transgenic plant cell or plant is, for example, a plant cell or plant which is preferably stably transformed with the nucleic acid molecule according to the invention, with the vector of the present invention, or the expression cassette. A transgenic plant of the present invention is preferably suitable for use as a haploid inducer. In a preferred embodiment of the transgenic plant cell, the nucleic acid molecule is operatively linked to one or more regulatory sequences which allow transcription and optionally expression in the plant cell. A regulatory sequence, preferably DNA, can be homologous or heterologous to the nucleic acid according to the invention. The total construct of the nucleic acid molecule according to the invention and of the regulatory sequence(s) then represents the transgene. A part of a plant can be a fertilized or unfertilized seed, an embryo, a pollen, a tissue, an organ or a plant cell, wherein the fertilized or unfertilized seed, embryo or pollen is produced on the transgenic plant and in its genome, the nucleic acid according to the invention is integrated as a transgene, the vector or the expression cassette. Likewise, the present invention also includes an offspring of the transgenic plant in the genome of which the nucleic acid according to the invention is integrated as a transgene, the vector or the expression cassette and which is suitable for use as a haploid inducer.

In a further aspect, the present invention relates to a method of producing a plant suitable for use as a haploid inducer. The method can comprise the following steps:
(a) mutagenizing plant cells and then regenerating plants from the mutagenized plant cells or mutagenizing plants; and
(b) identifying a plant of (a) having one or more mutations in an endogenous DNA sequence encoding the above-described patatin phospholipase resulting in one or more amino acid exchanges or generation of a stop codon, preferably one or more of the described amino acid exchanges S291L, R59Q, V162I and Q372stop according to the amino acid sequence SEQ ID No.: 3 or result in one or more amino acid exchanges in sequences of plant patatin phospholipases corresponding to the amino acid exchange S291L, R59Q, V162I and Q372stop according to the amino acid sequence SEQ ID No.: 3 and which is capable of inducing the obtaining of haploid offspring at an increased rate compared to a non-mutagenized plant. In this case, at least one mutation causes the property of a haploid inducer to be conferred in the identified plant or the induction performance of a haploid inducer to be increased.

In addition, further investigations indicate that further potential mutagenic sites exist which are suitable for conferring the property of haploid induction to plants or for increasing their induction performance. These mutations result in the exchange of aspartic acid (D) at position 75, glycine (G) at position 79, and/or proline (P) at position 203 of the amino acid sequence according to SEQ ID No.: 3 by another amino acid, preferably by asparagine (N) at position 75, arginine (R) at position 79 and/or leucine (L) at position 203 or that amino acid exchanges corresponding to this amino acid exchange taking place in plant patatin phospholipases.

The endogenous DNA sequence from step (b) of the above method can in principle code for any plant patatin phospholipase. Preferably, the endogenous DNA sequence encodes a patatin phospholipase from sorghum (SEQ ID No.: 3), sunflower (SEQ ID No.: 18), barley (SEQ ID No.: 21), or sugar beet, with sugar beet having two putative patatin phospholipases (SEQ ID No.: 24 and 27). The plant patatin phospholipases mentioned in step (b) are preferably those from sunflower (SEQ ID No.: 18), barley (SEQ ID No.: 21) or sugar beet, wherein sugar beet has two putative patatin phospholipases (SEQ ID No: 24 and 27).

It is known to the person skilled in the art how a mutation in the context of the invention can be achieved by the process of a mutagenization in step (a) of the method for the production of a plant which is suitable for use as a haploid inducer. The mutagenization here includes both conventional mutagenesis and site-specific mutagenesis or "genome editing". The modification at the DNA level is not deliberately induced in conventional mutagenesis. The plant cell or plant is exposed to mutagenic conditions, for example, TILLING by UV light irradiation or the use of chemicals (Till et al., BMC Plant Biology 4 (2004), 12). A further method of random mutagenesis is mutagenesis with the aid of a transposon. Site-specific mutagenesis enables the introduction of modification at the DNA level targeted at predefined sites of the DNA. For example, TALENS (WO 2010/079430, WO 2011/072246), meganucleases (Silva et al., Current Gene Therapy 11 (2011), 11), homing endonucleases (Chevalier, Molecular Cell 10 (2002), 895-905), zinc finger nucleases (Lloyd et al., Proceedings of the National Academy of Sciences of the United States of America 102

(2005), 2232-237 or a CRISPR/Cas system (Gaj et al., Trends in Biotechnology 31 (2013), 397-405) can be used.

The identification of a plant in step (b) can be carried out, for example, by means of molecular markers or probes. DNA probes are, for example, primers or primer pairs, which can be used in a PCR reaction. For example, tilling mutants can be detected or identified by sequencing the target gene in a Tilling population or other methods that detect mismatches in the DNA, such as melting point analyses or use of mismatch-specific nucleases. The present invention also includes primer/primer pairs that can be used for this purpose, for example, primers for patatin phospholipase.

Further, mutants generated by means of transposons can be detected by using transposon specific primers and target gene specific primers in PCR over the entire population and subsequent sequencing of PCR products. Such primers are also encompassed by the present invention. Those skilled in the art know of other means and methods which they can use to identify a plant in step (b). The present invention also relates to molecular markers which detect the presence or absence of a mutation in the endogenous DNA sequence or in a regulatory sequence of the endogenous DNA sequence. For example, such markers are based on an SNP and are specific for the mutation (examples: KASPar or TaqMan markers).

The identification of a plant in step (b) can also be carried out by testing the induction performance as described in pending Example 1. Thus, the present invention also relates to a method for identifying a plant according to the invention by detecting the mutation in the patatin phospholipase gene or by detecting a marker allele which is coupled to the mutation, preferably using molecular markers described above.

An example of a plant produced and identified by such a method is the sorghum plant according to the invention.

The present invention also relates to a plant which is can be produced or is produced by the above method, or a part of this plant, wherein a part of a plant can be a fertilized or unfertilized seed, an embryo, a pollen, a tissue, an organ or a plant cell, wherein the fertilized or unfertilized seed, the embryo or the pollen are produced on the transgenic plant and in the genome of which the at least one mutation is present. Likewise, the present invention also includes an offspring of the plant which has the at least one mutation and is suitable for use as a haploid inducer. In principle, the method can be applied to any plant containing a patatin phospholipase and thus can be given the property of haploid induction. Preferably, this plant is sorghum, sunflower, barley, sugar beet, rye, wheat or potato.

In another aspect, the present invention also relates to a method of producing a transgenic plant suitable for use as a haploid inducer. The method can comprise the following steps:

(a) introducing the nucleic acid molecule according to the invention which encodes the patatin phospholipases described above and has therein one or more mutations resulting in one or more of the described amino acid exchanges or in the generation of a stop codon, preferably resulting in one or more amino acid exchanges selected from S291L, R59Q, V162I and Q372stop according to the amino acid sequence SEQ ID No. 3, introducing a nucleic acid molecule having one or more mutations resulting in one or more amino acid exchanges in sequences of plant patatin phospholipases corresponding to the amino acid exchanges S291L, R59Q, V162I and Q372stop according to the amino acid sequence SEQ ID No. 3, introducing the previously described expression cassette comprising either a nucleic acid molecule encoding the modified patatin phospholipase according to the invention and being operatively linked to a promoter, or comprising a promoter and optionally a terminator being operatively linked to a nucleic acid molecule encoding a dsRNA comprising at least 19 nucleotides of the nucleotide sequence according to SEQ ID No.: 1 or 2 or having a nucleotide sequence of at least 80% identity to the nucleotide sequence according to SEQ ID No.: 1 or 2, or introducing the vector according to the invention into a plant cell; and (b) regenerating transgenic plants from the plant cells (a).

The method of producing a transgenic plant suitable for use as a haploid inducer also includes providing two or more of the nucleic acids described above, selectively also different embodiments of the nucleic acid according to the invention and optionally in one or more vectors, and transforming plant cells by introducing the two or more nucleic acids. Alternatively or additionally, in addition to the nucleic acid according to the invention, one or more further nucleic acids known to be useful for generating a haploid inducer (for example, manipulated cenh3 gene (Ravi and Chan, Nature 464 (2010), 615-618, EP 2 989 889 A1; EP 3 037 540 A1, WO 2016/138021 A1) are provided and transformed or introduced into the breeding system.

The nucleic acid molecule of step (a) of the method of producing a plant suitable for use as a haploid inducer can encode any plant patatin phospholipase. Preferably, the endogenous DNA sequence encodes a patatin phospholipase from sorghum (SEQ ID No.: 3), sunflower (SEQ ID No.: 18), barley (SEQ ID No.: 21), or sugar beet, with sugar beet having two putative patatin phospholipases (SEQ ID No.: 24 and 27). The plant patatin phospholipases mentioned in the same step (b) are preferably those from sunflower (SEQ ID No.: 18), barley (SEQ ID No.: 21) or sugar beet, wherein sugar beet has two putative patatin phospholipases (SEQ ID No: 24 and 27).

The introduction of the nucleic acid molecule or of the vector from (a) takes place by means of transformation, preferably by means of stable transformation of plant cells. The vector can be introduced, for example, by conjugation, mobilization, biolistic transformation, *Agrobacterium*-mediated transformation, transfection, transduction, vacuum infiltration or electroporation. Such methods are familiar to the person skilled in the art (Sambrook et al., 2001). In addition, a nucleic acid molecule can also be introduced into the plant genome via homologous recombination, for example, by means of CRISPR/Cas or CRISPR/Cpf1 and repair template.

The present invention also relates to a transgenic plant which is can be produced or is produced by this method, or a part of this plant, wherein a part of a plant can be a fertilized or unfertilized seed, an embryo, a pollen, a tissue, an organ or a plant cell, wherein the fertilized or unfertilized seed, the embryo or the pollen are produced on the transgenic plant and in the genome of which the introduced nucleic acid is integrated as a transgene or the vector. Likewise, the present invention also includes an offspring of the transgenic plant which has the introduced nucleic acid as a transgene and is suitable for use as a haploid inducer. In principle, the method can be applied to any plant containing a patatin phospholipase and thus can be given the property of haploid induction. Preferably, this plant is sorghum, sunflower, barley, sugar beet, rye, wheat or potato.

In a further aspect, the present invention relates to a method for producing a haploid plant comprising the following steps:
(a) crossing a non-transgenic or transgenic inducer plant of the present invention which is suitable for use as a haploid inducer with a plant of the same genus, preferably of the same species,
(b) selecting a fertilized haploid seed or embryo, and
(c) producing a haploid plant from the seed or embryo from (b).

Preferably, the plant suitable for use as a haploid inducer is used as a pollen parent and crossed with a seed parent of the same genus, preferably of the same species. The plant suitable for use as a haploid inducer can also be used as a seed parent and crossed with a pollen parent of the same genus, preferably of the same species. Both crossing partners in step (a), that is, seed and pollen parents, can also be the same individual. The crossing step then represents a selfing.

Selecting the haploid fertilized seed or embryo can comprise a step of detecting haploidy and the separating of the haploid fertilized seed or embryo from polyploid fertilized seeds or embryos. The detection of haploidy of a fertilized semen or embryo can be phenotypic or genotypic, for example, by providing the inducer with an embryo-specific dominant marker which is visible in all diploid offspring but not in the induced haploid offspring. Furthermore, the ploidy status can be determined by flow cytometry. In addition, a completely homozygous pattern of molecular markers indicates haploid plants. The separation can be automated, for example, based on data from the detection of haploidy.

The present invention also relates to a haploid fertilized seed or embryo which results from crossing in step (a) of the method for producing a haploid plant and to a haploid plant which is can be produced or is produced by this method, or a part of this plant, wherein a part of a plant can be a seed, an embryo, a tissue, an organ or a plant cell. Likewise, the present invention also includes an offspring of the plant.

Furthermore, the present invention also encompasses a double-haploid (diploid) plant or a part thereof, wherein the double-haploid (diploid) plant or part thereof has been produced by chromosome doubling of the haploid plant or part thereof. These double-haploid (diploid) plants can be produced by the following method:
(a) producing a haploid plant by means of the method according to the invention;
(b) doubling the haploid chromosome set in at least one cell of the haploid plant, and
(c) regenerating the diploid plant from the cell of (b).

In the method according to the invention for producing double-haploid plants, the haploid plants from (a) are treated with the cell division inhibitor colchicine. This results in a doubling of the chromosomes. The person skilled in the art knows of this process and it is described, for example, in Segui-Simarro and Nuez, Cytogenetic and Genome Research 120 (2008), 358-369.

General methods for the production of haploid and double haploid plants are known to the person skilled in the art, for example, from Dwivedi et al., Biotechnol. Adv. 33 (2015), 812-29 and Murovec & Bohanec, Biochemistry, Genetics and Molecular Biology "Plant Breeding" (2012), eds. Abdurakhmonov, chapter 5 and can be applied to the present invention.

A further embodiment of the present invention comprises a method of producing hybrid plants by the following steps:

(a) crossing the double-haploid (diploid) plant according to the invention with a second plant of the same genus, preferably of the same species,
(b) selecting the hybrid plants with respect to the desired trait.

The double-haploid plants are homozygous and the known heterosis effect occurs by crossing two homozygous plants, which results in a particularly pronounced performance of hybrid plants. Accordingly, the hybrid plants obtained by such a method are also the subject of the present invention.

In a further aspect, the present invention relates to the use of the nucleic acid according to the invention, the vector according to the invention or the above-described expression cassette in a plant for conferring the property of a haploid inducer or for increasing the induction performance of a haploid inducer or the use of the nucleic acid according to the invention, the vector according to the invention or previously described expression cassette for the production of a plant or transgenic plant suitable for use as a haploid inducer. Furthermore, the present invention also includes the use of a plant according to the invention described above which is suitable for use as a haploid inducer for the production of a haploid fertilized seed or embryo or a haploid plant. The foregoing explanations of objects and methods of the present invention are also applicable to the mentioned uses.

In experiments with sorghum plants according to the invention, a gene could be found, in particular the gene of the patatin phospholipase having one or more mutations which were suitable to confer on the plant the property of a haploidy inducer and an induction performance of at least 0.4% up to 1.5% or more, so that for the first time an efficient and therefore economically applicable system for the production of haploid and double haploid sorghum plants for hybrid breeding could be provided. The method according to the invention for producing such haploid inducers and the identification of patatin phospholipases in further crops can also be transferred to this system.

The following examples illustrate the invention without, however, limiting the scope of the invention. Unless otherwise indicated, standard molecular biology methods were used, see for example, (Sambrook et al., Molecular Cloning: A Laboratory Manual 3rd Ed. Cold Spring Harbor Laboratory Press, Cold Spring Harbor, N.Y., 2001), Fritsch et al., Cold Spring Harbor Laboratory Press: 1989; Mayer et al., Immunochemical Methods In Cell And Molecular Biology, eds., Academic Press, London, 1987) and Weir et al., Handbook Of Experimental Immunology, Volumes I-IV, Blackwell, eds., 1986).

EXAMPLES

1. Identification of Patatin Phospholipase as a Target for Conferring the Property of Haploid Induction in Sorghum In a TILLING population, a sorghum plant was found which was able to induce haploidy with an efficiency of about 1%. There was a focus on various genes as potential targets in the search for the genetic basis that confers this property in the identified sorghum plant. The selection of genes was made based on the fact that they are preferentially expressed in reproductive organs of the plant and in some way play a role in fertilization, because chromosome elimination can occur through defective or incomplete fertilization, for example, by a missing or incorrect transport of the generative cells to the female ovules or by acting on the energy metabolism of the pollen, resulting in a haploid chromosome set.

According to preliminary investigations in the context of the present invention, a mutated gene was then found, which could be identified as patatin phospholipase in sorghum by means of the bioinformatic methods BLASTP and Synteny Study (Altschul et al., Nucleic Acid Res. 25 (1997), 3389-3402) the nucleotide and amino acid sequence of which are illustrated in SEQ ID No.: 1 or SEQ ID No.: 3, and were identified as a pollen-specific expressed patatin phospholipase by RNA sequencing (RNASeq). The mutated gene had a point mutation in the nucleotide sequence of the patatin phospholipase (see SEQ ID No.: 10), which caused an amino acid change from serine to leucine at position 291 (see SEQ ID No.: 12). The point mutation in the nucleotide sequence of the patatin phospholipase was identified using the PCR method with the primers according to SEQ ID Nos.: 44 and 45.

To verify the mutated gene as the cause of the observed haploid induction, the locus containing the gene was introduced into the genetic background of a non-inducer by breeding and biotechnological methods. This made it possible to introduce the property of a haploid inducer into the non-inducer with an average efficiency of 1.5% when the mutation was homozygous and 1.2% when the mutation was heterozygous. During the verification, the mutated gene could be followed by means of PCR with the primers according to SEQ ID Nos.: 36 to 38. The induction performance of a potential inducer was carried out by pollinating sorghum plants with the mutant sorghum plants (containing the mutated gene). In this case, the wild-type sorghum plants used differed genetically from several markers of the potential inducer line. These markers were used to identify homozygous plants, which were subsequently tested for haploidy by means of flow cytometry.

2. Creation of Further In Vivo Sorghum Haploid Inducers

After verifying with the previously described experiment that the patatin phospholipase in the sorghum was a suitable target for conferring the property of haploid induction in the sorghum, further mutations were introduced into the wild-type endogenous gene. A mutation was introduced which resulted in the exchange of the amino acid glutamine (Q) with a stop codon at position 372. This resulted in a shortening of the patatin phospholipase protein and gave the sorghum plant containing this mutation the property of haploid induction with an average efficiency of between 1% and 3%. As illustrated in FIG. 2, the previously described mutations S291L and Q372stop are outside the functional domain of the patatin phospholipase. Therefore, in a next experiment, mutations were introduced into the gene of the patatin phospholipase, which on the one hand, caused an R59Q amino acid exchange and, on the other hand, a V162I amino acid exchange. These two mutations are within the functional domain and cause the sorghum to acquire a haploid-inducer property, wherein initial experiments showed that the induction rate lies above about 0.5%. A sequence alignment of the four mutants together with the wild-type protein is illustrated in FIG. 1.

It is expected that additional or different mutations or the combination of multiple mutations in the patatin phospholipase would result in an increased or further increased induction rate, so that further experiments to screen TILLING populations can be carried out to identify a plant having increased induction performance.

Furthermore, the mutations could also be introduced into the patatin phospholipase not only by means of TILLING or other mutagenesis methods in the various sorghum species and varieties derived therefrom, but, for example, further haploid inducers can be produced by transgenic expression of the patatin phospholipase. For this purpose, the corresponding genes including their promoters from the sorghum inducer lines having the mutations S291L, R59Q, V162I and/or Q372stop in the patatin phospholipase according to SEQ ID No.: 3 are to be cloned. These genes can be cloned into a suitable transformation vector and transformed into the desired plant.

The induction property of the sorghum plants described above can be attributed to the illustrated mutations in the patatin phospholipase, which usually results in a change in the biological activity thereof. However, the biological activity can be changed not only by introducing the described mutations but also by numerous further genetic engineering methods.

For example, the wild-type gene of the patatin phospholipase together with a suitable promoter can be cloned into a transformation vector and transformed into the desired plant, resulting in overexpression of the patatin phospholipase. Furthermore, the patatin phospholipase could be reduced in its activity via RNAi. For this purpose, for example, hairpin constructs are to be produced, which are then cloned into a suitable transformation vector and transformed into the desired plant, including a suitable promoter and terminator, which allow transcription of the hairpin construct before or at the time of pollen formation. Alternatively, knockout mutants that further reduce activity could be found.

3. Creation of New In Vivo Haploid Inducers

First investigations in the context of the present invention give reasonable grounds to stipulate that in some further crops, the property of the haploid induction or an improvement of this property can be conferred via modifications of the patatin phospholipase, in particular via corresponding mutations described above for the sorghum plant or according to the method according to the invention described above. These are target genes encoding putative patatin phospholipases having one of the following amino acid sequences in sunflower (SEQ ID No.: 18), barley (SEQ ID No.: 21), and sugar beet, wherein sugar beet has two potential phospholipases (SEQ ID No.: 24 and 27). A sequence alignment of the protein sequences from sorghum, sunflower, barley and sugar beet is illustrated in FIG. 2, in which additionally the putative functional domain is characterized (bold). The expression of these genes in pollen can be carried out, for example, via RNASeq of pollen.

In accordance with the process according to the invention described above, modifications relating to the patatin phospholipase can now be selectively introduced into sunflower, barley (and other grains such as wheat, rye and oats) and sugar beet. For example, with the aid of the sequence alignment in FIG. 2, the amino acids corresponding to and exchanging those at positions 291, 59, 162 and 372 according to SEQ ID No.: 3 can be identified. Accordingly, sunflower, barley or grain and sugar beet plants are also the subject of the present invention, which are able to induce haploidy, and are characterized in that they have one or more modifications, the one endogenous, preferably pollen-specific, expressed patatin phospholipase correspondingly relating to one of the embodiments characterized in the above items [ ] or claims, in particular for sorghum plants, and/or obtainable by the method according to the invention described above or in the claims. There are already first indications that amino acid exchanges at position 75 (aspartic acid (D) is replaced by asparagine (N) (D75N)), at position 79 (glycine (G) is replaced by arginine (R) (G79R)) and/or at position 203 (proline (P) is replaced by leucine (L) (P203L)) of the amino acid sequence according to SEQ ID No.: 3 can also confer induction of haploids both in sorghum and in other crops.

The invention claimed is:

1. A sorghum plant which is capable of inducing haploidy, wherein the plant has one or more modifications relating to an endogenous gene encoding a patatin phospholipase,
   wherein the patatin phospholipase is encoded by the nucleotide sequence according to SEQ ID NO: 1 or 2 or by a nucleotide sequence which is at least 95% identical to SEQ ID NO: 1 or 2, or which comprises the amino acid sequence shown in SEQ ID NO: 3 or a homologous amino acid sequence,
   wherein the one or more modifications are one or more mutations in the endogenous gene encoding the patatin phospholipase, and
   wherein the one or more mutations result in an amino acid exchange at least at amino acid position 291 according to SEQ ID NO: 3.

2. The plant according to claim 1, wherein the modified patatin phospholipase
   (i) comprises an amino acid sequence according to SEQ ID NO: 3 or a homologous amino acid sequence in which at least one amino acid exchange is present, wherein serine (S) at position 291 according to SEQ ID NO: 3 is replaced by another amino acid;
   (ii) is encoded by a nucleotide sequence comprising the coding sequence of the DNA sequence according to SEQ ID NO: 1 or a DNA sequence which is at least 95% identical to SEQ ID NO: 1, in which at least one nucleotide exchange is present, resulting in an amino acid exchange, wherein one or more nucleotides are exchanged at positions 1420-1422 according to SEQ ID NO: 1;
   (iii) comprises an amino acid sequence according to SEQ ID NO: 12; or
   (iv) is encoded by a nucleotide sequence comprising the coding sequence of the DNA sequence according to SEQ ID NO: 10.

3. A nucleic acid molecule which encodes a mutated patatin phospholipase encoded by the nucleotide sequence according to SEQ ID NO: 1 or 2 or by a nucleotide sequence which is at least 95% identical to SEQ ID NO: 1 or 2, or which comprises the amino acid sequence shown in SEQ ID NO: 3 or a homologous amino acid sequence,
   wherein the one or more modifications are one or more mutations in the endogenous gene encoding the patatin phospholipase,
   wherein the one or more mutations results in an amino acid exchange at the amino acid position 291 according to SEQ ID NO: 3, and
   wherein the presence of the nucleic acid molecule in a plant in the absence of a wild-type patatin phospholipase results in the plant being able to induce haploidy.

4. A plant cell containing the nucleic acid molecule according to claim 3, a vector comprising the nucleic acid molecule or the nucleic acid molecule as a transgene, optionally under the control of a heterologous promoter.

5. A method for obtaining a plant capable of inducing haploidy or having an increased induction rate with respect to the wild type, comprising the following steps:
   (a) (i) mutagenizing plant cells and then regenerating plants from the mutagenized plant cells or mutagenizing plants;
       (ii) identifying a plant from (i) having one or more mutations in an endogenous DNA sequence which result in serine (S) at position 291 of the amino acid sequence according to SEQ ID NO: 3 being replaced by leucine (L) and capable of inducing the obtaining of haploid offspring at an increased rate compared to a non-mutagenized plant; or
   (b) (i) introducing the nucleic acid molecule having one or more mutations which result in serine (S) at position 291 of the amino acid sequence according to SEQ ID NO: 3 being replaced by leucine (L), in a plant cell, and
       (ii) regenerating a plant from the plant cell (i).

6. A plant containing the plant cell according to claim 4.

7. An organ, plant part, tissue or cell of the plant according to claim 1 or seeds or offspring of the plant, wherein
   (i) the seed or the offspring has one or more mutations in the endogenous gene encoding the patatin phospholipase; and/or
   (ii) the seed or the offspring comprises a nucleic acid molecule according to or a vector comprising the nucleic acid molecule, wherein the nucleic acid molecule encodes a mutated patatin phospholipase comprising one or more mutations resulting in an amino acid exchange at the amino acid position 291 according to SEQ ID NO: 3.

8. A method for obtaining a haploid plant, comprising the following steps:
   (a) crossing a plant according to claim 1 with a plant of the same genus, preferably of the same species,
   (b) selecting a fertilized haploid seed or embryo, and
   (c) producing a haploid plant from the seed or embryo from (b).

9. A haploid plant, haploid fertilized seed or embryo obtainable by the method according to claim 8, the haploid plant, haploid fertilized seed or embryo comprising a patatin phospholipase encoded by the nucleotide sequence according to SEQ ID NO: 1 or 2 or by a nucleotide sequence which is at least 95% identical to SEQ ID NO: 1 or 2, or which comprises the amino acid sequence shown in SEQ ID NO: 3 or a homologous amino acid sequence, wherein the one or more modifications are one or more mutations in the endogenous gene encoding the patatin phospholipase, and wherein the one or more mutations result in an amino acid exchange at least at amino acid position 291 according to SEQ ID NO: 3.

10. The organ, plant part, tissue, cell, seed or offspring of the plant according to claim 9.

11. The plant according to claim 1, wherein the one or more mutations in the endogenous gene encoding the patatin phospholipase is a substitution which results in one or more amino acid exchanges.

12. The plant according to claim 6, wherein the plant is sorghum, sunflower, rye, wheat, potato, barley or sugar beet.

13. The plant according to claim 2, wherein the serine (S) at position 291 is replaced by leucine (L).

\* \* \* \* \*